US008822190B2

(12) United States Patent
Reddy et al.

(10) Patent No.: US 8,822,190 B2
(45) Date of Patent: Sep. 2, 2014

(54) POLYMICROBIAL FORMULATIONS FOR ENHANCING PLANT PRODUCTIVITY

(75) Inventors: C. Adinarayana Reddy, East Lansing, MI (US); Lalithakumari Janarthanam, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1288 days.

(21) Appl. No.: 12/354,241

(22) Filed: Jan. 15, 2009

(65) Prior Publication Data

US 2009/0308121 A1      Dec. 17, 2009

Related U.S. Application Data

(60) Provisional application No. 61/011,149, filed on Jan. 15, 2008.

(51) Int. Cl.
*C12N 11/00*       (2006.01)
*C12N 11/02*       (2006.01)
*A01N 63/00*       (2006.01)

(52) U.S. Cl.
USPC ............ 435/174; 435/177; 504/117; 504/118

(58) Field of Classification Search
USPC ........................... 504/117, 118; 435/174, 177
See application file for complete search history.

(56) References Cited

U.S. PATENT DOCUMENTS

| 5,147,441 | A | 9/1992 | Megeed | |
| 5,697,186 | A * | 12/1997 | Neyra et al. | 47/57.6 |
| 6,471,741 | B1 * | 10/2002 | Reinbergen | 71/6 |
| 2005/0060930 | A1 | 3/2005 | Kiss et al. | |
| 2006/0258534 | A1 * | 11/2006 | Hill et al. | 504/100 |

OTHER PUBLICATIONS

David Zuberer, Soil Microbiology FAQ's, 1998; http://organiclifestyles.tamu.edu/soil/microbeindex.html.*
Diehard(TM), "Mycorrhizal Inoculants", reference to 1996 USDA Agriculture Service Report; http://www.hort-enterprises.com/HORTSORB/Diehard2.htm.*
DIEHARD (TM) Bed Prep, Datasheet #9, 1997-2012, downloaded Mar. 12, 2013; retrieved from the Internet: <URL: http://www.horticulturalalliance.com>.*
Trademark Electronic Search, "DIEHARD"; U.S. Appl. No. 75/323,434, filed Jul. 14, 1997; abandoned Jan. 5, 1999.*
"Canadian Application Serial No. 2,712,237—Office Action Received", 2 pgs.
"Canadian Application Serial No. 2,712,237, Response filed Jul. 31, 2012 to Office Action mailed Mar. 14, 2012", 9 pgs.

(Continued)

*Primary Examiner* — Jane C Osewcki
(74) *Attorney, Agent, or Firm* — Schwegman, Lundberg & Woessner, P.A.

(57) ABSTRACT

The present invention relates to eco-friendly compositions and methods for providing plant growth enhancing formulations comprising mixtures of microbial isolates. In particular, numerous bacterial and fungal strains were isolated from a variety of soil types, from rhizospheres and from root nodules of leguminous plants, in designed combinations, for providing plant growth and plant productivity enhancing formulations. These specifically designed polymicrobial formulations would further provide protection against plant pathogens lowering the need for nitrogen containing fertilizers, solubilize minerals, protect plants against pathogens, and make available to the plant valuable nutrients, such as phosphate, thus reducing and eliminating the need for using chemical fertilizers and chemical pesticides.

11 Claims, 49 Drawing Sheets
(5 of 49 Drawing Sheet(s) Filed in Color)

GARDEN PEA plants,
preliminary experiment with and without F1
formulation

Pea plant
with formulation

Pea plant control
(without formulation)

(56) References Cited

OTHER PUBLICATIONS

Howell, C. R., "Mechanisms employed by *Trichoderma* species in the biological control of plant diseases. The history and evolution of current concepts", Plant Disease, 87(1), (Jan. 2003), 4-10.

"Canadian Application Serial No. 2712237, Office Action mailed".

"International Application Serial No. PCT/US2009/000235, International Preliminary Report on Patentability mailed Jul. 20, 2010", 5 pgs.

"International Application Serial No. PCT/US2009/000235, International Search Report mailed Feb. 25, 2009", 3 pgs.

"International Application Serial No. PCT/US2009/000235, Written Opinion mailed Feb. 25, 2009", 4 pgs.

\* cited by examiner

GARDEN PEA plants,
preliminary experiment with and without F1 formulation

Pea plant with formulation       Pea plant control (without formulation)

GARDEN PEA plants

Tomato plants

Tomato plants:
AFTER 2 MONTHS OF GROWTH

PURPLE HULL PEA plants

SOYBEAN plants

WONDER BUSH BEAN plants

WONDER BUSH BEAN plants

SQUASH plants

SQUASH plants

TOMATO PLANTS: EXPERIMENT 2

FIG 12 EGGPLANT (BRINJAL) PLANTS: EXPERIMENT 2

RICE PLANTS: EXPERIMENT 2

Root Nodules: Garden Beans (Rhizobial noculum comparisons)

Root Nodules: Garden Beans (Rhizobial noculum comparisons)

Root Nodules: Garden Beans (Rhizobial noculum comparisons)

Root Nodules: Garden Beans (Rhizobial noculum comparisons)

Root Nodules: Garden Beans (Rhizobial noculum comparisons)

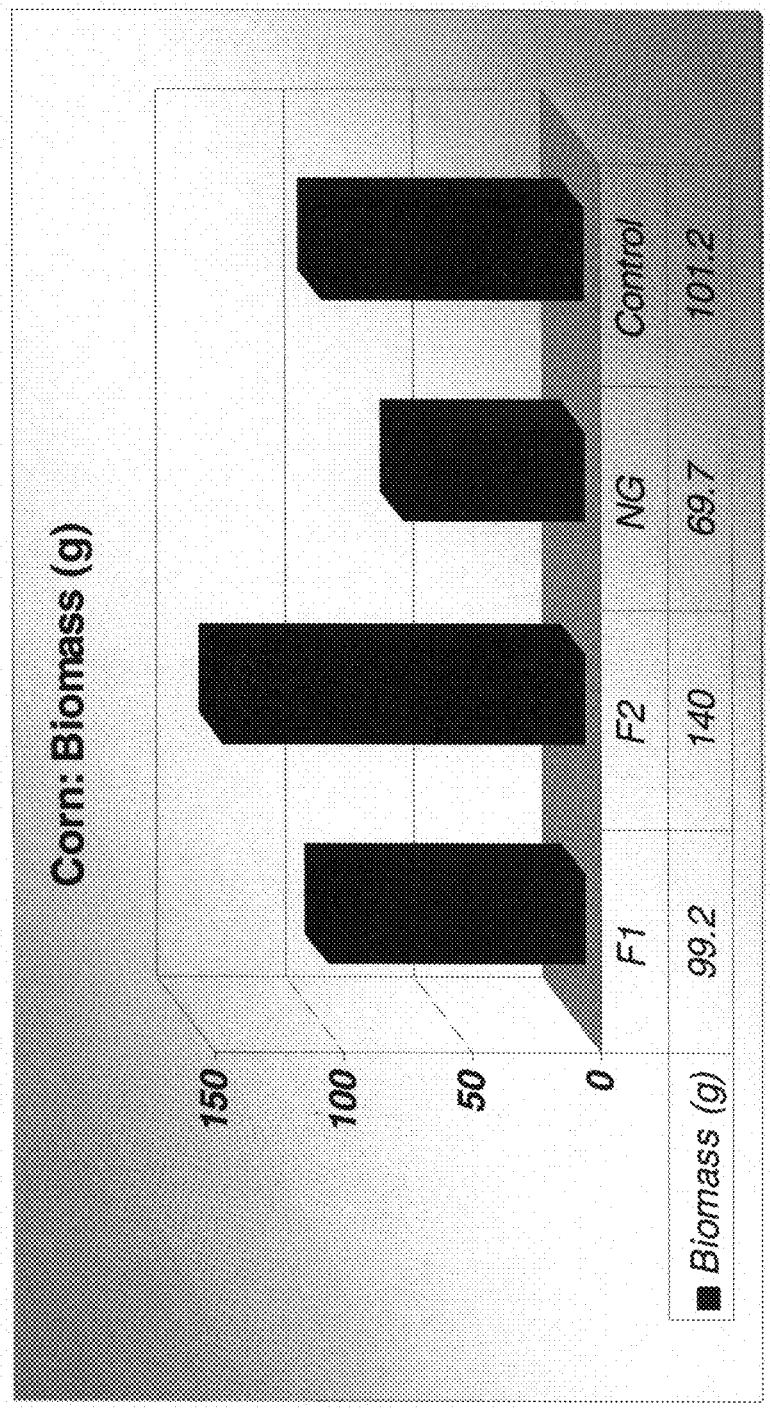

Okra Fruit weight

Rice grain yield comparison from a Field Trial

Rice plant height comparison from a Field Trial and Green House Trial

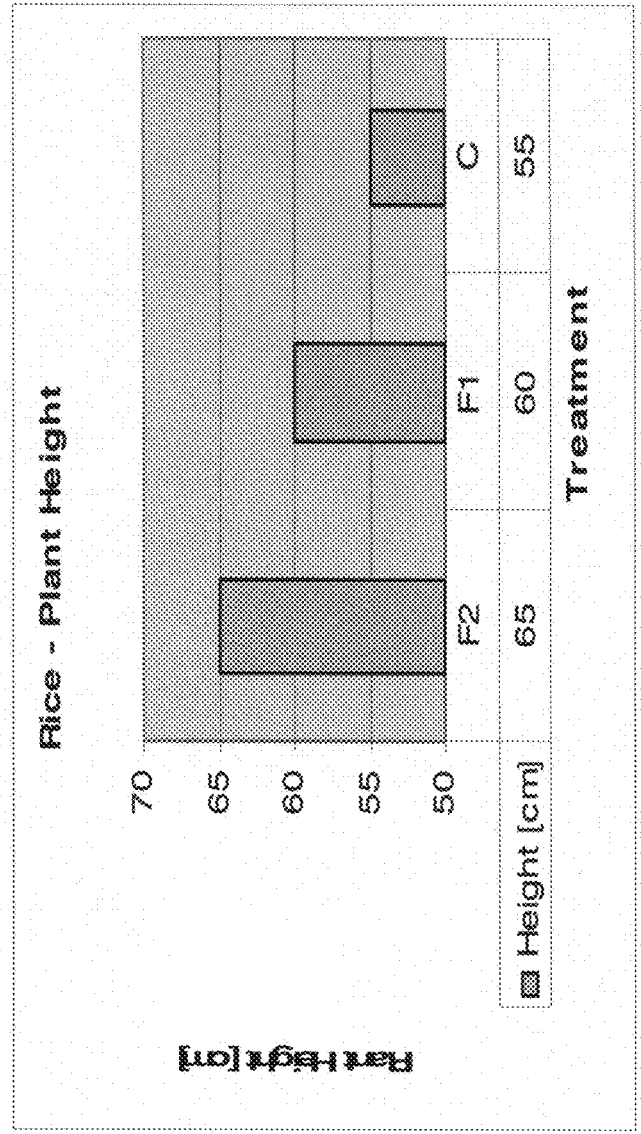

Rice plant height comparison from a Field Trial and Green House Trial

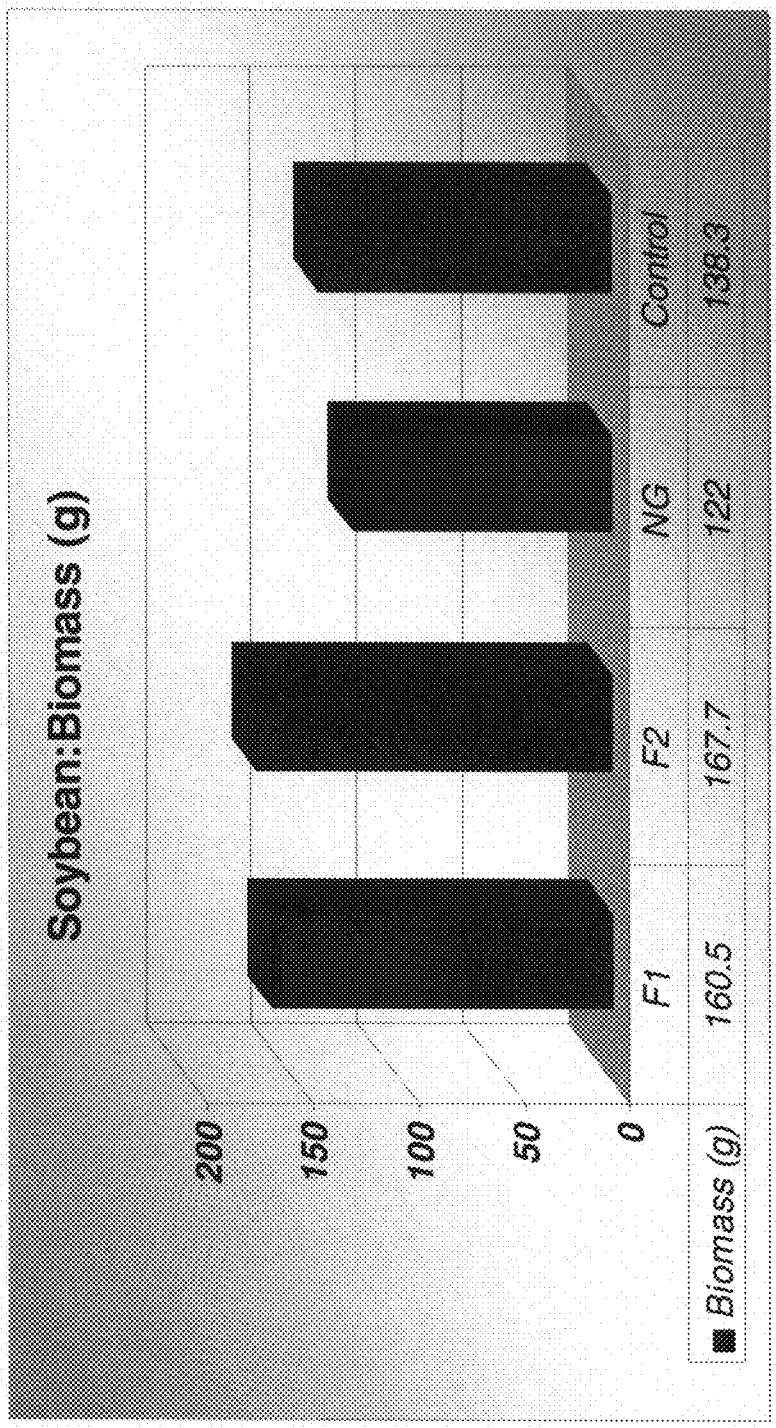

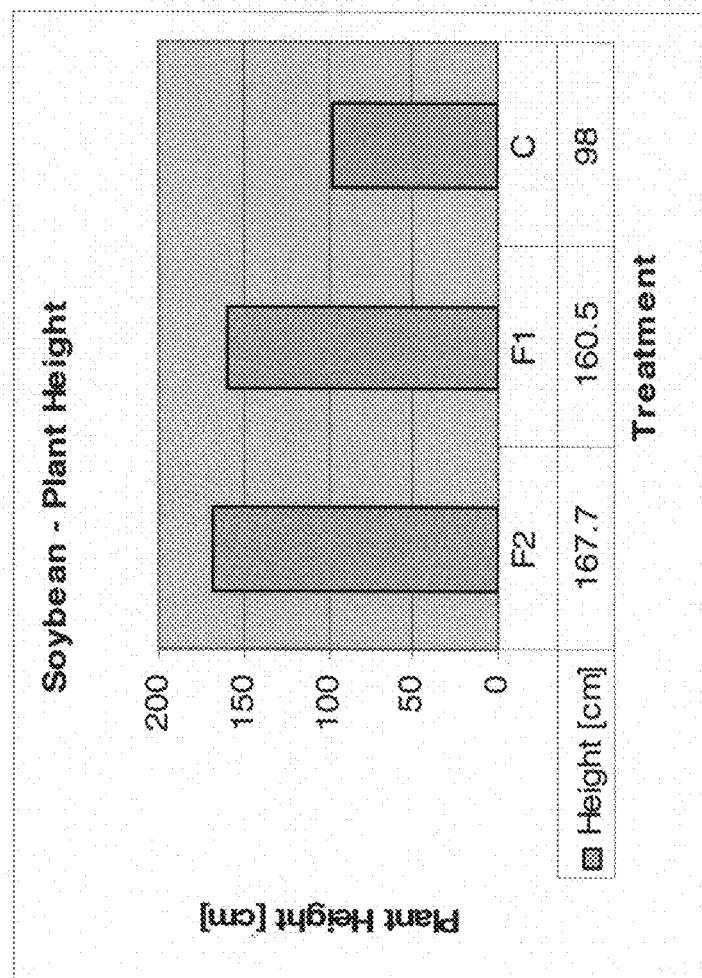
FIG 22B Soybean Biomass comparison from a Field Trial and Green House Trial Soybean Biomass comparison from a Field Trial and Green House Trial Tomato plant height comparison from a Field Trial and Green House Trial Tomato plant height comparison from a Field Trial and Green House Trial Wonder bush beans from a Green House Trial Wonder bush beans from a Green House Trial

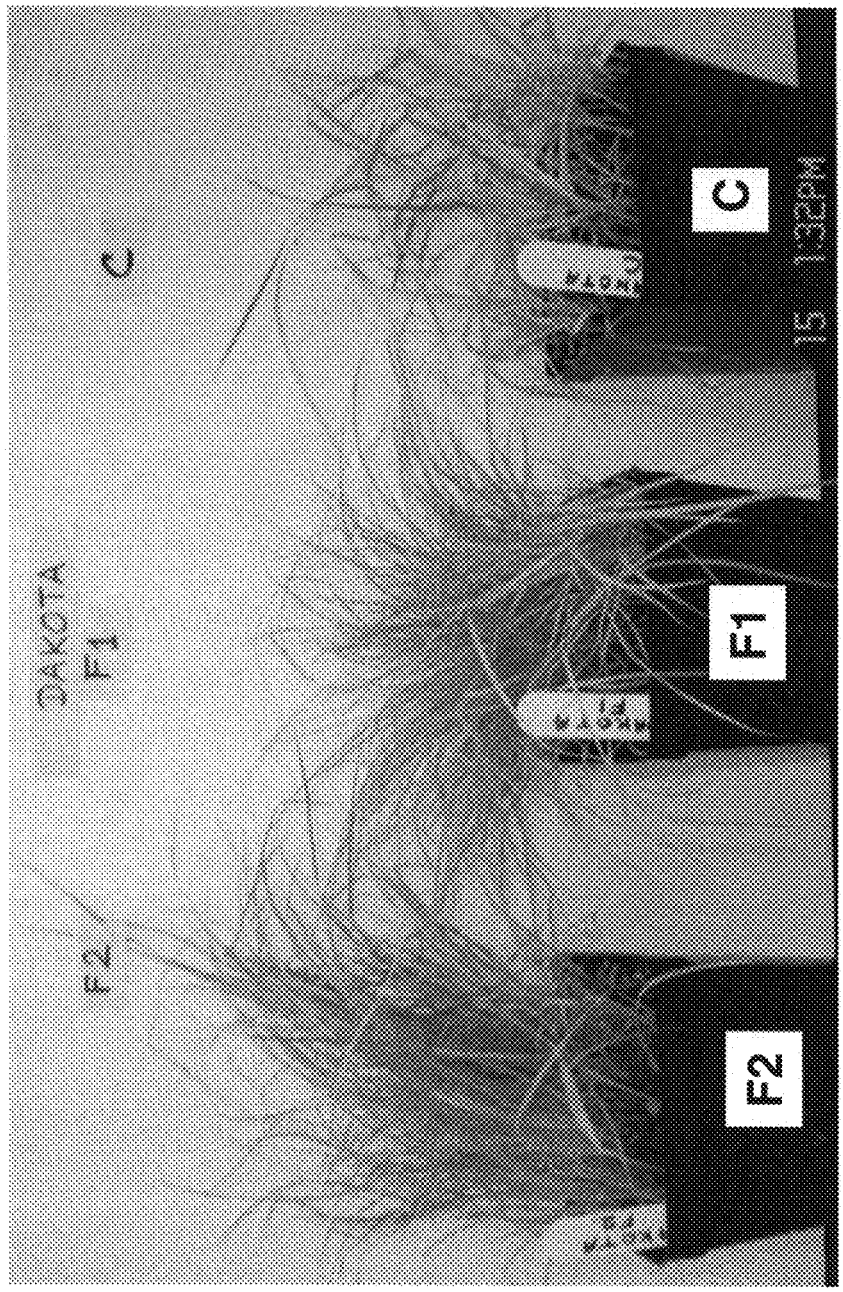

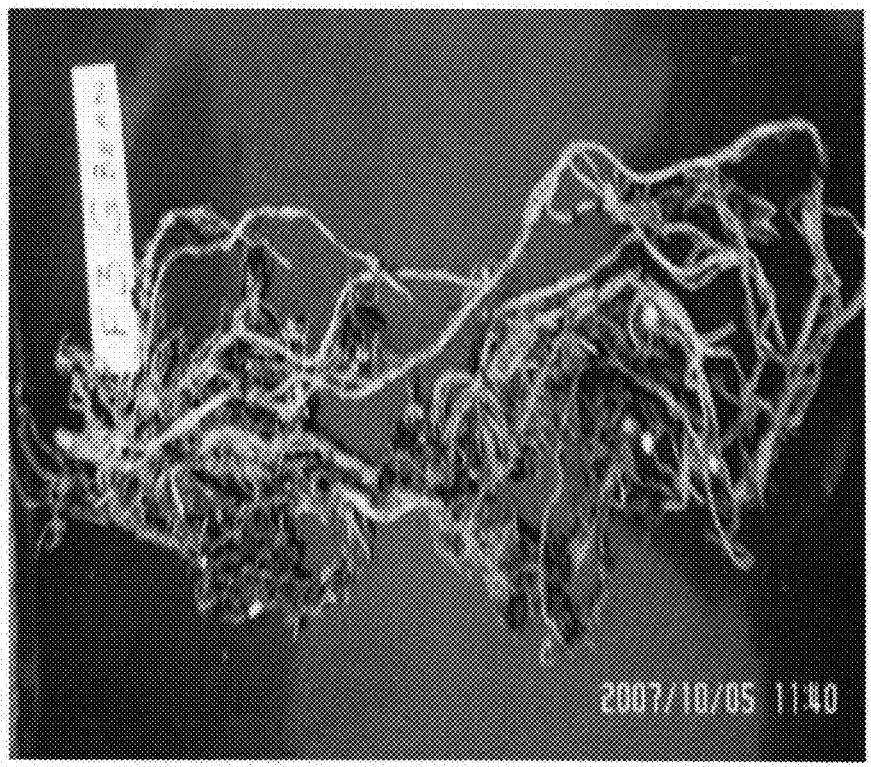
FIG 28A Pea Plant roots

Pea Plant roots

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
agagtttgat cctggctcag                                          20

<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
```

```
ggttaccttg ttacgatt                                                    18

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
taccgcggct gctggcac                                                    18
```

POLYMICROBIAL FORMULATIONS FOR ENHANCING PLANT PRODUCTIVITY

FIELD OF THE INVENTION

The present invention relates to eco-friendly compositions and methods for providing plant growth enhancing formulations comprising mixtures of beneficial microbial isolates. In particular, numerous bacterial and fungal strains were isolated from a variety of soil types, from rhizospheres and from root nodules of leguminous plants, in designed combinations, for providing plant growth and plant productivity enhancing formulations. These specifically designed polymicrobial formulations would further provide protection against plant pathogens lowering the need for nitrogen containing fertilizers, solubilize minerals, protect plants against pathogens, and make available to the plant valuable nutrients, such as phosphate, thus reducing and eliminating the need for using chemical pesticides and chemical fertilizers.

BACKGROUND

For a long time plant biologists knew that a number of species of rhizobacteria (bacteria naturally occurring in the plant rhizosphere) beneficially affected plant growth albeit by employing different mechanisms. These mechanisms include: 1) contribution to the nitrogen economy of the plant by fixing atmospheric nitrogen ($N_2$); 2) producing growth stimulant compounds such as various auxins; and 3) inhibiting a number of plant pathogenic bacteria and fungi. Therefore, it was believed that naturally occurring rhizobacteria contributed not only to increased plant growth but was also to protect plants against pathogens.

Numerous types of rhizobacteria have been isolated and applied exogenously to plants as growth enhancers with a stated goal of minimizing the need for environmentally harmful chemical pesticides and fertilizers. However, due to the complexity of the rhizosphere, bacterial additions to the soil do not result in the types of increases in plant growth or productivity expected by the plant growers.

Thus it would greatly benefit our environment to have naturally derived microbial products for increasing plant growth and for reducing the need for applications of pesticides.

SUMMARY OF THE INVENTION

The present invention relates to eco-friendly compositions and methods for providing plant growth enhancing formulations comprising mixtures of microbial isolates. In particular, numerous bacterial and fungal strains were isolated from a variety of soil types, from rhizospheres and from root nodules of leguminous plants, in designed combinations, for providing plant growth and plant productivity enhancing formulations. These specifically designed polymicrobial formulations would further provide protection against plant pathogens lowering the need for nitrogen containing fertilizers, solubilize minerals, protect plants against pathogens, and make available to the plant valuable nutrients, such as phosphate, thus reducing and eliminating the need for using chemical pesticides and chemical fertilizers.

The present invention provides exemplary isolates of soil bacterial strains and fungal strains as described herein.

Specifically, the present invention provides an isolated *Ensifer meliloti* FD bacterial strain having accession number _____.

The present invention provides an isolated *Rhizobium trifolii* FD bacterial strain having accession number _____.

The present invention provides an isolated *Azorhizobium caulinodans* KN bacterial strain having accession number _____.

The present invention provides an isolated *Rhizobium* sp. RLG1 bacterial strain having accession number _____.

The present invention provides an isolated *Azorhizobium* sp. RLG2 bacterial strain having accession number _____.

The present invention provides an isolated *Azorhizobium* sp. RLG3 bacterial strain having accession number _____.

The present invention provides an isolated *Rhizobium* sp. RLG4 bacterial strain having accession number _____.

The present invention provides an isolated *Rhizobium* sp. RLG5 bacterial strain having accession number _____.

The present invention provides an isolated *Rhizobium* sp. RLG6 bacterial strain having accession number _____.

The present invention provides an isolated *Azorhizobium* sp. RLG7 bacterial strain having accession number _____.

The present invention provides an isolated *Rhizobium* sp. RLG8 bacterial strain having accession number _____.

The present invention provides an isolated *Azorhizobium* sp. RLG9 bacterial strain having accession number _____.

The present invention provides an isolated *Rhizobium* sp. RLG10 bacterial strain having accession number _____.

The present invention provides an isolated *Rhizobium* sp. RLG11 bacterial strain having accession number _____.

The present invention provides an isolated *Trichoderma virens* 3107 fungal strain having accession number _____.

The present invention provides an isolated *Trichoderma viride* LK fungal strain having accession number _____.

The present invention provides an isolated *Trichoderma viride* 3116 fungal strain having accession number _____.

The present invention provides an isolated *Trichoderma harzianum* 3147 fungal strain having accession number _____.

The present invention provides an isolated *Trichoderma harzianum* G fungal strain having accession number _____.

The present invention provides an isolated *Trichoderma harzianum* LK fungal strain having accession number _____.

The present invention provides an isolated *Trichoderma longibrachiatum* 3108 fungal strain having accession number _____.

The present invention provides an isolated *Bacillus* sp. LK bacterial strain having accession number _____.

The present invention provides an isolated *Bacillus subtilis* LK bacterial strain having accession number _____.

The present invention provides an isolated *Pseudomonas fluorescens* CA bacterial strain having accession number _____.

The present invention provides an isolated *Azospirillum* CA bacterial strain having accession number _____.

The present invention provides an isolated *Acetobacter* sp. LK bacterial strain having accession number _____.

The present invention provides an isolated *Rhizobium phaseoli* CA bacterial strain having accession number _____.

The present invention provides an isolated *Bradyrhizobium japonicum* CA bacterial strain having accession number _____.

The present invention provides an isolated *Rhizobium meliloti* FD bacterial strain having accession number _____.

The present invention provides an isolated *Paenibacillus brasiliensis* 172 bacterial strain having accession number _____.

The present invention provides a microbial formulation, wherein said formulation comprises at least two microbial isolates. In one embodiment, the two microbial isolates are isolated from soil. In one embodiment, the two microbial isolates are isolated from a root nodule. In one embodiment, the two microbial isolates consist of a soil microbial isolate and a root nodule isolate. In one embodiment, said formulation comprises at least seven microbial isolates. In one embodiment, said formulation comprises at least twenty-one microbial isolates. In one embodiment, said formulation comprises at least seven microbial isolates. In one embodiment, said formulation comprises at least twenty-one microbial isolates. In one embodiment, said formulation comprises at least twenty-one microbial isolates. In one embodiment, said formulation consists of twenty-one microbial isolates. In one embodiment, said formulation comprises up to at least forty microbial soil isolates. In one embodiment, said formulation comprises up to at least forty microbial soil isolates. In one embodiment, said formulation comprises at least seven and up to forty microbial soil isolates. In one embodiment, said microbial isolate is selected from the group consisting of a bacterial isolate and a fungal isolate. In one embodiment, said fungal isolate is selected from the group consisting of a *Trichoderma virens* 3107 fungal strain having accession number _____, a *Trichoderma viride* G fungal strain having accession number _____, a *Trichoderma viride* LK fungal strain having accession number _____, a *Trichoderma harzianum* 3147 fungal strain having accession number _____, a *Trichoderma harzianum* G fungal bacterial strain having accession number _____, a *Trichoderma harzianum* LK fungal strain having accession number _____, a *Trichoderma longibrachiatum* 3108 fungal strain having accession number _____, In one embodiment, said bacterial soil isolate is selected from the group consisting of a *Bacillus* sp. RG-S bacterial strain having accession number _____, an *Ensifer meliloti* FD bacterial strain having accession number _____, a *Rhizobium trifolii* FD bacterial strain having accession number _____, an *Azorhizobium caulinodans* KN bacterial train having accession number _____, a *Rhizobium* sp. RLG1 bacterial strain having accession number _____, an *Azorhizobium* sp. RLG2 bacterial strain having accession number _____, an *Azorhizobium* sp. RLG3 bacterial strain having accession number _____, a *Rhizobium* sp. RLG4 bacterial strain having accession number _____, a *Rhizobium* sp. RLG5 strain having accession number _____, a *Rhizobium* sp. RLG6 bacterial strain having accession number _____, *Azorhizobium* sp. RLG7 bacterial strain having accession number _____, a *Rhizobium* sp. RLG8 bacterial strain having accession number _____, an *Azorhizobium* sp. RLG9 bacterial strain having accession number _____, a *Rhizobium* sp. RLG10 bacterial strain having accession number _____, a *Rhizobium* sp. RLG11 bacterial strain having accession number _____, a *Bacillus* sp. LK bacterial strain having accession number _____, a *Pseudomonas fluorescens* CA bacterial strain having accession number _____, an *Azospirillum* CA bacterial strain having accession number _____, an *Acetobacter* sp. LK bacterial strain having accession number _____, a *Rhizobium phaseoli* CA bacterial strain having accession number _____, a *Bradyrhizobium japonicum* bacterial strain having accession number _____, a *Rhizobium meliloti* FD bacterial strain having accession number _____, a *Paenibacillus brasiliensis* 172 bacterial strain having accession number _____, a *Paenibacillus peoriae* bacterial strain having accession number BD-62, a *Paenibacillus polymyxa* bacterial strain having accession number B37-A. In one embodiment, said microbial soil isolate is selected from the group consisting of a *Bacillus* sp. RG-S bacterial strain having accession number _____, an *Ensifer meliloti* FD bacterial strain having accession number _____, a *Rhizobium trifolii* FD bacterial strain having accession number _____, an *Azorhizobium caulinodans* KN bacterial train having accession number _____, a *Rhizobium* sp. RLG1 bacterial strain having accession number _____, an *Azorhizobium* sp. RLG2 bacterial strain having accession number _____, an *Azorhizobium* sp. RLG3 bacterial strain having accession number _____, a *Rhizobium* sp. RLG4 bacterial strain having accession number _____, a *Rhizobium* sp. RLG5 strain having accession number _____, a *Rhizobium* sp. RLG6 bacterial strain having accession number _____, *Azorhizobium* sp. RLG7 bacterial strain having accession number _____, a *Rhizobium* sp. RLG8 bacterial strain having accession number _____, an *Azorhizobium* sp. RLG9 bacterial strain having accession number _____, a *Rhizobium* sp. RLG10 bacterial strain having accession number _____, a *Rhizobium* sp. RLG11 bacterial strain having accession number _____, a *Trichoderma virens* 3107 fungal strain having accession number _____, a *Trichoderma viride* LK fungal strain having accession number _____, a *Trichoderma viride* 3116 fungal strain having accession number _____, a *Trichoderma harzianum* 3147 fungal strain having accession number _____, a *Trichoderma harzianum* G fungal strain having accession number _____, a *Trichoderma harzianum* LK fungal strain having accession number _____, a *Trichoderma longibrachiatum* 3108 fungal strain having accession number _____, a *Bacillus* sp. LK bacterial strain having accession number _____, a *Pseudomonas fluorescens* CA bacterial strain having accession number _____, an *Azospirillum* CA bacterial strain having accession number _____, an *Acetobacter* sp. LK bacterial strain having accession number _____, a *Rhizobium phaseoli* CA bacterial strain having accession number _____, a *Bradyrhizobium japonicum* bacterial strain having accession number _____, a *Rhizobium meliloti* FD bacterial strain having accession number _____, a *Paenibacillus brasiliensis* 172 bacterial strain having accession number _____, a *Paenibacillus peoriae* bacterial strain having accession number BD-62, a *Paenibacillus polymyxa* bacterial strain having accession number B37-A. In one embodiment, said microbial soil isolate is selected from the group consisting of a *Bacillus* sp. LK bacterial strain having accession number _____, an *Bacillus subtilis* LK bacterial strain having accession number _____, a *Rhizobium trifolii* FD bacterial strain having accession number _____, an *Azorhizobium caulinodans* KN bacterial train having accession number _____, a *Pseudomonas fluorescens* bacterial strain having accession number _____, an *Azospirillum* CA bacterial strain having accession number _____, an *Acetobacter* sp. LK bacterial strain having accession number _____, a *Rhizobium phaseoli* CA bacterial strain having accession number _____, a *Bradyrhizobium japonicum* bacterial strain having accession number _____, an *Azorhizobium caulinodans* KN bacterial strain having accession number _____, *Trichoderma virens* 3107 fungal strain having accession number _____, a *Trichoderma viride* 3116 fungal strain having accession number _____, a *Trichoderma harzianum* 3147 fungal strain having accession number _____, a *Trichoderma longibrachiatum* 3108 fungal strain having accession number _____. In one embodiment, said microbial formulation further comprises a carrier, such that the microbial formulation of the present inventions are delivered to a seed or plant in a manner to promote growth and productivity, such as germination, yield, and the like. It is not meant to limit the type of carrier. Indeed, a variety of carriers are contemplated including but not limited to a liquid, a solid and a combination of a liquid and a solid carrier. In a preferred embodiment, the carrier is a liquid comprising water. In some embodiments, a carrier comprises a microbial growth medium. In some embodiments, a carrier further comprises humic acid, minerals, artificial compounds, particles, such as beads, powders or granules, and the like. In some embodiments, a particle comprises a resin, clay, a biodegradable compound, and the like. In one embodiment, a bead comprises polymethyl methacrylate (PMMA).

In one embodiment, minerals comprise elements, such as Ca, Mg, and the like. In some embodiments, minerals are compounds such as $NH_4NO_3$, $KH_2PO_4$, $K_2HPO_4$, $MgSO_4$, $Ca(NO_3)$, KCl, $KH_2PO_4$, $MgSO_4$, $CaSO_4$, and the like. In one embodiment, minerals comprise trace elements, including but not limited to any trace mineral comprising a trace element of benefit to a microbe and a plant. Examples of such trace minerals are $H_2BO_3L$, $ZnSO_4$, $CuSO_4$, $MnCl_2$, $Na_2MoO_4$, et cetera. Both synthetic and natural compounds are contemplated as components of formulations of the present inventions, in particular for providing a benefit to a microbe or a plant, such as providing pathogen resistance, fungal resistance, reducing weeds, for example, an herbicide, a pesticide, a fungicide, a plant growth regulator, and for enhancing the effect of the microbial compound, for example, an encapsulation agent, a wetting agent, a dispersing agent, and the like. In one embodiment, a herbicide includes but is not limited to imazethapyr, 2,2-dichloropropionic acid, glyphosate, 2,4-dichlorophenoxyacetic acid (2,4-D), etc., and derivatives thereof. In one embodiment, a pesticide includes but is not limited to O, S-dimethyl acetylphos-phoramidothioate (acephate), carbamate, carbaryl, chrlopyrifos-methyl, dicrotophos, indoxacarb, 2-(dimethoxyphosphinothioylthio) (malathion), methomyl, methoxyfenozide, methyl parathion, pyrethrins, synthetic pyrethroids (such as bifenthrin, cypermethrin and the like), pyrethroids, protenophos, phorate, spinosyn, dimethyl N,N'-[thiobis[(methylimino)carbonyloxy]]-bis[ethanimidothioate](thiodicarb), and derivatives thereof. In one embodiment, a plant growth regulator includes but is not limited to 2,2-dichloropropionic acid, and the like.

In one embodiment, said liquid carrier comprises water and humic acid. In one embodiment, said humic acid ranges from a concentration of 0.0001%-60% volume/volume. In one embodiment, said humic acid is 12% volume/volume. In one embodiment, said liquid carrier comprises a mineral solution. It is not meant to limit the mineral solution, indeed a variety of minerals are contemplated for use including but not limited to individual minerals such as Ca, Co, Mg, Fe, etc., and mineral compounds such as $CoCL_2$, $H_3BO_3$, $MnCL_2$, $ZnSO_4$, $CuSO_4$, $H_2MoO_4$, $MgSO_4$, $K_2HPO_4$, $KH_2PO_4$, $CaCL_2$, $FeC_6H_5O_7$, etc. In one embodiment, said liquid carrier has a pH ranging from 5-9. In one embodiment, said liquid carrier has a pH of 7.0. The concentration of microbes in a liquid carrier may alter depending upon the carrier and the target amount of plant enhancing characteristics. However, any concentration that will achieve plant-enhancing characteristics is desired. In some embodiments, said microbial isolate concentration in the liquid carrier ranges from $10^{10}$-$10^{17}$ microbes per milliliter of liquid. In one embodiment, said microbial isolate concentration in the liquid carrier is selected from the group consisting of $10^{10}$, $10^{14}$, $10^{15}$, and $10^{17}$.

The present invention provides a method for enhancing plant growth, comprising, a) providing, i) a microbial formulation comprising a microbial soil isolate, wherein said microbial soil isolate is selected from the group consisting of a *Bacillus* sp. RG-S bacterial strain having accession number _____, an *Ensifer meliloti* FD bacterial strain having accession number _____, a *Rhizobium trifolii* FD bacterial strain having accession number _____, an *Azorhizobium caulinodans* KN bacterial train having accession number _____, a *Rhizobium* sp. RLG1 bacterial strain having accession number _____, an *Azorhizobium* sp. RLG2 bacterial strain having accession number _____, an *Azorhizobium* sp. RLG3 bacterial strain having accession number _____, a *Rhizobium* sp. RLG4 bacterial strain having accession number _____, a *Rhizobium* sp. RLG5 strain having accession number _____, a *Rhizobium* sp. RLG6 bacterial strain having accession number _____, *Azorhizobium* sp. RLG7 bacterial strain having accession number _____, a *Rhizobium* sp. RLG8 bacterial strain having accession number _____, an *Azorhizobium* sp. RLG9 bacterial strain having accession number _____, a *Rhizobium* sp. RLG10 bacterial strain having accession number _____, a *Rhizobium* sp. RLG11 bacterial strain having accession number _____, a *Trichoderma virens* 3107 fungal strain having accession number _____, a *Trichoderma viride* LK fungal strain having accession number _____, a *Trichoderma viride* 3116 fungal strain having accession number _____, a *Trichoderma harzianum* 3147 fungal strain having accession number _____, a *Trichoderma harzianum* G fungal strain having accession number _____, a *Trichoderma harzianum* LK fungal strain having accession number _____, a *Trichoderma longibrachiatum* 3108 fungal strain having accession number _____, a *Bacillus* sp. LK bacterial strain having accession number _____, a *Pseudomonas fluorescens* CA bacterial strain having accession number _____, an *Azospirillum* CA bacterial strain having accession number _____, an *Acetobacter* sp. LK bacterial strain having accession number _____, a *Rhizobium phaseoli* CA bacterial strain having accession number _____, a *Bradyrhizobium japonicum* bacterial strain having accession number _____, a *Rhizobium meliloti* FD bacterial strain having accession number _____, a *Paenibacillus brasiliensis* 172 bacterial strain having accession number _____, a *Paenibacillus peoriae* bacterial strain having accession number BD-62, a *Paenibacillus polymyxa* bacterial strain having accession number B37-A; and ii) a plant, and applying said microbial formulation to a plant for enhancing plant productivity. In one embodiment, said microbial formulation further comprises a liquid carrier. In a further embodiment, said microbial formulation further comprises mixing said liquid carrier with said microbial isolate. In one embodiment, said liquid carrier comprises water and humic acid. In one embodiment, said humic acid is at a concentration of 12% v/v (Volume of solute (ml)/Volume of solution (ml)). In one embodiment, said liquid carrier has a pH of 7.0. In one embodiment, said microbial isolate concentration in the liquid carrier ranges from $10^{10}$-$10^{17}$ microbes per milliliter of liquid formulation. In one embodiment, said applying is selected from the group consisting of seed dipping, root dipping, seedling root dip, soil drench, pipetting, irrigating, spraying, foliar spraying, spraying at the base of the plants, and the like. In one embodiment, said plant is selected from the group consisting of a vegetable plant, a legume plant, a cereal plant, a fodder plant, a grass plant, a fiber plant, an oil seed plant, a field pant, a garden plant, a green-house plant, and a house plant. In one embodiment, said plant is selected from the group consisting of a tomato plant, an eggplant plant, an okra plant, a squash plant, a zucchini plant, a bean plant, a pea plant, a soybean plant, a rice plant, a corn plant, a sorghum plant, an alfalfa plant, a grass plant, a turf grass plant, a clover plant, a cotton plant, and a peanut plant. In one embodiment, said enhancing plant productivity is increasing an agriculturally desirable trait. In one embodiment, said agriculturally desirable trait is selected from the group consisting of percentage of seed germination, quality of seed germination, height of the plant, width of plant, equivalent leaf area, shoot length, root length, legume nodulation, number of legume nodules, grain yield, fruit yield, shoot weight, root weight, biomass, altered time for flowering, altered time for fruit formation, decreased disease incidence, and increased disease resistance. In one embodiment, said agriculturally desirable trait is evaluated at 30-60 days after sowing.

The present invention provides exemplary isolated bacterial strains selected from the group consisting of an *Ensifer meliloti* FD, *Rhizobium trifolii* FD, *Azorhizobium caulinodans* KN, *Rhizobium* sp. RLG1, *Azorhizobium* sp. RLG2, *Azorhizobium* sp. RLG3, *Rhizobium* sp. RLG4, *Rhizobium* sp. RLG5, *Rhizobium* sp. RLG6, *Azorhizobium* sp. RLG7, *Rhizobium* sp. RLG8, *Azorhizobium* sp. RLG9, *Rhizobium* sp. RLG10, and *Rhizobium* sp. RLG 11 having accession number N.R.R.L. B-50215. In one embodiment at least two of said isolated bacterial strains are provided together in a mixture. In one embodiment at least fourteen of said isolated bacterial strains are provided together in a mixture.

The present invention provides an exemplary mixture of bacterial isolates having accession number N.R.R.L. B-50215.

The present invention provides exemplary isolated fungal strains selected from the group consisting of a *Trichoderma vireni* 3107, *Trichoderma viride* LK, *Trichoderma viride* 3116, *Trichoderma harzianum* 3147, *Trichoderma harzianum* G, *Trichoderma harzianum* LK, and *Trichoderma longibrachiatum* 3108 fungal strain having accession number N.R.R.L. 50216. In one embodiment at least at least two of said isolated fungal strains are provided together in a mixture. In one embodiment at least seven of said isolated fungal strains are provided together in a mixture.

The present invention provides an exemplary mixture of fungal isolates having accession number N.R.R.L. 50216.

The present invention provides exemplary microbial formulation, wherein said formulation consists of a nitrogen fixing bacteria isolate, a phosphate solubilizing microbe isolate, a Rhizobacteria isolate, and a biocontrol microbe isolate. In one embodiment said microbe is selected from the group consisting of a bacteria and a fungus. In one embodiment said biocontrol microbe is selected from the group consisting *Trichoderma viride* 3116, *Trichoderma vixens* 3107, *Trichoderma harzianum* 3147, *Trichoderma harzianum* LK, *Trichoderma harzianum* G, and *Trichoderma longibrachiatum* 3108 having accession number N.R.R.L. 50216. In one embodiment said bacteria isolate is selected from the group consisting of *Ensifer meliloti* FD, *Rhizobium trifolii* FD, *Azorhizobium caulinodans* KN, *Rhizobium* sp. RLG 1, *Azorhizobium* sp. RLG2, *Azorhizobium* sp. RLG3, *Rhizobium* sp. RLG4, *Rhizobium* sp. RLG5, *Rhizobium* sp. RLG6, *Azorhizobium* sp. RLG7, *Rhizobium* sp. RLG8, *Azorhizobium* sp. RLG9, *Rhizobium* sp. RLG10, and *Rhizobium* sp. RLG11 having accession number N.R.R.L. B-50215.

The present invention provides an exemplary microbial formulation, wherein said formulation comprises a mixture selected from the group consisting of a bacterial mixture having accession number N.R.R.L. B-50215 and a fungal mixture having accession number N.R.R.L. 50216.

The present invention provides an exemplary microbial formulation, wherein said formulation is a mixture of bacteria isolates selected from the group consisting of *Ensifer meliloti* FD, *Rhizobium trifolii* FD, *Azorhizobium caulinodans* KN, *Rhizobium* sp. RLG1, *Azorhizobium* sp. RLG2, *Azorhizobium* sp. RLG3, *Rhizobium* sp. RLG4, *Rhizobium* sp. RLG5, *Rhizobium* sp. RLG6, *Azorhizobium* sp. RLG7, *Rhizobium* sp. RLG8, *Azorhizobium* sp. RLG9, *Rhizobium* sp. RLG10, and *Rhizobium* sp. RLG11 having accession number N.R.R.L. B-50215 and a mixture of fungal isolates selected from the group consisting of *Trichoderma virens* 3107, *Trichoderma viride* LK, *Trichoderma viride* 3116, *Trichoderma harzianum* 3147, *Trichoderma harzianum* G, *Trichoderma harzianum* LK, and *Trichoderma longibrachiatum* 3108 fungal strain having accession number N.R.R.L. B-50216. In one embodiment the formulation further comprises, a liquid carrier. In one embodiment said liquid carrier comprises water and humic acid. In one embodiment said humic acid is at a concentration of 12% volume of humic acid (ml)/volume of solution (ml) (v/v). In one embodiment said liquid carrier has a pH of 7.0. In one embodiment said microbial isolate concentration in the liquid carrier ranges from $10^{10}$-$10^{17}$ microbes per milliliter of liquid. In one embodiment the formulation is selected from the group consisting of a liquid, a dried formulation, and a wettable powder.

The present invention provides an exemplary method for enhancing plant growth, comprising, a) providing, i) A microbial formulation, wherein said formulation comprises a mixture selected from the group consisting of a bacterial mixture having accession number N.R.R.L. B-20215 and a fungal mixture having accession number N.R.R.L. B-50216, ii) a plant, and applying said microbial formulation to a plant for enhancing plant productivity. In one embodiment, said microbial formulation further comprises, a liquid carrier and mixing said liquid carrier with said microbial isolate. In one embodiment, said liquid carrier comprises water and humic acid. In one embodiment, said humic acid is at a concentration of 12 percent. In one embodiment, said liquid carrier has a pH of 7.0. In one embodiment, said microbial isolate concentration in the liquid carrier ranges from $10^{10}$-$10^{17}$ microbes per milliliter of liquid formulation. In one embodiment, said applying is selected from the group consisting of seed dipping, pipetting, irrigating, spraying, and foliar spraying. In one embodiment, said plant is selected from the group consisting of a vegetable plant, a legume plant, a cereal plant, a fodder plant, a grass plant, a fiber plant, an oil seed plant, a field pant, a garden plant, a greenhouse plant, and a house plant. In one embodiment, said plant is selected from the group consisting of a tomato, eggplant, okra, squash, zucchini, bean, pea, soybean, rice, corn, sorghum, alfalfa, Bermuda grass, clover, cotton, and peanut. In one embodiment, said enhancing plant productivity is increasing an agriculturally desirable trait. In one embodiment, said method agriculturally desirable trait is selected from the group consisting of seed germination, height of the plant, leaf area, shoot length, root length, legume nodulation, grain yield, fruit yield, shoot weight, root weight, biomass, altered time for flowering, altered time for fruit formation, decreased disease incidence, and increased disease resistance.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 16 shows an exemplary comparison of corn plant biomass from a field trial. F1=Sumagro 1; F2=Sumagro 2; HG & NG=Humagro & Nutragro; and C=control treatments.

DEFINITIONS

Figure 1:
FIG. 1 shows an exemplary preliminary greenhouse experiment demonstrating garden pea plants treated with F1 formulation compared to a control plant (no F1). F1=Sumagro 1.
Figure 2:
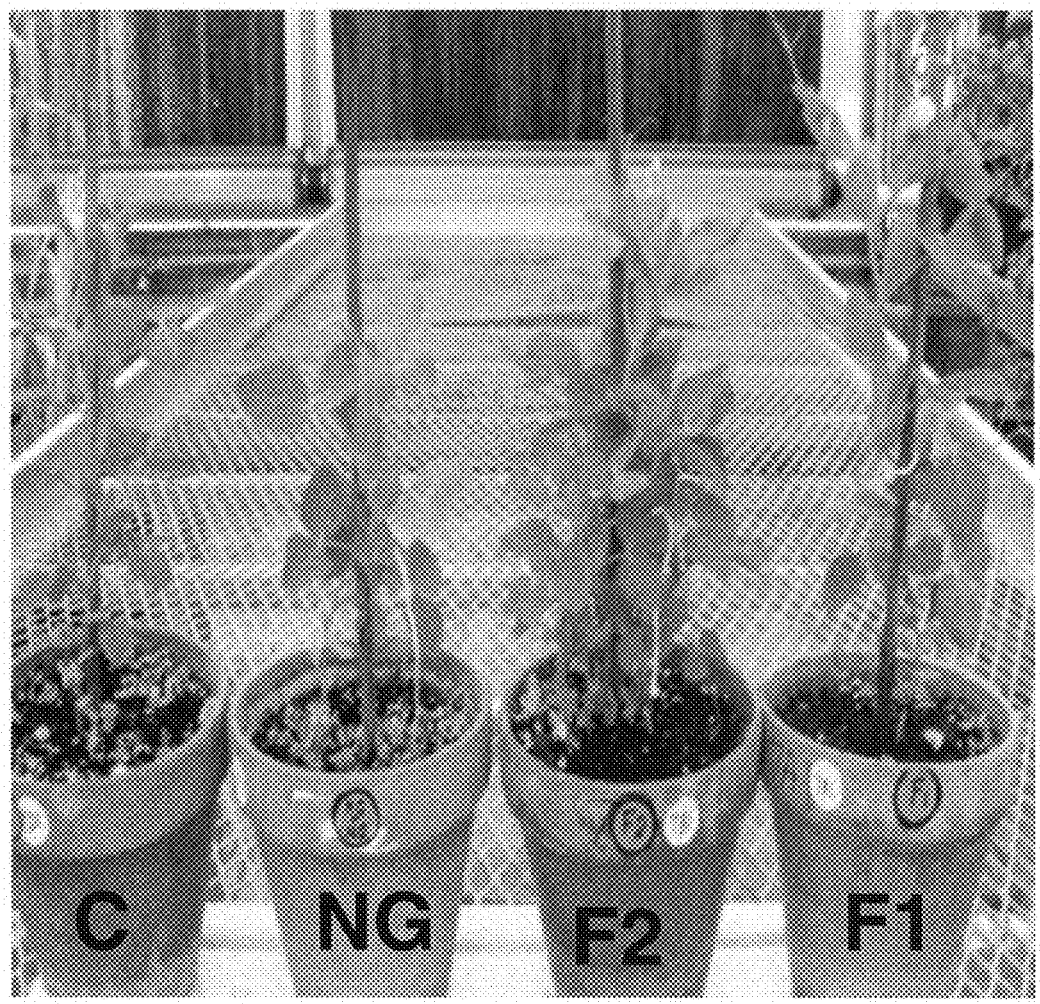
FIG. 2 shows an exemplary greenhouse experiment demonstrating garden pea plants treated with F1=Sumagro 1; F2=Sumagro 2; NG=Nutragro; and C=control treatment (Experiment 1).
Figure 3:
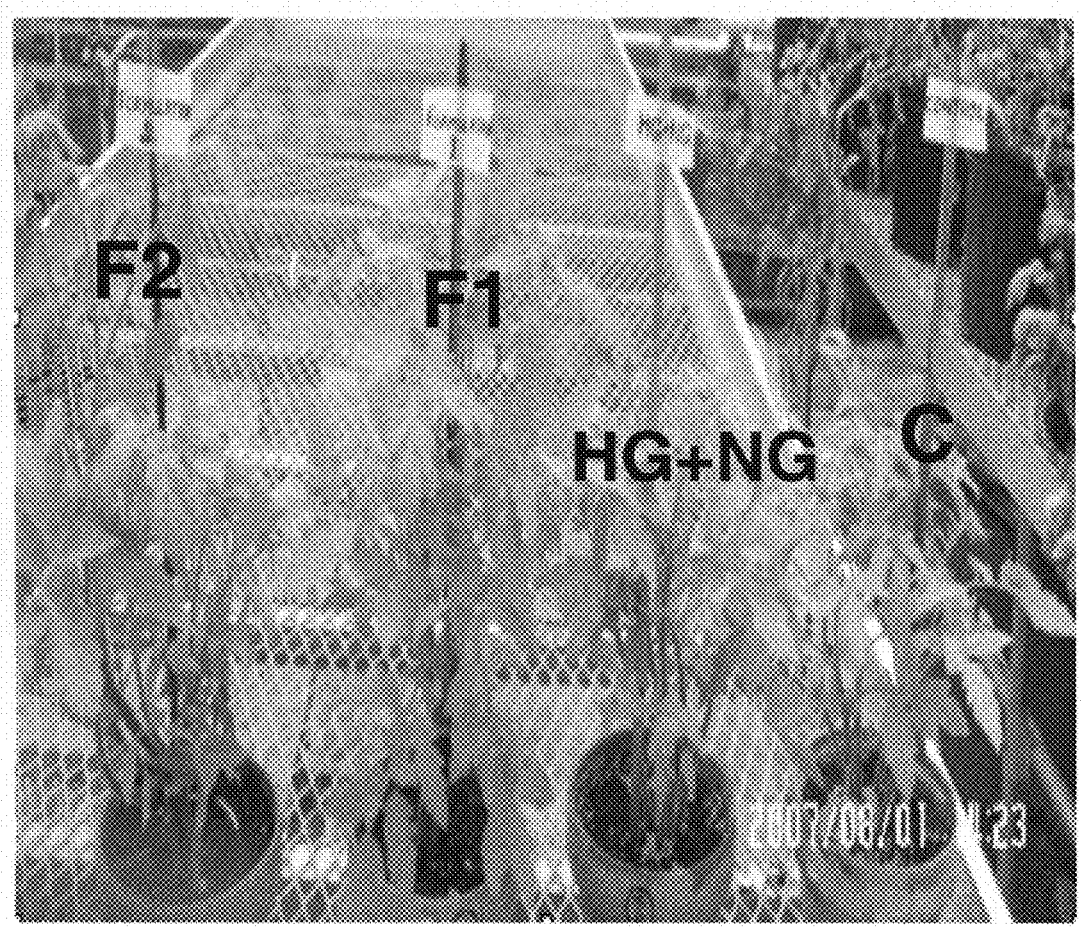
FIG. 3 shows an exemplary greenhouse experiment demonstrating tomato plants treated with F1=Sumagro 1; F2=Sumagro 2; HG & NG=Humagro & Nutragro; and C=control treatment (Experiment 1).
Figure 4:
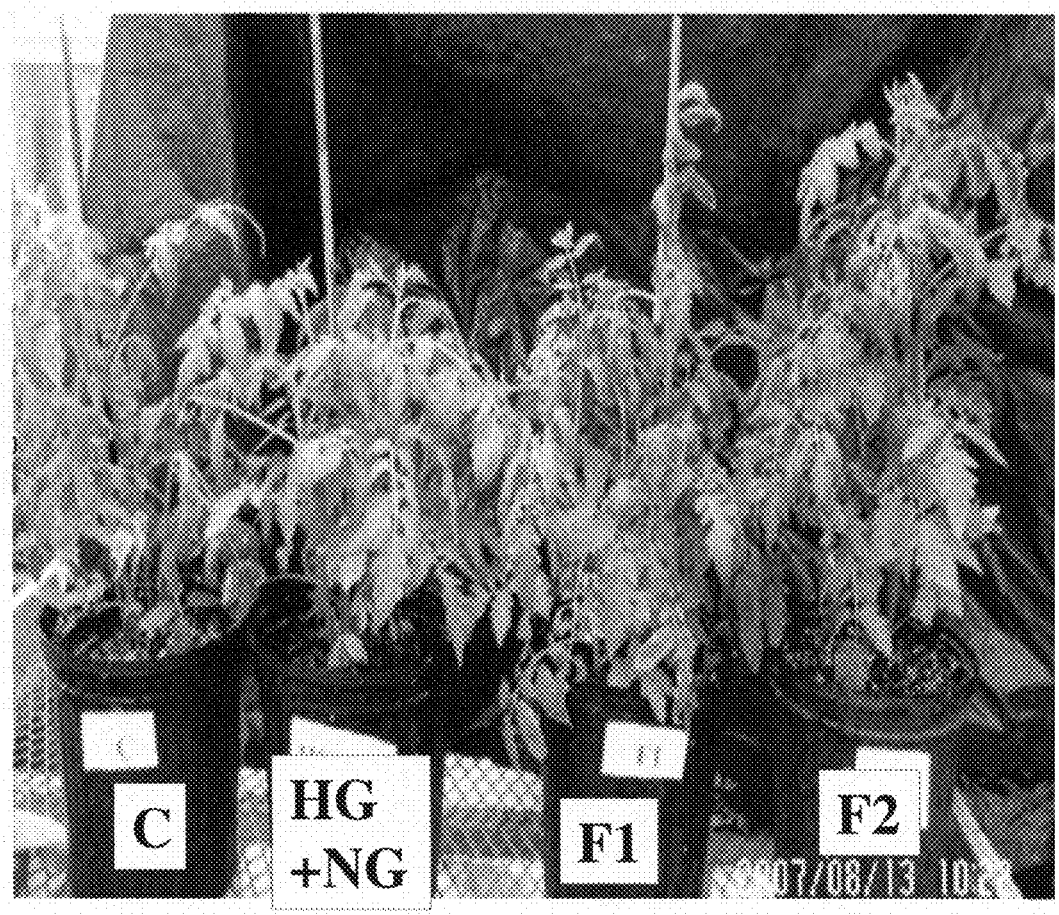
FIG. 4 shows an exemplary greenhouse experiment demonstrating tomato plants, after two months of growth, treated with F1=Sumagro 1; F2=Sumagro 2; HG & NG=Humagro & Nutragro; and C=control treatment (Experiment 1).
Figure 5:
FIG. 5 shows an exemplary greenhouse experiment demonstrating purple hull pea plants treated with F1=Sumagro 1; F2=Sumagro 2; NG=Nutragro; and C=control treatment (Experiment 1).
Figure 6:
FIG. 6 shows an exemplary greenhouse experiment demonstrating soybean plants treated with F1=Sumagro 1; F2=Sumagro 2; NG=Nutragro; and C=control treatment (Experiment 1).
Figure 7:
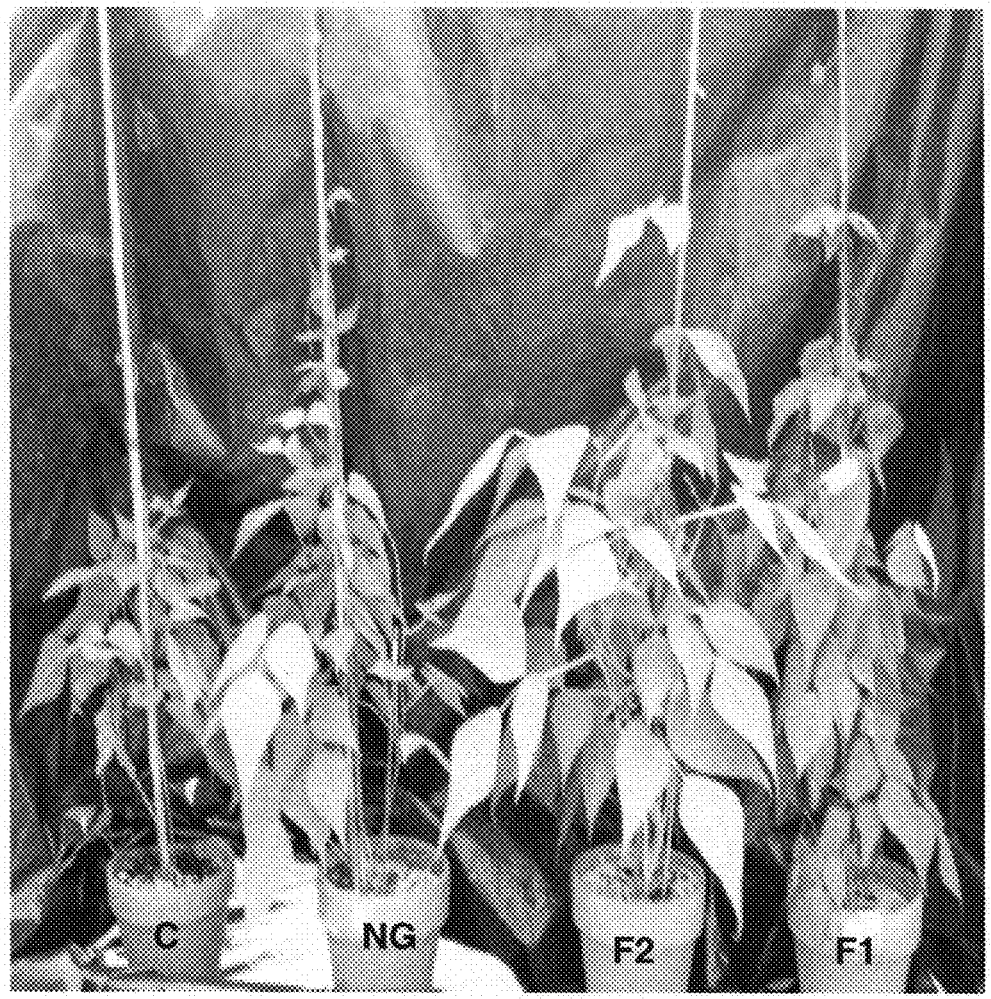
FIG. 7 shows an exemplary greenhouse experiment demonstrating Wonder Bush bean plants treated with F1=Sumagro 1; F2=Sumagro 2; NG=Humagro & Nutragro; and C=control treatment (Experiment 1).
Figure 8:
FIG. 8 shows an exemplary greenhouse experiment using Wonder Bush bean plants treated with F2=Sumagro 2; and NG=Nutragro (Experiment 1).
Figure 9:
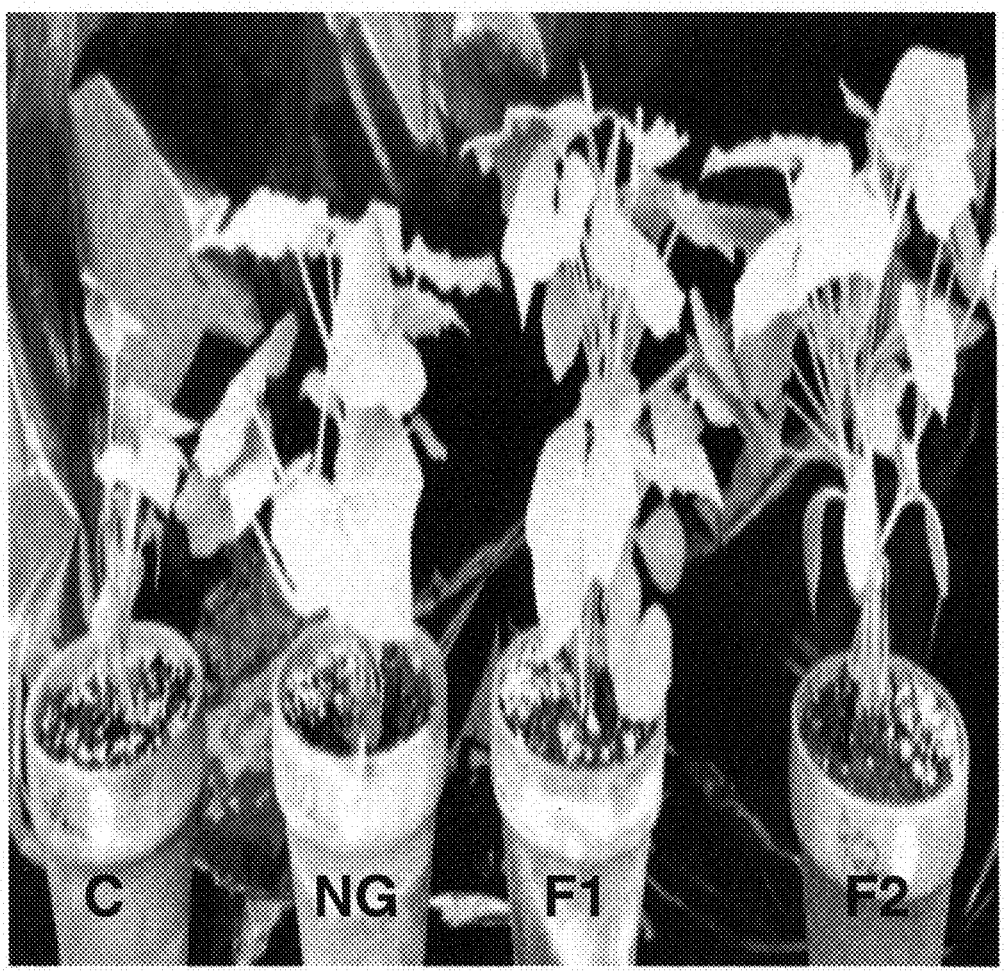
FIG. 9 shows an exemplary greenhouse experiment demonstrating squash plants treated with F1=Sumagro 1; F2=Sumagro 2; NG=Nutragro; and C=control treatment (Experiment 1).
Figure 10:
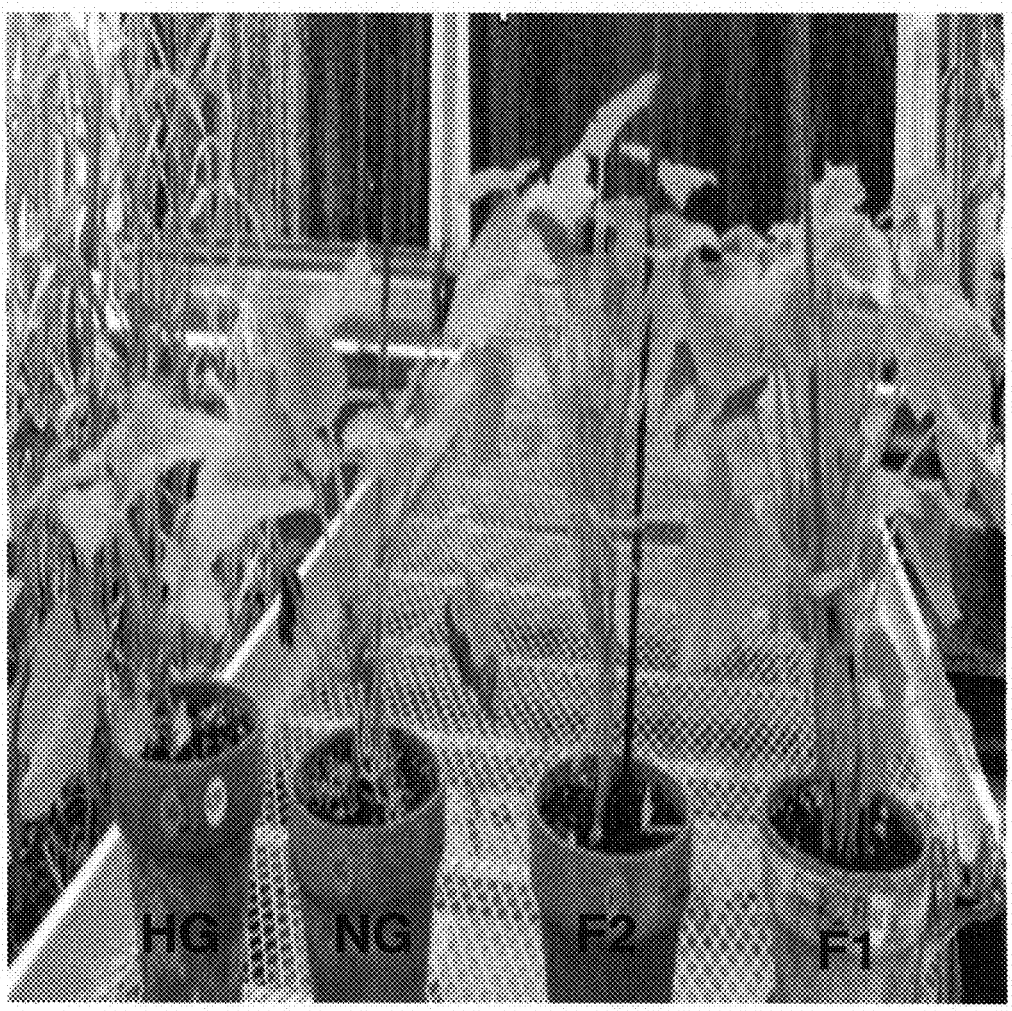
FIG. 10 shows an exemplary greenhouse experiment demonstrating squash plants treated with F1=Sumagro 1; F2=Sumagro 2; NG=Nutragro; and HG Humagro (Experiment 1).
Figure 11:
FIG. 11 shows an exemplary greenhouse experiment demonstrating tomato plants treated with F1=Sumagro 1; F2=Sumagro 2; HG=Humagro; HG & NG=Humagro & Nutragro; and C=control treatment (Experiment 2).
Figure 12:
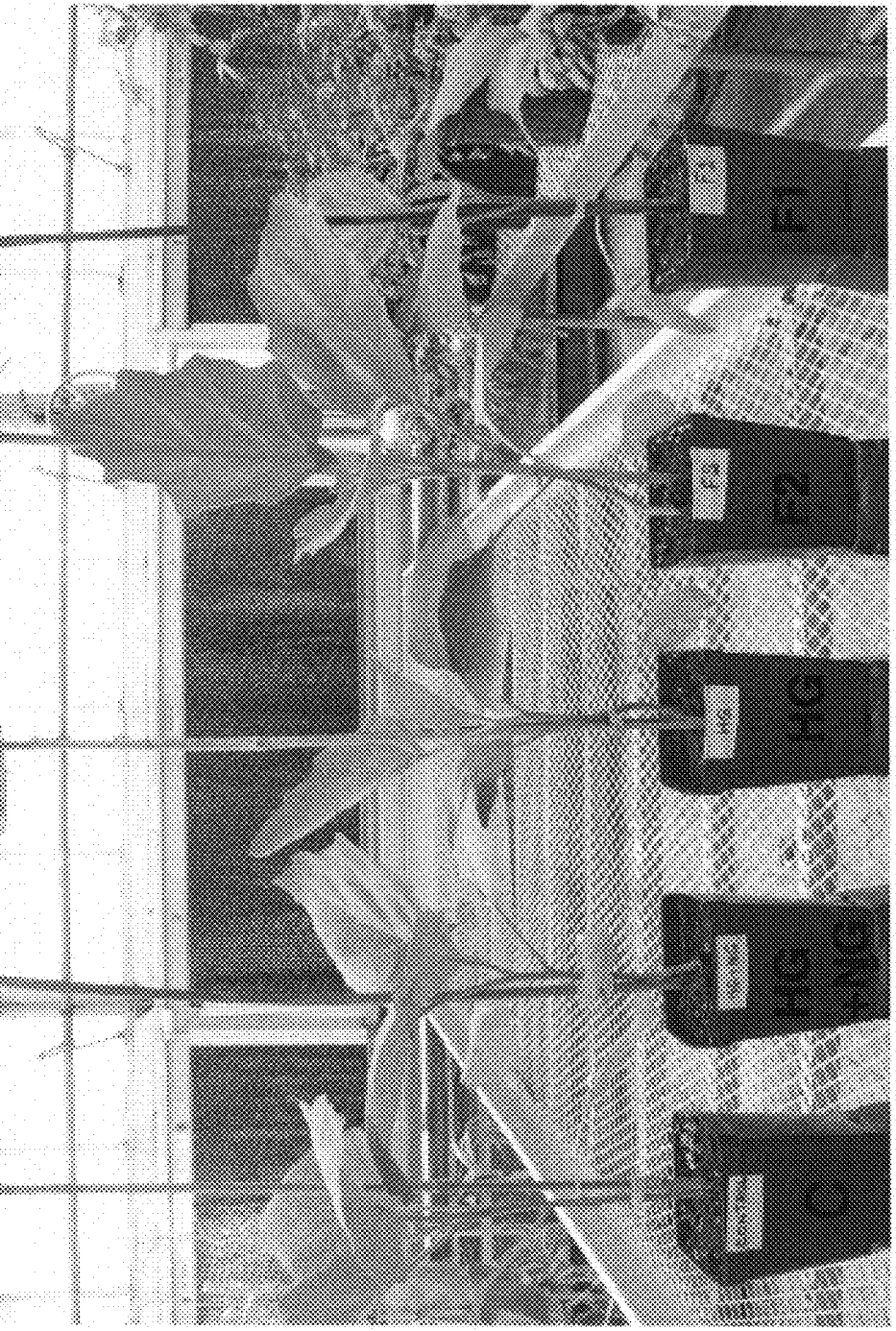
FIG. 12 shows an exemplary greenhouse experiment demonstrating Eggplant (brinjal) plants treated with F1=Sumagro 1; F2=Sumagro 2; HG=Humagro; HG & NG=Humagro & Nutragro; and C=control treatment (Experiment 2).
Figure 13:
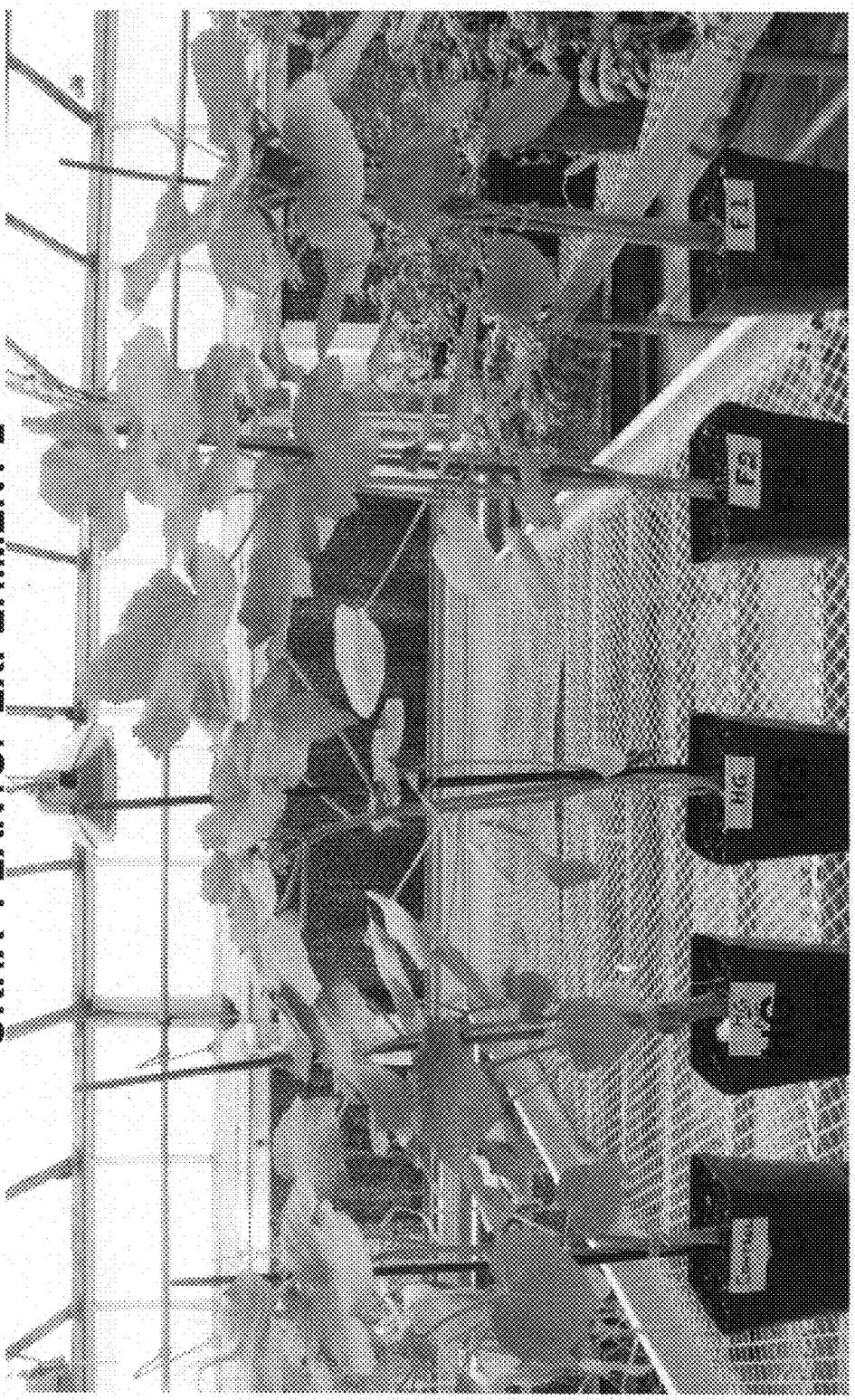
FIG. 13 shows an exemplary greenhouse experiment demonstrating okra plants treated with F1=Sumagro 1; F2=Sumagro 2; HG=Humagro; HG & NG=Humagro & Nutragro; and C=control treatment (Experiment 2).
Figure 14:
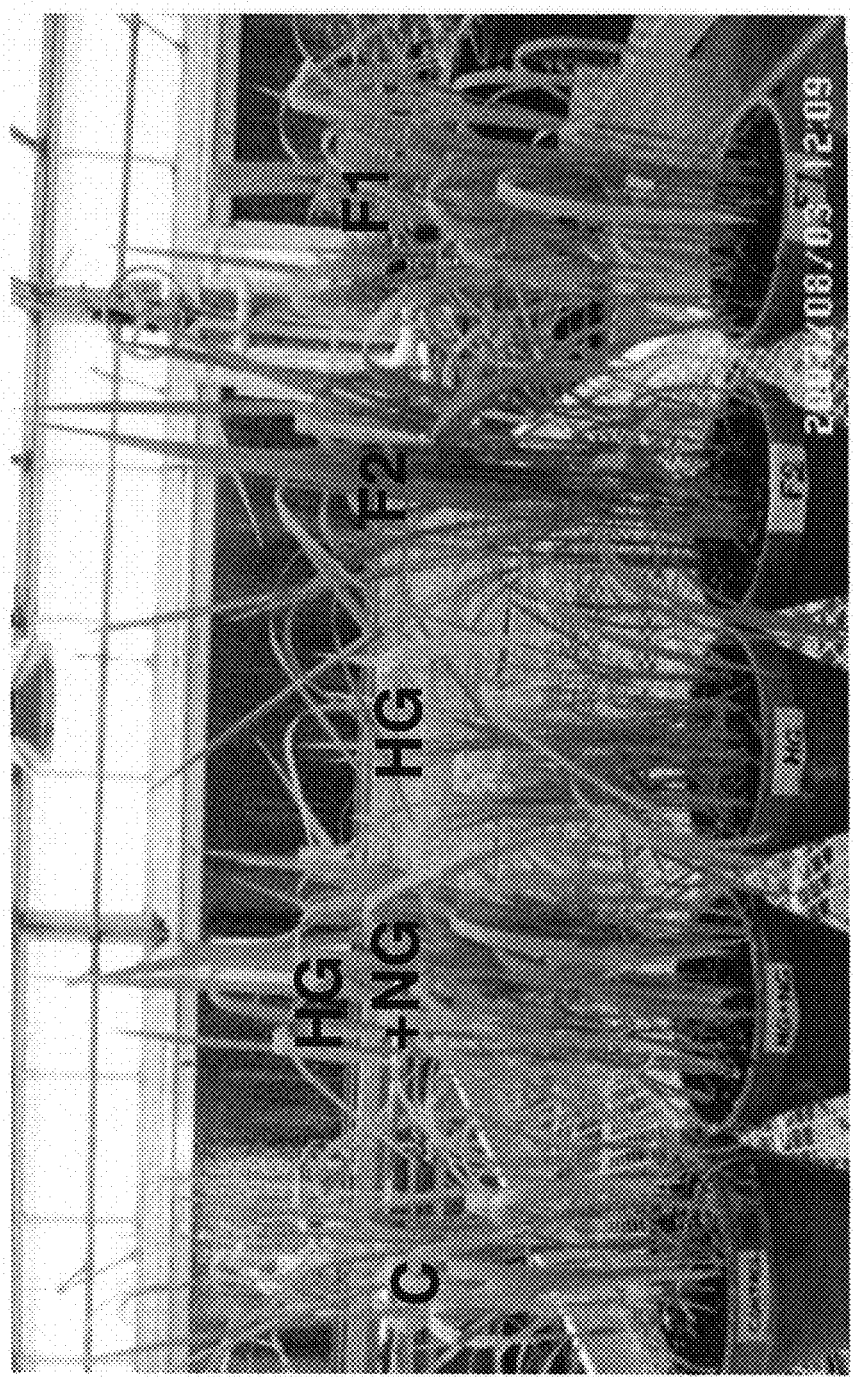
FIG. 14 shows an exemplary greenhouse experiment demonstrating rice plants treated with F1=Sumagro 1; F2=Sumagro 2; HG=Humagro; HG & NG=Humagro & Nutragro; and C=control treatment (Experiment 2).

To facilitate an understanding of the present invention, a number of terms and phrases as used herein are defined below:

The use of the article "a" or "an" is intended to include one or more.

As used herein, terms defined in the singular are intended to include those terms defined in the plural and vice versa.

As used herein, "formulation" in reference to a composition of the present invention refers to a product, wherein "formulating" is the process of using a formula, such as a recipe, for a product, i.e. the ingredients, the quantities ingredients that were or would be added, the sequence of adding an ingredient, and the processing steps that were or will be taken to provide the product. A formulation may be in any form, such as a liquid, solid, i.e. dried formulation, wettable powder, and in some embodiments, applied with a carrier.

As used herein, the term "applying" in reference to a formulation of the present invention refers to any means for treating seeds, soil, and plants with formulations of the present inventions, for example, seed dipping, soil drench, pipetting onto soil, pipetting onto plants, irrigating plants with liquids comprising formulations of the present inventions, spraying formulations of the present inventions, i.e. foliar spraying, and the like. "Applying to a plant" refers to any means for treating a plant with a formulation of the present inventions, for example, adding the formulation to the soil at any time prior to, in combination with, or after planting anyone of a seed, seedling, or growing plant.

As used herein, the term "seed dipping" refers to application of a formulation of the present invention directly to a seed, such as soaking a seed for few seconds, minutes, or hours in a liquid formulation of the present inventions. Seed dipping may also refer to application of a dried microbial formulation of the present inventions.

As used herein, the term "soil drench" refers a to applying a liquid to soil.

As used herein, "carrier" in reference to formulations of the present inventions, refers to a substance, either synthetic or natural, for transporting an active ingredient, such as a microbe of the present inventions, onto a plant, a seed, soil, etc, examples of a carrier include, humic acid, a mineral, a botanical, and the like.

As used herein, "agent" in reference to an ingredient of a formulation of the present inventions, refers to a substance that causes a change, such as a chemical agent or a substance that protects an active ingredient of a formulation, for example, an ultraviolet light resistant agent, etc.

As used herein, "dispersing agent" refers to a material that will cause microcapsules or particles to separate uniformly throughout a solid, liquid, or gas. Alternatively, a "dispersing agent" refers to a material that will cause a dispersion of microbes, microcapsules or particles into the environment, for example, a dispersing agent will allow an active ingredient to be dispelled from a microcapsule, a dispersing agent will allow an active ingredient to be dispersed into the environment.

As used herein, "inert" in reference to an ingredient of the formulations of the present inventions, refers to a material that is not readily reactive with other materials, such as ingredients or host or environmental materials, such that an inert ingredient forms few or no chemical compounds.

As used herein, "fill material" in reference to an agent or an ingredient of the present inventions, refers to a substance for "filling" in the spaces of a capsule of the present inventions, such that the active ingredient may be referred to as a fill material in addition to any fill material desired for incorporation in a formulation of the present inventions, for example, gelatin, hydrogel, etc. A fill material may be inert, may comprise a controlled release agent, may be a releasable fill material, and may be an active agent, and a combination thereof, in the formulations of the present inventions.

As used herein, the term "stabilizer" refers to a substance capable of imparting resistance against physical or chemical deterioration or decomposition, for example, a fill material or fill stabilizer and a shell stabilizer, see, as an example, United States Patent Application No. 20030202999, herein incorporated by reference in its entirety.

As used herein, "agronomically acceptable salts" refers to mineral salts that do not induce negative effects on agricultural crops when used properly. They include, metal salts such as sodium, potassium, calcium and magnesium salts, ammonium salts such as isopropyl ammonium salts and trialkylsulfonium salts such as triethylsulfonium salts.

As used herein, "phytohormones" refers to a plant hormone including any of the hormones produced naturally in plants and that are active in minute amounts in controlling growth and other functions at a site remote from the place of production. The three principal types are auxins, cytokinins and gibberellins.

As used herein, the term "plant" is used in its broadest sense. It includes, but is not limited to, any species of grass (e.g. turf grass), sedge, rush, ornamental or decorative, crop or cereal, fodder or forage, fruit or vegetable, fruit plant or vegetable plant, woody, flower or tree. It is not meant to limit a plant to any particular structure. Such structures include, but are not limited to, stomata, a seed, a tiller, a sprig, a stolon, a plug, a rhizome, a shoot, a stem, a leaf, a flower petal, a fruit, etc.

As used herein, the terms "crop" and "crop plant" are used herein its broadest sense. The term includes, but is not limited to, any species of plant or alga edible by humans or used as a feed for animals or fish or marine animals, or consumed by humans, or used by humans, or viewed by humans (flowers) or any plant or alga used in industry or commerce or education, such as vegetable crop plants, fruit crop plants, fodder crop plants, fiber crop plants, and turf grass plants.

As used herein, the terms "leaf" and "leaves" refer to a usually flat, green structure of a plant where photosynthesis and transpiration take place and attached to a stem or branch.

As used herein, "stem" refers to a main ascending axis of a plant.

As used herein, "seed" refers to a ripened ovule, consisting of the embryo and a casing.

As used herein, "pathogen" refers a biological agent that causes a disease state (e.g., infection, anthracnose, etc.) in a host. "Pathogens" include, but are not limited to, viruses, bacteria, archaea, fungi, protozoans, mycoplasma, parasitic organisms and insects.

As used herein, the terms "bacteria" and "bacterium" refer to all prokaryotic organisms, including those within all of the phyla in the Kingdom Prokaryotae. It is intended that the term encompasses all microorganisms considered to be bacteria, including *Azotobacter, Azospirillum, Azorhizobium, Pseudomonas, Bacillus, Rhizobium, Mycoplasma*, et cetera. All forms of bacteria are included within this definition including cocci, bacilli, spirochetes, spirilla, vibrios, spheroplasts, protoplasts, etc. Also included within this term are prokaryotic organisms that are gram negative or gram positive. "Gram negative" and "gram positive" refer to staining patterns with the Gram-staining process that is well known in the art. (See, e.g., Beveridge, 2007, Sampling and staining for light microscopy, pages 19-33. In C. A. Reddy, T. J. Beveridge, J. A. Breznak, G. A. Marzluf, T. M. Schmidt, and L. R. Snyder (eds.). Methods for General and Molecular Microbiology, Am. Soc. Microbiol., Washington, District of Columbia. "Gram positive bacteria" are bacteria which retain the primary dye used in the Gram stain, causing the stained cells to appear dark blue to purple under the microscope. "Gram negative bacteria" do not retain the primary dye (crystal violet) used in the Gram stain, but are stained red by the counter stain (safranin). Thus, Gram negative bacteria appear red.

As used herein, "microorganism" refers to any species or type of microorganism, including but not limited to, bacteria, archaea, fungi, protozoans, mycoplasma, and parasitic organisms.

As used herein, "fungi" is used in reference to eukaryotic organisms such as the molds and yeasts, including dimorphic fungi, fungi found in soil, and any fungi found growing on a plant.

As used herein, "cfu" refers to a colony forming unit.

As used herein, "enhancement" refers to increasing a characteristic, such as growth, grain yield.

As used herein, "fertilizer" refers to any organic material or inorganic material of natural or synthetic origin which is added to soil to provide nutrients, including all three elements of nitrogen, phosphorus, and potassium, necessary to sustain plant growth.

As used herein, "humic molecule" as used herein means a carbon molecule with open and available hydrogen and oxygen bonding sites and exchange capacity.

As used herein, "humate-based" refers to include but are not limited to sugars (including glucose, fructose, and molasses), plasma, manure tea (for example, colored water that manure has been steeped in), peat extracts, compost extracts, coal extracts, leonardite extracts, kelp or extracts thereof, and other humic matrices known in the art that contain humic molecules that are rich in macronutrients, nitrogen, phosphorus and/or potassium. The matrix may also contain growth-stimulating compounds such as a blend of botanic/carbohydrates, growth factors, amino acids and micro-nutrients including calcium, boron, copper, molybdemum, manganese, magnesium, iron, sulfur and zinc as needed.

As used herein, "herbicide" refers to any substance, either synthetic or natural, used to kill a plant or inhibit plant growth. Typically an herbicide is intended to kill a weed while leaving the desired plant, such as a crop plant, alive.

As used herein, the term "weed" refers to any plant a plant grower, such as a farmer, landscaper, and the like, would like to eliminate that is growing in a container, such as a pot, or in a field, for example, a weed is a grass plant growing in a beet field.

As used herein, "pesticide" or "biocide" refers to a substance or mixture of substances intended for destroying, killing, repelling, mitigating the life of any pest. Pests can be insects, mice and other animals, unwanted plants (weeds), fungi, algae, or microorganisms like bacteria and viruses. The term pesticide also applies to herbicides, fungicides, and various other substances used to control pests.

As used herein, "pest" refers to a living organism that occur where they are not wanted or that cause damage to crops or humans or other animals, examples include insects; mice and other animals; unwanted plants (such as weeds); fungi; algae, and microorganisms such as bacteria and viruses.

As used herein, "plant growth regulator" or "PGR" refer to a chemical that affects plant growth and/or development.

As used herein, "diverse" refers to a group of different microbes, such as a group comprising a gram+bacterium, gram−bacterium, a motile microbe, a nonmotile microbe, a root nodule microbe, a soil microbe, a rhizosphere microbe, a fungus, and the like.

As used herein, "multifunctional" in reference to a formulation refers to a formulation providing at least 2 functions, for example, a healthy plant, a net result healthy plants, nutrients, higher productivity, faster growth, then microbes also synergistic effects.

As used herein, "functionality" refers to increasing plant growth productivity, inducing pest resistance, nutrient cycling.

As used herein, "broad spectrum" in reference to beneficial results refers to benefits to a combination of leguminous and nonleguminous, vegetable crops and other plants and described herein.

As used herein, "broad spectrum" in reference to plants refers to any type of plant.

As used herein, "safe" in reference to environmental activity refers to a condition of exposure under which there is a practical certainty that no harm will result to the ecosystem, such a the surrounding ground, air, and water, including ground water, surface water, drainage water and any bodies of water into where drainage water flow.

As used herein, "ecological impact" refers to an effect that a man-caused or natural activity has on living organisms and their non-living (abiotic) environment.

As used herein, "ecological sustainability" or "environmental sustainability" refers to current methods of ecosystem maintenance, including components and functions, in order to provide safe and healthy ecosystems for future generations of plants, fish, reptiles, mammals, and microbial communities.

As used herein, "ecology" refers to a relationship of living things to one another and their environment, or the study of such relationships.

As used herein, "ecosystem" refers to an interacting system of a biological community, including but not limited to plants, fish, reptiles, mammals, and microbial communities, and its non-living environmental surroundings, such as soil, water, and air.

As used herein, "road" refers to any highway, road, street, avenue, lane, private way, and similarly paved, gravel or dirt thoroughfare for any type of vehicle, airplane, train, bicycle, animal and human.

As used herein, "tilth" in reference to soil refers to a physical condition of the soil as related to tillage, seedbed preparation, seedling emergence, and root penetration.

As used herein, "NRRL" or "N.R.R.L." in reference to a biological depository for microorganisms recognized under the Budapest Treaty, refers to the "Agricultural Research Service Culture Collection (ARS) National Center for Agricultural Utilization Research, in Peoria, Ill. United States of America."

As used herein, "accession number" in reference to "having an accession number" refers to a number assigned to a cultured isolate upon deposition to a recognized depository of patent strains, for example, *Paenibacillus peoriae*, strain NRRL BD-62, where BD-62 is an accession number.

As used herein, "isolate" refers to a pure microbial culture separated from its natural origin, such an isolate obtained by culturing a single microbial colony. In other words, an isolated bacterial strain, for example, an *Ensifer meliloti* FD, *Rhizobium trifolii* FD, *Azorhizobium caulinodans* KN, *Rhizobium* sp. RLG1, *Azorhizobium* sp. RLG2, *Azorhizobium* sp. RLG3, *Rhizobium* sp. RLG4, *Rhizobium* sp. RLG5, *Rhizobium* sp. RLG6, *Azorhizobium* sp. RLG7, *Rhizobium* sp. RLG8, *Azorhizobium* sp. RLG9, *Rhizobium* sp. RLG10, *Rhizobium* sp. RLG11, etc. and an isolated fungal strain, for example, *Trichoderma viride* 3116, *Trichoderma virens* 3107, *Trichoderma harzianum* 3147, *Trichoderma harzianum* LK, *Trichoderma harzianum* G, *Trichoderma longibrachiatum* 3108, etc.

As used herein, "mixture" refers to a combination of two or more substances that are not chemically united. Mixtures may be natural mixtures and man-made mixtures, such as mixtures of the present inventions, for example, a mixture of microbial isolates. A mixture may be physically separated into individual substance, such as in the present inventions wherein a microbial isolate may be re-isolated from a mixture of isolates.

As used herein, "enhancing plant productivity" refers to any aspect of a plant altered for a "desired benefit," such as increasing an agriculturally desirable trait. "Desired benefit" also refers to any effect on a plant to confer a benefit to humans and animals, As used herein, "agriculturally desirable trait" refers to any qualitative and quantitative agricultural trait, such as crop yield, biomass, resistance to pathogens, resistance to pests, resistance to environmental changes, for example, drought, etc. In other words, a desirable trait is any characteristic worth obtaining.

GENERAL DESCRIPTION

The present invention relates to eco-friendly compositions and methods for providing plant growth enhancing formulations comprising mixtures of microbial isolates. In particular, numerous bacterial and fungal strains were isolated from a variety of soil types, from rhizospheres and from root nodules of leguminous plants, in designed combinations, for providing plant growth and plant productivity enhancing formulations. These specifically designed polymicrobial formulations would further provide protection against plant pathogens lowering the need for nitrogen containing fertilizers, solubilize minerals, protect plants against pathogens, and make available to the plant valuable nutrients, such as phosphate, thus reducing and eliminating the need for using chemical pesticides and chemical fertilizers. Thus it would greatly enhance the environment to use polymicrobial-derived products, for increasing plant growth and productivity and for reducing the need nitrogen fertilizers and pesticides.

The inventors contemplate numerous advantages of using polymicrobial formulations of the present inventions. In particular, unlike other formulations, the inventors specifically designed new formulations for enhancing plant growth and productivity by specifically choosing combinations of microbes demonstrating specific microbial traits. The benefits conferred by these formulations include symbiotic and non-symbiotic nitrogen fixation, suppression of disease causing organism and induction of systemic resistance in plants, helping enhance nutrient uptake by solubilizing plant nutrients such as phosphorous, production of plant hormones and micronutrients that stimulate growth and productivity and better tolerance to environmental stress.

In addition to formulations providing at least one benefit to plants, such as a biofertilizer, for protection against plant pathogens (biocontrol), growth nutrients, etc., the inventors also provided one formulation for providing at least 4 specific types of benefits to plants: nitrogen fixation (legume and nonlegume); biocontrol of plant pathogens, phosphate solubilization; and plant growth promoter substances. In other words, certain formulations of the present inventions provided a combination of biofertilizer, biocontrol, and plant growth promoter substances. These four basic benefits are provided by a combination of microbes where nutrients are provided directly to the plants by the microorganisms or indirectly by providing benefits to plants by inducing endogenous microbial communities to provide benefits, such as growth and productivity. Thus, unlike the microbial formulations currently available, the inventors contemplated a polymicrobial formulation comprising at least four groups of organisms; nitrogen fixing (including both symbiotic and nonsymbiotic nitrogen fixation microbes), biocontrol microbes (bacteria and fungal), Phosphorus Solubilizing Microorganisms (PSM), and Plant Growth Promoting Rhizobacteria (PGPR) for providing plant growth promoter substances. Further, the inventor included microbes with additional capabilities, for example, microbes for inducing nodule formation in roots.

Therefore, inventors designed specific polymicrobial formulations for providing multiple benefits to plants and their crops by combining traits of specific microbes. These polymicrobial formulations were designed to provide a specific combination of benefits to plants, humans and their environment. These combined benefits are not found in individual microbial isolates used as inoculums. Examples of traits from individual microbe Genus or species for providing specific benefits to plants.

During the course of development and testing of the present inventions in field trials, the inventors found that using formulations of the present inventions, in particular Sumagro-2, the amount of traditional chemical fertilizer application was reduced at least 50% while retaining desired agricultural traits. In Greenhouse trials the formulations were primarily used without chemical or artificial fertilizer or other type of chemical supplementation. Thus the inventors' contemplate the use of these formulations in combination with traditional chemical use where the amount of traditional chemical application is substantially reduced. In one embodiment, the use of chemicals is reduced at least 25%. In another embodiment the use of chemicals is reduced at least 30%. In another embodiment the use of chemicals is reduced at least 40%. In another embodiment the use of chemicals is reduced at least 50%. In another embodiment the use of chemicals is reduced at least 60%. In another embodiment the use of chemicals is reduced at least 75%. In another embodiment the use of chemicals is reduced at least 80%. In another embodiment the use of chemicals is reduced at least 90%. In a preferred embodiment, the use of formulations of the present inventions completely replaces the use of chemical treatments in the home, greenhouse and field.

Even further, the inventors contemplated formulations of the present inventions such that one formulation would provide at least four benefits listed above and would also provide benefits to a broad spectrum of plants, including but not limited to legumes and nonlegumes, cereals and grains, vegetables and fruits, fiber producing plants and grass plants. The inventors' further contemplate the use of the formulations on additional types of plants including but not limited to trees. These formulations would provide benefits that include but not limited to agricultural traits, such as increasing crop yield and biomass. The inventors further contemplate the use of their formulations as prophylactic treatments for biocontrol of pathogens, including bacteria, fungus, nematodes and insects.

Soil microbial populations often contribute to the growth and health of plants including but not limited to crop plants, landscaping plants, garden plants, greenhouse plants, indoor plants, et cetera. Microbes within these populations perform a variety of functions, such as converting atmospheric nitrogen, which plants cannot use, into ammonia or other useful nitrogenous compounds that many plants can use. For example, nitrogen conversion (wherein "conversion" is also referred to as "fixation") takes place in small nodules on the roots of legumes, such as pea plants, bean plants, soybean plants, clover plant plants, et cetera. Thus in one embodiment, the inventors contemplated isolating microbes for increasing nitrogen fixation in plants. In one embodiment, the inventors contemplated using microbes for increasing nitrogen fixation. In one embodiment, the inventors contemplated using microbial mixtures for increasing legume nodule formation. In a further embodiment, the inventors contemplated using microbial mixtures for inducing legume nodule formation. In some embodiments, the inventors contemplated the isolation and use of Plant Growth Promoting Rhizobacteria (PGPR), which are generally root-colonizing bacteria.

Microbes also oxidize chemicals and assist plants in absorbing nutrients and trace elements, such as phosphates, iron, cobalt, manganese, and molybdenum, from soil in addition to decomposing plant and animal organic matter into simpler organic products that plants can absorb and use to sustain their growth. In particular, cultivatable soil is frequently alkaline in nature containing calcium or magnesium with little available phosphorus. Due to a typically higher concentration of calcium, whenever phosphatic fertilizers are applied in such soil, a large quantity of applied phosphate gets fixed as Tri-Calcium Phosphate which is water insoluble and hence becomes unavailable to the plant. Conversely, when soil is acidic, iron or aluminum salts will form with applied phosphate containing fertilizers. Fortunately, certain soil microorganisms have inherent capacity to dissolve part of the fixed phosphorus (salts) and make it available to the crop by secreting certain organic acids. These types of organisms are called Phosphorus Solubilizing Microorganisms (PSM). Soil bacteria and fungi comprise the greatest percentages of phosphate Solubilizing microorganisms, known as PSM or Phosphate Solubilizing Bacteria (PSB) and Phosphate Solubilizing Fungi (PSF). These microorganisms are capable of Solubilizing insoluble compounds and release phosphorus to soil solution. Soil microbes further assist in forming and maintaining arable soils rich in complex organic materials through which roots easily grow and absorb water and nutrients.

Thus the inventors also contemplated the isolation of microbes for enhancing plant growth and productivity, in particular bacteria, for oxidizing chemicals and assisting plants to increase absorption of nutrients and trace elements.

However microbial populations and individual microbe species may also be detrimental to plant health. Deleterious rhizobacteria (DRB) are predominantly saprophytic bacteria that aggressively colonize plant seeds, roots and rhizospheres and readily metabolize organic substances released by plant tissues. Numerous types of plant diseases, below and aboveground, are caused by both individual species and groups of bacteria found in the soil. Furthermore, harmful molds and other soil fungi are responsible for many serious root diseases and above-ground diseases of plants. Thus, major economic crops frequently are damaged by soil-borne fungi and bacteria, for example, root rots, collar rots, wilts, seed decay, seedling blights, fruit rots, root browning, damping-off, etc., take a heavy economic toll each year. Many of these plant diseases caused by soil-borne plant pathogens (where pathogens refer to any disease-causing organism) are difficult to control by conventional procedures, for example, by using synthetic chemical pesticides.

Even further, the inventors further contemplate isolating and using microbial isolates and mixtures of isolates for biocontrol of phytopathogenic organisms. Biocontrol agents are also useful in a method of enhancing plant growth that involves applying them to plants, plants seeds, or soil surrounding plants under conditions effective to enhance growth in the plants or plants produced from the plant seeds. Even further, the formulations are contemplated for use in insect biocontrol treatments and programs.

Numerous attempts have been made by others to provide microbial-based products for beneficial plant growth, however few, if any, effective commercially viable products are available. The lack of highly effective microbial based products is not consistent with the numerous publications showing that plant growth can sometimes be affected beneficially when inoculated with one specific isolated microbial species, such as a bacteria or fungi, for example, a *Pseudomonas fluorescens* NBRI 1303 (ATCC 55939) isolate was shown to be effective in suppressing plant pathogens, including *Fusarium oxysporum* f. sp. *ciceri, Rhizoctonia bataticola* and *Pythium* sp. in chickpeas (U.S. Pat. No. 6,495,362; herein incorporated by reference) while other bacteria were disclosed as single bacterium isolates (for example, U.S. Pat. No. 6,896,883; herein incorporated by reference), in addition to combinations of multiple strains from one Genus, (for example, U.S. Pat. No. 6,194,193; herein incorporated by reference) and multiple microbes (for example, Publication Number: WO/2005/077861; herein incorporated by reference). However none of these publications show a single formulations providing the multiple benefits for a broad spectrum of crops as described for formulations of the present inventions.

Other microbes for providing disease resistance were also reported, (for example, U.S. Pat. No. 6,495,362, U.S. Pat. No. 6,280,719; herein incorporated by reference). A *T. harzianum* T22 fungal strain was reported to enhance root development from field-grown corn and soybean plants and improve survival of pepper plants ((*Trichoderma* spp., including *T. harzianum, T. viride, T. koningii, T. hamatum* and other spp. Deuteromycetes, Moniliales (asexual classification system) (Harman, Cornell Community Conference on Biological Control, Apr. 11-13, 1996; www.nysaes.cornell.edu/ent/biocontrol/pathogens/*trichoderma*.html; herein incorporated by reference) in addition to findings that "Seed treatment with *Trichoderma harzianum* strain T22, which results in colonization of plant roots but little or no colonization of shoots or leaves, had substantial effects on growth of and disease expression in maize inbred line Mo17. Shoots and roots of 10-day-old seedlings grown in a sandy loam field soil were larger (roots were nearly twice as long) in the presence of T22 than in its absence . . . . Plants grown from T22-treated seed had reduced symptoms of anthracnose following inoculation of leaves with *Colletotrichum graminicola*, which indicates that root colonization by T22 induces systemic resistance in maize." (Harman, et al., The American Phytopathological Society, Vol. 94, No. 2, 2004, 147-153, herein incorporated by reference). Further, "specific strains of fungi in the genus *Trichoderma* (*T.*) colonize and penetrate plant root tissues and initiate a series of morphological and biochemical changes in the plant, considered to be part of the plant defense response, which in the end leads to induced systemic resistance (ISR) in the entire plant. The capability of *T. harzianum* to promote increased growth response was verified both in greenhouse experiments and in the hydroponic system." (Chet, et al., Plant Biocontrol by *Trichoderma* spp., Weizmann Institute, www.weizmann.ac.il/Biological_Chemistry/scientist/Chet/Chet.html, Last updated Jan. 19, 2006; herein incorporated by reference). However, this last reference fails to refer to the strain used or type of plant demonstrating these effects. Further, formulations of these microbial strains would not provide the range of benefits of the polymicrobial formulations of the present inventions for a wide range of crops.

In spite of much published information on the benefit of individual microbes to plants (Ilungo et al 2004), there are relatively few efficacious microbial inoculant products capable of conferring all the beneficial effects on crop productivity (Actinovater series, Hort Enterprises, Mitcom Consultancy, Nitagen, Inc., Nutragro, and Tandje Enterprises). More importantly, developing microbial formulations contain a range of microorganisms isolated from divers rhizosphere environments and possessing divers functional abilities and be able to enhance production of a broad spectrum of plants has been a real challenge. Many potentially useful bacteria never appear on the commercial market, which may be due to inappropriate designing of the formulation, lack of efficacy under field conditions, or lack of stability of the product. Development of a successful microbial inoculant involves several critical elements such as strain selection, selection of a carrier, mass multiplication (division and growth) appropriate construction of the formulation, and packaging and marketing.

However, merely because one strain of microbe may be beneficial to a plant, does not mean that another strain, even of the same species, will provide equal benefits, (for example, out of 17 rhizobacteria isolates, one *Bacillus* spp. out preformed the others for providing benefits to wheat plants, see, Hafeez, et al., (2006) "Plant growth-promoting bacteria as biofertilizer," Agron. Sustain. Dev. 26:143-150. [abstract only]; herein incorporated by reference). In fact isolated strains within the same species may show opposite effects when used to treat a plant. One example of such dichotomy is shown by some *Serratia* (*S.*) strains, such as *S. proteamaculans* 1-102 and *S. liquefaciens* 2-68, that have beneficial effects on legume plant growth (Chanway et al., 1989, Soil Biology and Biochemistry 21:511-517; Zhang et al., 1996, Plant and Soil 179:33-241; Bai, et al., 2002, Journal of Experimental Botany, 53(373):1495-1502; all of which are herein incorporated by reference). While other *Serratia* strains, such as a *Serratia plymuthica* strain A153, may actually inhibit plant growth where it showed strong growth-suppressing activities against a range of broad-leaved weeds after foliar spraying (for example, see, Weissmann, et al., 2003, BioControl, 48(6); 725-742; herein incorporated by reference).

The same types of dichotomy found with individual strains of microbes are also found in with mixtures comprising at least 2 or more strains, even when one strain was a known beneficial strain. Because mixtures of microbial species may or may not be beneficial to any particular type of plant, or a variety of plant, or to a range of plant species, each microbial mixture needs to be tested on the desired types of plants, such that "desired plants" are the plants the grower intends to cultivate (grow) in order to determine whether the mixture provides any desired benefit to a plant, where a "desired benefit" is any one of enhancing plant growth and plant productivity, such as those described herein, including but not limited to those demonstrated by mixtures of the present inventions. For one example, see, U.S. Pat. No. 6,194,193; herein incorporated by reference). To the best of the inventor's knowledge no microbial formulation on the market is specifically designed to contain a comprehensive set of microbial groups with multiple complementary functions combined with documented efficacy for substantially increasing productivity of such a broad spectrum of important plants. A broad spectrum of plants that includes but is not limited to cereals, vegetable, and forage crops as reported herein.

Heavy use of chemical fertilizers and pesticides that are often employed for increasing crop productivity now result in leaching of nitrates which at high levels pose a health hazard to humans. Further more, when soils become anaerobic, nitrate ($NO_3$) is reduced to nitrous oxide $N_2O$, which is over 300 times more potent than $CO_2$ as a greenhouse gas. Polymicrobial formulations such as those of the present inventions are contemplated for providing a substantial decrease in the need for nitrogenous fertilizer applications to soil (by almost 50%) and further for a substantial decrease in the amount of chemical pesticide use. Therefore, polymicrobial formulations, such as F2, subformulations of F2, overlapping formulations of F2, and contemplated formulations using isolates of the present inventions showing an increase in potency over F2, have the potential to greatly increase crop productivity with less dependence on chemical fertilizers and pesticides. The use of polymicrobial formulations of the present inventions would greatly reduce the cost of plant cultivation while alleviating negative health and environmental consequences associated with the use of toxic chemical compounds. Polymicrobial formulations would also help solubilize key plant nutrients such as phosphate and make it more available for uptake by the plant. Moreover, products such as F2, consisting of microbes that naturally occur in nature, are eco-friendly, conserve soil health in increasing the number of bacteria beneficial to crop productivity, ensure better utilization of our natural resources, and are highly compatible with sustainable agricultural practices.

Two other important considerations by the inventors were the cost-effectiveness of the formulation the relative stability of the product with the organism remaining viable for at least a few months at ambient temperature (Ilungo, 2004). Moreover, the microbial products on the market with some promise of efficacy are priced too high with some costing as much as $25.00 or more per acre. None the less, it is likely that the research for efficacious microbial inoculants will become more intensive in the further because of the obvious advantages with these products in minimizing the input of nitrogen fertilizer and chemical pesticides as described herein. It is likely that there would be a greater use in the future of efficacious microbial inoculant formulations in agriculture and land management strategies resulting in more efficient crop production in a eco-friendly manner. The current trend is that consumers are willing to spend high amounts to support food products produced by such organic farming.

In one embodiment, the present invention contemplates artificial mixtures of microbial populations for use in formulations of the present inventions for enhancing the growth of plants. Further, the formulations provided herein were shown to be beneficial for plant growth and plant productivity as described herein.

I. Types of Microbes Found in Soil that were Isolated and Described Herein.

In general, soil bacteria may be classified as nitrogen fixing and non-nitrogen fixing. Two major types of nitrogen fixing bacteria (diazotrophs) are known: symbiotic nitrogen-fixing bacteria as exemplified by *Rhizobium, Azorhizobium, Sinorhizobium*, and *Ensifer* species and free-living nitrogen-fixing bacteria such as *Paenibacillus, Azospirillum*, and various others. The inventors collected soil samples then isolated in pure culture numerous types of diazotrophic rhizobacteria, including symbiotic diazotrophs, such as *Azorhizobium caulinodans* KN, *Bradyrhizobium japonicum, Rhizobium trifolii* FD, *Rhizobium meliloti* FD, *Rhizobium phaseoli* and free living diazotrophs, such as Azospirillum, *Acetobacter* sp. LK. These bacteria were isolated from two types of sources, nitrogen-fixing nodules of a variety of leguminous species and from rhizospheres representing tropical and subtropical soils.

Soil-borne fungal species, in addition to causing disease, may also function to prevent disease. For example, "*Trichoderma* spp. are fungi present in substantial numbers in nearly all agricultural soils and in other environments such as decaying wood. Among their other activities, such as inhibiting the growth of plant pathogens, they grow tropically toward hyphae of other fungi, coil about them in a lectin-mediated reaction, and degrade cell walls of the target fungi. This process (mycoparastitism) limits growth and activity of plant pathogenic fungi. In addition to, or sometimes in conjunction with mycoparasitism, individual strains may produce antibiotics. However, numbers and the physiological attributes of wild strains are not sufficient for highly effective control of plant diseases." (*Trichoderma* for Biocontrol of Plant Pathogens: From Basic Research to Commercialized Products, Harman, Cornell Community Conference on Biological Control, Apr. 11-13, 1996, www.nysaes.cornell.edu/ent/bcconf/talks/harman.html). "*Trichoderma* strains are more efficient for control of some pathogens than others, and may be largely ineffective against some fungi. The recent discovery in several labs that some strains induce plants to "turn on" their native defense mechanisms offers the likelihood that these strains also will control pathogens other than fungi . . . . Further, plant growth promotion: For many years, the ability of these fungi to increase the rate of plant growth and development, including, especially, their ability to cause the production of more robust roots has been known. (*Trichoderma* spp., including *T. harzianum, T. viride, T. koningii, T. hamatum* and other spp. Deuteromycetes, Moniliales (asexual classification system) (Ascomycetes, Hypocreales, usually *Hypocrea* spp., are sexual anamorphs, this life stage is lacking or unknown for biocontrol strains)" (Harman, Cornell Community Conference on Biological Control, Apr. 11-13, 1996, www.nysaes.cornell.edu/ent/biocontrol/pathogens/trichoderma.html), in addition to their antifungal properties, for example, U.S. Pat. No. 6,280,719; herein incorporated by reference).

*Trichoderma* are free living and fast growing fungi in soil and root ecosystems of many plants. *Trichoderma* have been demonstrated to inhibit a broad spectrum of root pathogens and foliar pathogens (Harmon et al., 2004, Mathivanan et al 2000) by one or more of the following mechanism: antibiosis, antagonism, competitive exclusion, production of phytohomones, phosphate solubilization, and serving as biochemical elicitors of disease resistance, Furthermore, *Pseudomonas* and *Trichoderma* species which function as bio-control agents do not inhibit arbuscular mycorrhizal fungi, what are very useful in positively influencing the mineral nutrition (especially P) of the plant.

Therefore, the inventors contemplated mixtures comprising known fungal isolates. Further, the inventors' contemplated isolating novel fungal isolates. Even further, the inventors contemplated mixtures comprising isolates of the present inventions, such as a variety of *Trichoderma* species as described herein, to expand their spectrum of antifungal activity and began testing mixtures of fungal microbial formulations, with and without bacteria isolates. See, Examples.

Nitrogen fertilizer is the highest on-farm cost item needed for crop production. So, the most effective way to increase crop productivity is through management of nitrogen fertilizer supply to the plant. Hence, nitrogen-fixing microbes are highly beneficial in minimizing on-farm cost of crop production. The inventors contemplate that microbial formulations designed by them and containing both symbiotic and free-living nitrogen-fixing bacteria would enhance the growth and productivity of a broad spectrum of crops.

The inventors contemplate that microbial formulations containing a complex mixture of microbial organisms would be able to enhance plant growth and productivity of a number of commercial crops of interest. Further, the inventors contemplated that in one embodiment, the use of microbial mixtures of the present inventions would reduce the use of the chemical pesticides on that plant application. Preferably, the inventors contemplated that in one embodiment, the use of microbial mixtures of the present inventions would eliminate the use chemical pesticides on plants. Such an approach for reducing and eliminating the use of harmful chemicals would be ideal for a range of reasons, including contributing to enhanced plant productivity for human consumption while at the same time minimizing environmental damage. Minimizing environmental damage includes obviating the need for artificial (synthetic) chemical pesticides and artificial chemical fertilizers many of which are known to persistent in the environment and whose presence is harmful to ecosystems including humans, animals, insects and natural microbial populations.

The inventors contemplate that microbial compounds of the present inventions can be combined or mixed, or into which they can be dissolved or suspended or mixed. Suitable carriers which are well known include but are not limited to water, solvents, aqueous solutions, such as mineral solutions, humic acid solution, etc., slurries, or dry powders; additional carriers include petrolatum products and diatomaceous earth (see e.g. U.S. Pat. No. 5,326,560; herein incorporated by reference). Other additional components, which may facilitate application of the composition to plants or seeds and which are well known, include but are not limited to buffering agents, wetting agents, coating agents, abrading agents and other adjuvants, including but not limited to petroleum based materials or vegetable based materials, corn-starch encapsulated herbicide granules, citric acid, and complex polysaccharides (see e.g., U.S. Pat. No. 5,945,377; herein incorporated by reference) and alkali metal silicates (see e.g. U.S. Pat. No. 5,183,477; herein incorporated by reference). In other preferred embodiments, the compositions further comprise components which aid plant growth and protection; such components include but are not limited to fertilizer, insecticide, fungicide, nematocide, herbicide, and the like. In yet other preferred embodiments, compositions further comprise components that facilitate application of the composition to the plant, the plant part or the plant seed; such components include but are not limited to buffering agents, wetting agents, coating agents, and abrading agents.

II. Amendments for Use in Formulations of the Present Inventions.

In some embodiments, liquid carriers of the present inventions further comprise a botanical compound. Indeed, a variety of botanical compounds are contemplated, including but not limited to citrus pulp, preformed oil in water emulsion, corn cobs, corn meal, cracked corn, corn oil, edible oil, wheat bran, grape pomace, crude sorbitol, apple pomace, rice hulls, emulsified cottonseed oil, et cetera.

In some embodiments, liquid carriers comprise a spreader or wetting agent to ensure "wetting" of the surface to be sprayed. Examples of wetting agents and spreaders include but are not limited to dried milk, powdered casein, gelatin, detergents, saponins, soaps, emulsifiers, such as alkyl fenols, Tween 20, Tween 80, Sandovit, 9 D 207, Novémol, Pinolene 1882, Petro AG, Span 80, Triton X45, Triton N60, Triton X100, Triton X114, Triton GR7M, Triton 155, Atlox 848, Atlox 849, Tween 80, Atlox 3404/849, Atplus 448, Atplus 300 F and the like. The concentration of wetting agent generally varies usually from 0.5% to 3.0% depending on the concentration of the morphology and the surface properties of the active ingredient.

Plants bred or engineered for resistance to numerous diseases caused by harmful soil borne microbes have not yet been developed. Growers currently depend on pesticides to fight some soil borne diseases while for other soil borne diseases there are no effective treatments.

The use of many pesticides causes environmental damage while there is increasing amounts of public pressure against using them, some pesticides are expensive, difficult to apply, or not completely effective against soil borne pathogens. Moreover, pesticides may indiscriminately kill both harmful and helpful soil microbes or present a health risk to humans and animals. Cultural control methods such as crop rotation may affect soil borne diseases very little since the pathogens that cause them attack a wide range of crops and can live in soil for a long time.

Current population of 6.5 billion human on this planet and the projected need to raise world food production by 110% in the next 50 years to meet the growing food needs of the fast rising population, a decrease in arable land, and biofuels replacing food crops in many countries pose a greater challenge to food production industry worldwide (Triplett et al 2007). Indeed, a massive global effort is needed to increase world food production to keep pace with the needs of the rising human population. Using conventional approaches, high levels of nitrogenous fertilizers are needed to increase world food production to higher levels. Moreover manufacture of nitrogen fertilizer requires fossil fuels as energy source resulting in the release of carbon dioxide, a greenhouse gas, and thus contributes to global warming. Furthermore, skyrocketing fossil fuel costs have pushed the cost of nitrogen fertilizers to record levels. This is quite significant considering the fact that nitrogen fertilizer is the highest farm cost for many food crops. Moreover the high use of the nitrogen fertilizer has adverse environmental consequences because of the leaching in to the ground water of nitrogen compounds such as nitrate, which at high levels poses a health hazard to humans.

Furthermore, when soils become anaerobic, nitrate ($NO_3$) is reduced to nitrous oxide ($N_2O$) which is 319 times more potent than carbon dioxide in contributing to global warming. Hence, there is a vital need for an innovative microbial product that greatly reduces or eliminated the need for adding nitrogen fertilizer to a variety of food crops. This would contribute not only to a substantial reduction in the costs of food production but also would reduce the potential health and environmental hazards that could result in the heavy use of nitrogen fertilizers. Moreover, a polymicrobial inoculate that would reduce or eliminate the need for added chemical pesticides, by the including a Biocontrol agent(s), would not only give a cost advantage to the food producer but would also eliminate another potentially important health and environmental hazards. Hence, microbial growth formulations that contain divers species of symbiotic nitrogen fixing bacteria to provide fixed nitrogen needed by leguminous crops (such as soybeans, beans, peas, alfalfa, etc.) and free living nitrogen bacterial for providing fixed nitrogen to nonleguminous crops (such as corn, rice, wheat, etc.) would be highly desirable. Furthermore, the presence of microbes that serve as natural bio-control agents against plant pathogens, other microbes that stimulate plant growth by mobilizing minerals such as phosphorus, and those that produce plant growth factors would be very desirable.

Furthermore, when soils become anaerobic, nitrate ($NO_3$) is reduced to nitrous oxide ($N_2O$) which is 319 times more potent than $CO_2$ in contributing to global warming. Hence, there is a vital need for an innovative microbial product that greatly reduces or eliminated the need for adding nitrogen fertilizer to a variety of food crops. This would contribute not only to a substantial reduction in the costs of food production but also would reduce the potential health and environmental hazards that could result from the heavy use of nitrogen fertilizers. Moreover, a polymicrobial inoculate that would reduce or eliminate the need for added chemical pesticides, by the including a Biocontrol agent(s), would not only give a cost advantage to the food producer but would also eliminate another potentially important health and environmental hazard. Hence, microbial growth formulations that contain divers species of symbiotic nitrogen fixing bacteria to provide fixed nitrogen needed by leguminous crops (such as soybeans, beans, peas, alfalfa, etc.) and free living nitrogen bacterial for providing fixed nitrogen to nonleguminous crops (such as corn, rice, wheat, etc.) would be highly desirable. Furthermore, the presence of microbes that serve as natural bio-control agents against plant pathogens, other microbes that stimulate plant growth by mobilizing mineral such as phosphorus, and those that produce plant growth factors would be very desirable.

A successful polymicrobial inoculant should be efficacious and inexpensive (less than $1.00 per acre). Successful implementation of the inventions described herein are contemplated to reduce costs for nitrogen fertilizer usage by close to $30.00 per acre, much lower costs of food to the consumer, and less ground water and atmospheric pollution.

To the best of the inventors' knowledge, there is no polymicrobial inoculant in the marker that meets the comprehensive set of desired criteria described herein.

The inventors contemplate formulations of the present inventions as eco-friendly formulations, such that the production and use of the formulations of the present inventions are made with the health of the ecology and the environment in mind. For example, the inventors contemplate the use of the formulations of the present inventions for reducing the ecological impact of treating plants with harmful chemicals, such as growth altering formulations, for example, growth modulators, herbicides, and pesticides. Further, the inventors contemplate the production and use of the formulations of the present inventions as environmentally safe. Even further, the inventors contemplate the production and use of the formulations of the present inventions as biologically safe. In situations where the addition of a pesticide a formulation of the present inventions would contribute to enhancement of plant productivity, a preferred embodiment an eco-friendly formulation of the present inventions further comprise organic pesticides, such as a bio-herbicides, for example, caffeine, soybean oil, clove extracts; lemon juice, and vinegar acids, such as a biofungicide, for example, cinnamon. Thus, in preferred embodiments the formulations of the present inventions would be used in house plants, greenhouse plants, organic gardening and in fields for providing crops certified as organic produce. Thus in further embodiments, the formulations of the present inventions would be permitted or certified for use organic farming.

Preferred embodiments of eco-friendly formulations of the present inventions do not preclude formulations comprising chemicals, such as herbicides and pesticides, including synthetic chemicals and artificial chemicals. Further, the addition of a chemical contributes to the success of the plant enhancing characteristics of the present inventions. Thus, in some embodiments, the amount of a chemical in a formulation at the point of application is lower than the amount typically recommended for that application. In some embodiments, the inventors contemplate the addition of low quantities of chemicals to formulations of the present inventions, such that the quantities of chemicals in solution when applied to soil and plants would be less than the amounts necessary to achieve equivalent plant growth enhancements when the chemical was used without the microbial mixtures of the present inventions.

Compositions according to the embodiments are prepared by formulating each of the active ingredients, for example, a microbial isolate, separately and then mixing them together to prepare formulations of the present inventions. The point source (i.e. seed, plant, soil, and the like) application amount varies with parameters such as weather conditions, type of formulation, application timing, application method, application location, or the type of plant productivity desired, such as increase in height, increase in leaf diameter, increase in yield, et cetera.

Various components of the microbial formulations are contemplated to include in addition to the microbial isolates, compounds and chemicals (also referred to as "amendments" or "soil amendments") for allowing enhancement of plant productivity including but not limited to humates, surfactants, dispersants, chemical herbicides, nutrients, organic trace minerals, vitamins and natural polysaccharides and polypeptides, etc. These additional are typically in a suspension or solution when formulated into the final composition, however, these components can be added in dry form. Final formulations can be determined using routine greenhouse and field-testing, for example, tests described herein.

The compositions of the present invention can be applied in any way to enhance plant growth and plant productivity. Compositions can be applied undiluted or diluted, directly to the foliage of a plant, to seeds, such as in seed dipping, seedling root dip or soaking the soil, such as a soil drench, or to other medium in which plants are growing or are to be planted. The microbial formulations can be sprayed on, dusted on, applied in irrigation water, applied directly to the soil at the base of a plant, applied directly to a plant, applied to a seed of a plant, applied to a root of a plant, and the like.

As a seed dip the microbial formulations are applied directly to the seed by several methods, such as by dipping seeds into a formulation, soaking the seeds in a formulation, soaking the soil prior to seeding with formulation, and soaking the seeds in the soil with formulation where seeds were planted. In one embodiment, seeds, such as those of legumes, such as peas and beans, and non-legumes, such as rice, corn, and sorghum, can also be soaked in a formulation from 30 minutes to 1 hour prior to sowing.

As a foliar spray, the microbial formulations are applied to plant foliage by methods commonly employed, such as conventional high-gallonage hydraulic sprays, low-gallonage sprays, air-blast, aerial sprays and dusts. Application is contemplated be directed towards any part of the plant including the foliage, base of the stems, branches, roots, or soil surrounding the roots. The microbial formulations of the invention may also be injected into plants or sprayed onto vegetation using electrodynamic spraying techniques or other low volume methods, or applied by land or aerial irrigation systems. The dilution and rate of application will be adjusted depending upon the type of equipment employed, the method and frequency of application desired, the crop, the climate, and the weeds to be controlled. The amount of bacteria, nutrient matrix and additives can be adjusted to accommodate the growers' particular needs.

In some embodiments, the inventors contemplate protective and time released coatings where the microorganisms may be separately encapsulated in coatings, such as water soluble coatings and UV (ultraviolet) light protective coatings, e.g., dyed or undyed gelatin spheres or capsules, or by micro-encapsulation, such as by forming a free flowing powder encasing microorganisms. Examples of such coatings are one or more of the following: gelatin, polyvinyl alcohol, ethylcellulose, cellulose acetate phthalate, or styrene maleic anhydride. The compositions can also be formulated in paraffin. The separately encapsulated microorganisms may be mixed directly with a carrier solution. In another case, encapsulated microorganisms may be mixed with non-encapsulated components. In one embodiment, encapsulation of the microorganisms includes nutrients as well as the microorganisms.

Aqueous suspension concentrates of largely insoluble solids may be prepared by ball or bead milling with a dispersing agent with a suspending agent included to stop the solid settling. Compositions to be used as sprays may be in the form of aerosols wherein the formulation is held in a container under pressure of a propellant, e.g. fluorotrichloromethane or dichlorodifluoromethane. Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in McCutcheon's "Emulsifiers and Detergents", McCutcheon's "Emulsifiers and Detergents/Functional Materials" and McCutcheon's "Functional Materials" all published annually by McCutcheon Division of MC Publishing Company (New Jersey), herein incorporated by reference. The microbial formulations of the present invention typically have one or more surfactants. The surfactants customarily employed in the art of formulation of mixtures for foliar sprays or soil drenches are described e.g. in "1985 International McCutcheon's Emulsifiers and Detergents" Glen Rock, N.Y. 07452, USA; "Encyclopedia of Surface Active Agents", Chemical Publishing Co., Inc. New York, 1980; herein incorporated by reference. Suitable surface-active compounds are nonionic, amphoteric and/or anionic surfactants having good emulsifying, dispersing and wetting properties. The term "surfactants" will also be understood as comprising mixtures of surfactants. Surfactants include oil based spray additives, for example, certain mineral oil and natural plant oil (such as soybean and rape seed oil) additives, or blends of them with other adjuvants.

For the preparation of emulsifiable concentrates, the compositions used in the invention can be dissolved in suitable solvents or a mixture of solvents, together with an emulsifying agent that permits dispersion of the active compounds in water. Wettable powders suitable for spraying, can be prepared by admixing the composition with a finely divided solid, such as clays, inorganic silicates and carbonates, silicas, and incorporating wetting agents, sticking agents, and/or dispersing agents in such mixtures.

When the microorganisms are dried or in spore form, they can be formulated into soluble powders or granules, which may contain surface-active agents to improve water dilution and prevent crystallization in a spray tank. The present compositions may be formulated to include a solid carrier to make, for example, tablets, dusts, and the like. Dusts are prepared by mixing a formulation of the present invention, or complexes thereof, with finely divided inert solids, which can be organic or inorganic in nature. Inert materials useful for this purpose include botanical flours, silicas, silicates, carbonates and clays. When formulated into dustable powders or granules, fillers can be used such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. They may also be formulated in biodegradable polymeric formulations to obtain a slow, controlled release of the active substance. Concentrates should preferably be able to withstand storage for prolonged periods and after such storage be capable of dilution with water in order to form aqueous preparations which remain homogeneous for a sufficient time to enable them to be applied by conventional spray equipment.

Although not required, this composition may contain additional additives including fertilizer, insecticide, fungicide, nematacide, and mixtures thereof. Suitable fertilizers include $(NH_4)_2NO_3$. One example of a suitable insecticide is an organophosphate parasympathomimetic (Malathion) however any insecticide may be used in or with the formulations of the present inventions. One useful fungicide includes ethanethiol (ethyl mercaptan; Captan) however any fungicide may be used in or with the formulations of the present inventions.

Other suitable additives include buffering agents, wetting agents, coating agents, and abrading agents. These materials can be used to facilitate the process of the present invention. In addition, the biocontrol agent can be applied to plant seeds with other conventional seed formulation and treatment materials, including clays and polysaccharides.

III. Induction of Systemic Resistance in the Host Plant and Root Environments.

A. Biocontrol Using Bacteria Species.

Numerous bacteria species are known for their capability to associate with induction of or enhancement of systemic resistance to pathogens. However, not every bacteria isolate within such species has an equivalent capacity. For example, *Paenibacillus* species, are known for their ability to fix atmospheric nitrogen. Further, certain *Paenibacillus* isolates are shown to inhibit microbial pathogens in the rhizosphere by producing antimicrobial substances. Thus they act as plant growth promoters as well as biocontrol agents (see, von der Weid, et al., 2003. Antimicrobial activity of *Paenibacillus peoriae* strain NRRL BD-62 against a broad spectrum of phyto pathogenic bacteria and fungi. J. Appl. Microbiol. 95:1143-1151; herein incorporated by reference). Further, in some embodiments, the inventors contemplate adding at least one or more known microbial isolate to formulations of the present inventions. Such isolates include but are not limited to, *Paenibacillus brasiliensis* 172, *Paenibacillus peoriae* deposited as NRRL BD-62, *Paenibacillus polymyxa* deposited as NRRL B37-A.

Further, the inventors contemplate isolating at least one novel *Paenibacillus* stain for providing antimicrobial plant enhancing capabilities to formulations of the present inventions, such as the strain described herein.

B. Biocontrol Using Fungal Species.

Fungal isolates demonstrate a range of activity such that while one isolate causes disease in a plant, another isolate will protect a plant from disease. Specifically, *Trichoderma* isolates are used for biocontrol of plant diseases (Howell, 2003, Mechanisms employed by *Trichoderma* species in the biological control of plant diseases: The history and evolution of current concepts. Plant. Dis. 87:4-10; Benítez, et al., 2004, Biocontrol mechanisms of *Trichoderma* strains. Int Microbiol. December; 7(4):249-60. Review, all of which are herein incorporated by reference). General review on *Trichoderma* being plant symbionts: Harman, et al., 2004, *Trichoderma* species Opportunistic, avirulent plant symbionts. Nature Rev. 44:43-56, herein incorporated by reference. Further, in addition to fungal species directly controlling other fungal species, certain fungal species were shown to induce increased pathogen resistance in plants (Shores, et al., 2005. Involvement of Jasmonic Acid/Ethylene Signaling Pathway in the Systemic Resistance Induced in Cucumber by *Trichoderma asperellum* T203, Phytopathology 95:76-84, herein incorporated by reference).

A variety of pesticides belonging to different chemical classes are used for controlling disease affecting a variety of crops. Pesticides include bactericides and fungicides and a number of them are toxic to humans, some even at parts per billion. Furthermore, some of the pesticides are recalcitrant to degradation and persist in the environment and enter the humans/animal food chain. Such safety and environmental concerns are driving the search for more environmentally friendly methods to control plant disease that will contribute to the goal of sustainability in agriculture. Hence, bio-control agents (bio-pesticides) affecting different plant disease are preferred. Many fungi and bacteria have been exploited as biological control agents for inhibiting pathogenic fungi, bacteria and even nematodes and small insects. These soil-borne, non-pathogenic bacteria with the ability to antagonize fungal phytopathogens and thus prevent plant disease represents a realistic alternative to chemical fungicides. The bacteria that serve a biological control agents (BCAs) and plant growth promoting rhizobacteria (PGPR) as well as pseudomonads (which are known bio-pesticides are catabolically versatile, have excellent root-colonizing abilities, and have the capacity to provide a wide range of metabolites that act against plant pathogens. Some soil microbes have been shown to elicit a disease resistant response in crop species, a phenomenon known as induced systemic resistant (ISR). *Pseudomonas* strains with the ability to produce the antifungal metabolite 2,4-diacetylphloroglucinol (Phl) can be isolated at high frequencies form soils suppressive to black root rot of tobacco and take-all disease of wheat. Given the ecological important of Phl production, many of *Pseudomonas* BCAs, bio-control efficacy has been liked to the production of this metabolite. In addition to Phl production, other secondary metabolites including pyoleueorin, pyrrolnitrin, and phenazines have been associated to bio-control (see review Walsh et al., 2001). *Bacillus* spp., such as *Bacillus subtilis* are known to suppress soil-borne fungal diseases and nematodes, produce metabolites that stimulate plant and root growth, and by colonizing the root zone which excludes some pathogens by competitive exclusion.

IV. Induction of Modulation by Fungal Species for Enhancing Nitrogen Fixation in Leguminous Plants.

Nitrogen fixation in legumes is sensitive to soil acidity that can limit growth and persistence of *rhizobia*, the nitrogen fixing bacteria in soils (Graham, 1998, Biological dinitrogen fixation: Symbiotic. p. 322-345. In Sylvia et al. (ed.) Principles and applications of soil microbiology. Prentice-Hall, Upper Saddle River, N.J.; herein incorporated by reference). The range in sensitivity can be exemplified where fast-growing *rhizobia* that inoculate peas and lentils are generally more sensitive to soil acidity than strains that nodulate soybean, although acid-tolerant *rhizobia* strains exist. Further, failure to nodulate roots in acid soils is due to both the lower numbers of *rhizobia* and to the failure of attachment of *rhizobia* to the root hairs. Although it is common to lime acid soils, the areas involved especially in the Palouse and the cost and availability of limestone often limit this practice. Alternative practices to combat soil acidity include using acid-tolerant inoculant *rhizobia* strains on host plants and lime pelleting (coating) of inoculated seed. Liming also resulted in increased nodulation in common bean and alfalfa (Buerkert et al, 1990; Pijnenberg and Lie, 1990, all of which are herein incorporated by reference).

*Rhizobia* are a group of symbiotic nitrogen fixing bacteria that contribute fixed nitrogen and promote production of leguminous plants and have been widely used as inoculants. It was estimated that nitrogen fixing microbes associated with legumes grown on 25 million ha of land in Australia fix USD 3-4 billion worth of nitrogen annually (Brokwell, 2004, Bullard et al. 2005). It is estimated that biological nitrogen fixation on a global scale reaches a value of 175 metric tons of nitrogen fixed per year (Hubbel and Kidder, 2003). Of this total, symbiotic nitrogen fixation accounts for 20%. Grain legumes such as cowpea, peanut and soybean fix 250 of nitrogen per acre per year. Forage legumes have been estimated to fix up to 250-300 lb nitrogen per acre. These statistics point to the importance of symbiotic nitrogen fixing organism as a source of fixed nitrogen for the leguminous plants. The best known and most exploited symbiotic nitrogen fixing *Rhizobia* fall with the genera: *Rhizobium, Bradyrhizobium, Sinorhizobium* (renamed *Ensifer*), *Mesorhizobium, Allorhizobium,* and *Azorhizobium* (O'Hara et al 2003, Sorent 2001). It is of considerable inters that several non-*Rhizobial* species belonging to the alpha subgroup of Proteobacteria such as Methylobacerium, Phyulobacterium, Garobacerium, Hervaspirillum and Burkholderia have been reported form nodules and fix nitrogen in leguminous plants (Balachandar et al., 2007). Similar root nodule associated N2 fixation has also been reported form some gamma-Proteobacteria (Benhizi et al, 2004).

In addition to symbiotic N2 fixing bacteria, there are a number of free-living N2 fixing bacteria. The Azospirillum group of organisms are microaerophilic nitrogen fixers commonly found in association with the roots of cereals such as rice, wheat and corn and certain forage grasses (Bashan et al., 2004). Azospirillum group makes significant contribution to nitrogen fixation and substantially decreases the level of nitrogen fertilizer needed for cereal crop production. Several studies indicate that Azospirillum can increase the growth of various crops like sunflower, vegetables, cotton, wheat and rice (Bashan et al., 1989). *Azospirillum canadense, A. lipoferum, A. oryzae, A. brasiliense* are some of the known species that contribute to enhanced plant growth, nitrogen fixation and nutrient assimilation (Bashan et al., 2004). Other free living microbes that contribute to N2 fixation included: *Acetobacter* and *Herbaspirillum* associated with sugarcane, sorghum, and maize (Balachandar et al 2007, Boddey et al., 2000) and *Alcaligenes, Bacillus, Enterobacter, Klebsiella* and *Pseudomonas* strains associated with a range of crops such as rice and maize (Somasegaran and Hoben, 1994). *Azotobacter, Beijerinkia* and *Clostridia* are also recognized as free living N2 fixers (Polianskais et al., 2003).

Moreover, a number of plant growth promoting rhizobacteria are nitrogen fixers and five a positive growth response that has been attributed to secondary growth promoting compounds, such as plant growth hormone, produced by these organisms (Polianskais et al., 2003). *Paenibacillus, Burkholderia,* and alpha, beta, and gamma) *Proteobacteria* have also been reported to fix nitrogen or otherwise stimulate plant growth. *Paenibacillus polymyxa* increase both numbers and nodulation by *Rhizobium* species (Petersen et al., 1996). Phosphate-solubilizing bacteria (PSB) are also important as they have been reported to produce organic acids and convert insoluble P compound to soluble for uptake by the plant. Important Phosphate solubilizing organisms include but are not limited to *Pseudomonas, Bacillus, Azospirillum, Rhizobium, Alkaligenes, Paenibacillus,* and *Penicilluim digitatum* (Rodriguez and Fraga, 1999). PSB are of great value in allowing the use of less expensive P sources (Sundara et al., 2002).

Many of the plant growth promoting bacteria such as *Bacillus* spp. and *Pseudomonas* spp. have also been reported to posses multi beneficial characteristics such as nutrient recycling, nutrient uptake and phytohomone production (Rai., 2006).

So although other *Tichoderma* spp. were known for treating plants to protect certain plants against certain pathogens, the inventors demonstrate herein that solutions consisting of multiple *Tichoderma* spp. of the present inventions induce nodulation of pea plant roots. Thus additional embodiments encompass the use of formulations comprising *Trichoderma* species of the present inventions for enhancing plant productivity, in particular legume formation and increased nitrogen fixation. In some embodiments, the formulations consist of *Trichoderma* species of the present inventions for enhancing plant productivity.

V. Formulations.

The inventors contemplate a variety of formulations for use in the present inventions. In one embodiment, the inventors contemplate a microbial mixture for use in a variety of soil environments. Such a mixture would comprise isolates capable of surviving under a variety of environments for conferring a benefit to a plant and to populations of plants.

A. Providing Formulations of the Present Inventions from Deposited Mixtures.

The inventors contemplate the use of deposited mixtures, for example, F2A and F2B, for providing formulations of the present inventions. The following is a contemplated procedure for thawing, growing and mixing the microorganisms for use in the present inventions, for example, Sumagro-4, 5 and 2.

Methods of thawing and growing lyophilized bacteria and fungi are commonly known, for example, Gherna, R. L. and C. A. Reddy. 2007. Culture Preservation, p 1019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages; herein incorporated by reference. Thus freeze dried liquid formulations and cultures stored long term at −70° C. in solutions containing glycerol are contemplated for use in providing formulations of the present inventions.

Sumagro-4 (F4) fungal formulations are made directly from fungal mixtures of F4 as described in the Examples. Formulations of the bacteria isolate mixtures shown for Sumagro-2 are also made directly from stored bacteria mixtures containing the bacteria listed for Sumagro-2 as described in the Examples. Sumagro-2 is provided by combining the mixture of bacteria isolates and mixture of fungal isolates according to descriptions provided in the Examples herein.

B. Re-Isolating Microbes of the Present Inventions for Providing Isolates for Use in Additional Formulations, as Individual Isolates, Mixtures and Formulations.

Alternatively, formulations of the present inventions and additional formulations, including formulations of individual isolates and formulations of a variety of combinations of the microbes are contemplated. These formulations may be provided by re-isolating each microbe from the formulations described herein. Even further, these formulations may be provided by re-isolating individual isolates from mixtures, such as F2A and F2B. Specifically, bacteria may re-isolated using the isolation methods and identification methods as described herein and in: C. A. Reddy, T. J. Beveridge, J. A. Breznak, G. A. Marzluf, T. M. Schmidt, and L. R. Snyder (eds.). Methods for General and Molecular Microbiology, Am. Soc. Microbiol., Washington, District of Columbia. In particular, individual bacteria isolates may be provided by serial diluting mixtures and plating for isolation of single colonies followed by growing isolates for 16s rDNA identification. Further, individual bacteria isolates may be provided from formulations, such as F2, and soil samples treated with formulations of the present inventions, such as F1, F2, etc. Individual isolates matching those provided herein, may be identified with 16s RNA PCR techniques as described in the Examples. Fungus isolates may also be re-isolated from mixtures, formulations and treated soil. These isolates are serially diluted, plated, grown and identified as described in the Examples.

These re-isolated bacteria and fungal isolates are contemplated for use in a variety of formulations. Specifically, individual isolates are contemplated for further testing and for use individually and in combinations. In one embodiment, the microbial isolate is combined with other isolates provided herein for providing formulations of the present inventions. In another embodiment, the microbial isolate is combined in subformulations of the present inventions. In even further embodiments, the microbial isolate is combined in any combination with other isolates in order to provide formulations of the present inventions.

VI. Applications.

In addition to field and greenhouse applications, the inventors further contemplate using formulations of the present inventions for enhancing plant growth in house plants, on lawns, sports fields, highway areas, such as medians, roadsides, exit and entrance lanes, and to encourage growth of wildlife populations, such as National Forests, wildlife protection areas, private reserves, and the like. Further, the inventors contemplate using formulations of the present inventions for replanting areas with severely altered or damaged soils, including soils with high acidity.

In some embodiments, the inventors contemplate adding formulations of the present inventions in mulching material for treating plants, for one example, mulching material for blueberry plants.

In some embodiments, the inventors contemplated using formulations of the present inventions for increasing biomass of plants for use in alternative energy programs such as biofuel production. The inventors contemplate the use of their formulations on large tracts of switch grass (prairie grass) for increasing biomass. In particular since formulations of the present inventions are contemplated to boost biomass production from single and multiple stands of prairie grass, these formulations may overcome the limitations reported as "Pure switch grass stands may not be best for ethanol By DALE HILDEBRANT, Farm & Ranch Guide Friday, Apr. 13, 2007 9:18 AM: CDT. "According to Hill, their study found that mixtures of 16 native prairie species produced 238 percent more energy on average than a single prairie species such as switch grass and as an added bonus, the stands made up of the plant mixtures removed large amounts of carbon dioxide from the air and stored it in the soil, but that the single species stands did not."

In particular, the inventors contemplate the use of formulations of the present inventions for organic farming and production of crops for designation as organic products. Even further, the inventors contemplate the use of formulations of the present inventions for treating plants in areas of low water or drought, such that formulations of the present inventions would enhance drought resistance in treated plants.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in microbiology, botany, biochemistry, chemistry, molecular biology, plant biology, plant disease, and plant pathogens, or related fields are intended to be within the scope of the following claims.

EXPERIMENTAL

The following examples serve to illustrate certain embodiments and aspects of the present invention and are not to be construed as limiting the scope thereof.

In the experimental disclosures which follow, the following abbreviations apply: N (normal); M (molar); mM (millimolar); μM (micromolar); mol (moles); mmol (millimoles); μmol (micromoles); nmol (nanomole); pmol (picomole); g (gram); mg (milligram); μg (microgram); ng (nanograms); pg (picogram); L and l (liter); ml (milliliter); μl (microliter); cm (centimeter); mm (millimeter); μm (micrometer); nm (nanometer); U (unit); min (minute); s and sec (second); k (kilometer); deg (degree); and ° C. (degrees Centigrade/Celsius), potato dextrose agar (PDA) and tryptone-mannitol-yeast extract (TMY).

As used herein, an exemplary comparison commercial product was NutraGro (Nutragro), designated NG, (BioSoil Enhancers, Inc., originally, Bio-Solutions Manufacturing, Inc.) which was a solution providing "mixed cultures of beneficial microbes, macro and micronutrients, and bioactive substances to promote soil health and crop potential." (Market Wire, April, 2006, at //findarticles.com/p/articles/mi_p-wwi/is_200604/ai_n16121689, herein incorporated by reference).

As used herein, one of the exemplary carrier solutions was HumaGro (Humagro), designated HG, (BioSoil Enhancers, Inc., originally, Bio-Solutions Manufacturing, Inc.) a commercially available product which contained "nutrients, organic matter and humic acid, which helps soil, microbes, and plants." (Market Wire, April, 2006, at //findarticles.com/p/articles/mi_pwwi/is_200604/ai_n16121689, herein incorporated by reference). As used herein, another exemplary carrier solution was a mineral solution as described herein.

EXAMPLE I

The inventors' objective was to develop an efficacious, eco-friendly, and cost-effective formulation suitable for enhancing the productivity of a broad spectrum of crops such as cereals, pulses, vegetable, horticultural and floricultural corps. To this end, the inventors were able to isolate multi-functional microbes, useful for constructing a suitable microbial inoculant formulation(s), form root nodules of various legume, rhizosphere soils and soils collected from temperate, tropical and sub-tropical regions. The results indicate a wide range of phenotypic diversity of the isolates. The inventors then constructed at least two microbial inoculant formulation designated F1 and F2, (see Examples below) each with a distinct set of microbes and tested their efficacy on various crops under greenhouse condition and field conditions. Both conditions confirmed enhanced growth and yield of a broad spectrum of legumes, cereals, and vegetable crops as described in the Examples.

Materials and Methods.

A. Providing Soil Microbial Isolates.

The inventors collected soil samples from a variety of global locations including the United States of America. These samples included soil removed from the rhizosphere and root nodules of a variety of plants. When the inventors applied commonly known microbial isolation procedures to these soils, the inventors obtained a variety of microbes including bacteria and fungi that were further subjected to conventional isolation techniques for providing pure isolates as described herein.

1. Isolation of Rhizobacteria from Soil.

In general, a randomly collected 30 g soil sample was obtained at each selected site then air-dried, made free of any pellets, and sieved to remove pebbles and clumped material. The resulting fine powdery soil was suspended in sterile double distilled water and subjected to serial dilutions ($10^{-1}$ through $10^{-7}$). One ml soil suspension from each of the dilutions from $10^{-4}$ to $10^{-7}$ was placed on nutrient agar plates and incubated at 28° C. (spread plate method). Specific growth media and incubation conditions were used to isolate a variety of groups of bacteria from the soil. Dilutions and platings were carried out under sterile conditions.

Standard microbial enrichment technique (C. A. Reddy, T. J. Beveridge, J. A. Breznak, G. A. Marzluf, T. M. Schmidt, and L. R. Snyder (eds.). Methods for General and Molecular Microbiology, Am. Soc. Microbiol., Washington, District of Columbia) was followed to isolate each type of bacteria. For example, for *Azospirillum* sp. isolates, Nitrogen-free malic acid semisolid medium was used for enrichment. Observations of the development of subsurface pellicles during incubation and change of color of the medium from light yellow to blue was suggestive of the presence of colonies of *Azospirillum*. For phosphobacteria isolates, plating of the soil sample was done on Sperbers agar. Those colonies with halos around them were selected and screened for solubilization of tricalcium phosphate. Pikovskays's medium was another general purpose medium for selection of phosphate-solubilizing bacteria. For *Bacillus* sp. isolates the Nutrient medium was used.

Bacteria associated with the plant rhizosphere are referred to as rhizobacteria. For rhizobacteria isolates, plant roots along with adherent soil were carefully removed from the soil, washed twice with sterile distilled water, centrifuged with the resulting pellet resuspended in buffer and was subject to serial dilution technique as described above. *Pseudomonas, Azospirillum* and *Bacillus* sp. were isolated from the rhizosphere samples. Selected agricultural soils were also used for isolating phosphobacteria, *Acetobacter* and some *Bacillus* species.

2. Isolation of Fungal (*Trichoderma*) Species.

Several species of *Trichoderma* for use in the present inventions were isolated from diverse soil samples collected from cultivated agriculture lands, tropical forest soils and sub tropical forest soils. Initial isolations were carried out using dilution plate technique on standard potato dextrose agar medium. Isolated strains were purified by single spore colony and the taxonomic classification was based on colony color, rate of growth, and macro and microscopic features of mycelia, shape and size of conidia and phialids.

The isolated *Trichoderma* species were screened for their bio-control potential against known plant pathogenic fungi using standard dual culture plate technique. *Trichoderma* strains were also tested for their saprophytic competency in soil. Seven of the best isolates were chosen by the inventors for use in formulations of the present inventions.

For long time storage, a sterile soil sample was inoculated with an isolate and stored at 4° Celsius. The *Trichoderma* isolates used in formulations of the present inventions were: *Trichoderma harzianum* (3 strains), *Trichoderma viride* (2 strains), and a strain of *Trichoderma longibrachiatum*, and a strain of *Trichoderma virens*.

Fungal inoculum was prepared in Potato dextrose broth in three steps: first in small tubes, then scaled up to small Ehrlenmeyer flasks, and then up to 2 liter Ehrlenmeyer flasks. A fungal mat was collected by filtration using a sterile Buchner funnel with the fungal mat filtered out through cheese-cloth after which the conidia were collected through centrifugation at 5000×g for 10 minutes. Both mycelial mat and conidial pellet were thoroughly blended in a sterile blender before mixing with the bacterial inoculants in preparing the final formulations.

B. Preparation of Microbial Formulations from Soil Isolates.

Pure stock cultures of bacteria and fungi were grown and then used in the preparation of microbial formulations. Stock cultures of isolates were stored as streaks on tryptone-mannitol-yeast extract (TMY) agar slants at 40° C. until further use.

A liquid carrier containing was used in preparing microbial formulations. In particular, the inventors used a 12% humic acid (v/v) solution at pH 7.0, such as a Humagro solution, in designated formulations, while in other formulations the inventors used a mineral solution.

1. Preparation of Sumagro 1 (F1) in Humagro.

The following are exemplary steps for preparing a Sumagro 1 formulation of the present inventions.

Thirty-three bacterial isolates and 7 fungal isolates (listed in Table 1) were used for preparing Sumagro 1. Culture inoculations and transfers were done under standard aseptic conditions. Specifically, a loop of bacterial culture from a stock slant of the bacterial isolate in Table 1 was used to inoculate 5 ml of TMY liquid broth in 18×150 mm foam-plugged culture tubes and incubated on a shaker at 30° C. for 16 hr for *Bacillus* and 30 hr for *Rhizobium* cultures. One ml from the 5 ml culture was then used to inoculate 75 ml of TMY broth in a 150 ml Ehrlenmeyer flask and incubated as described above. The 75 ml culture was then used to inoculate one liter of TMY broth in 2-liter Ehrlenmeyer flasks and incubated as described above.

The 2-liter flask cultures were harvested by centrifugation at 7000 rpm for 10 min at 4° C. using sterile 500 ml screw-capped centrifuge bottles. The cell pellets from each centrifuge bottle was suspended in 10 ml of the humic acid carrier solution (pH 7.0) mentioned above. Cell suspensions of all the 33 bacterial cultures prepared in this manner were pooled together.

The seven *Trichoderma* strains were cultured individually in potato dextrose broth (rather than in TMY broth) and the same cultivation steps described above for bacterial cultures were used. *Trichoderma* fungal mat was collected by centrifugation as described above and homogenized thoroughly in 50 ml of the carrier solution using a sterile stainless steel blender. The *Trichoderma* suspensions from each of the seven cultures were then pooled together.

The pooled bacterial suspension and the *Trichoderma* suspension was mixed together and made up to a total volume of 5 liters using the humic acid carrier described herein. This formulation consisting of 33 bacterial strains and seven *Trichoderma* strains was designated as Sumagro 1 (F1).

TABLE 1A

Sumagro-1 (F1) Cultures Used in Growth-Enhancing Microbial Formulations.

| Sumagro-1 (F1) Cultures | Genus species designation |
|---|---|
| 1. | *Bacillus* sp. RG-S |
| 2. | *Bacillus* sp. BL |
| 3. | *Bacillus* sp. RG-2L |
| 4. | *Bacillus* sp. Ph.L-1 |
| 5. | *Bacillus* sp. Ph.L |
| 6. | *Ensifer meliloti* FD |
| 7. | *Rhizobium trifolii* FD |
| 8. | *Azorhizobium caulinodans* KN |
| 9. | *Rhizobium* sp. RLG1 |
| 10. | *Azorhizobium* sp. RLG2 |
| 11. | *Azorhizobium* sp. RLG3 |
| 12. | *Rhizobium* sp. RLG4 |
| 13. | *Rhizobium* sp. RLG5 |
| 14. | *Rhizobium* sp. RLG6 |
| 15. | *Azorhizobium* sp. RLG7 |
| 16. | *Rhizobium* sp. RLG8 |
| 17. | *Azorhizobium* sp. RLG9 |
| 18. | *Rhizobium* sp. RLG10 |
| 19. | *Rhizobium* sp. RLG11 |
| 20. | *Rhizobium* sp. Ph |
| 21. | *Rhizobium* sp. B |
| 22. | *Rhizobium* sp. Ph.P |
| 23. | *Rhizobium* sp. L-26 |
| 24. | *Rhizobium* sp. L-27 |
| 25. | *Rhizobium* sp. L-30 |
| 26. | *Rhizobium* sp. L-32 |
| 27. | *Rhizobium* sp. B5 |
| 28. | *Bacillus* sp. B6 |
| 29. | *Rhizobium* sp. B1A |
| 30. | *Rhizobium* sp. B2 A1 |
| 31. | *Rhizobium* sp. M |
| 32. | *Rhizobium* sp. S12 |
| 33. | *Rhizobium* sp. S13 |
| 34. | *Trichoderma virens* 3107 |
| 35. | *Trichoderma viride* LK |
| 36. | *Trichoderma viride* 3116 |
| 37. | *Trichoderma harzianum* 3147 |
| 38. | *Trichoderma harzianum* G |
| 39. | *Trichoderma harzianum* LK |

TABLE 1A-continued

Sumagro-1 (F1) Cultures Used in Growth-Enhancing Microbial Formulations.

| | | |
|---|---|---|
| 40. | *Trichoderma longibrachiatum* 3108 | |
| 40 | Total cultures | |

| Sumagro-1 (F1) Cultures | Genus species designation | Revised culture designation | Genus species designation based upon 16s rDNA |
|---|---|---|---|
| 1. | *Bacillus* sp. RG-S | na | na |
| 2. | *Bacillus* sp. BL | na | na |
| 3. | *Bacillus* sp. RG-2L | na | na |
| 4. | *Bacillus* sp. Ph.L-1 | na | na |
| 5. | *Bacillus* sp. Ph.L | na | na |
| 6. | *Ensifer meliloti* FD | RMEL1 | *Ensifer (Sinorhizobium) meliloti* RM1 |
| 7. | *Rhizobium trifolii* FD | RTRF1 | *Rhizobium leguminosarum* bv. *trifolii* RT1 |
| 8. | *Azorhizobium caulinodans* KN | AZOR1 | *Azorhizobium caulinodans* AZ1 |
| 9. | *Rhizobium* sp. RLG1 | RLNG1 | *Pseudomonas* sp. RL1 |
| 10. | *Azorhizobium* sp. RLG2 | RLNG2 | *Pantoea (Enterobacter) agglomerans* RL2 |
| 11. | *Azorhizobium* sp. RLG3 | RLNG3 | *Stenotrophomonas maltophila* RL3 |
| 12. | *Rhizobium* sp. RLG4 | RLNG4 | *Stenotrophomonas maltophila* RL4 |
| 13. | *Rhizobium* sp. RLG5 | RLNG5 | *Stenotrophomonas maltophila* RL5 |
| 14. | *Rhizobium* sp. RLG6 | RLNG6 | *Bacillus subtilis* RL6 |
| 15. | *Azorhizobium* sp. RLG7 | RLNG7 | *Bacillus subtilis* RL7 |
| 16. | *Rhizobium* sp. RLG8 | RLNG8 | *Pseudomonas* sp. RL8 |
| 17. | *Azorhizobium* sp. RLG9 | RLNG9 | *Bacillus subtilis* RL9 |
| 18. | *Rhizobium* sp. RLG10 | RLNG10 | *Stenotrophomonas maltophila* RL10 |
| 19. | *Rhizobium* sp. RLG11 | RLNG11 | *Pseudomonas* sp. RL11 |
| 20. | *Rhizobium* sp. Ph | | |
| 21. | *Rhizobium* sp. B | na | na |
| 22. | *Rhizobium* sp. Ph.P | na | na |
| 23. | *Rhizobium* sp. L-26 | na | na |
| 24. | *Rhizobium* sp. L-27 | na | na |
| 25. | *Rhizobium* sp. L-30 | na | na |
| 26. | *Rhizobium* sp. L-32 | na | na |
| 27. | *Rhizobium* sp. B5 | na | na |
| 28. | *Bacillus* sp. B6 | na | na |
| 29. | *Rhizobium* sp. B1A | na | na |
| 30. | *Rhizobium* sp. B2 A1 | na | na |
| 31. | *Rhizobium* sp. M | na | na |
| 32. | *Rhizobium* sp. S12 | na | na |
| 33. | *Rhizobium* sp. S13 | na | na |
| 34. | *Trichoderma virens* 3107 | TV LK | *Trichoderma viride* LK |
| 35. | *Trichoderma viride* LK | TV 3116 | *Trichoderma viride* 3116 |
| 36. | *Trichoderma viride* 3116 | TVs 3107 | *Trichoderma virens* 3107 |
| 37. | *Trichoderma harzianum* 3147 | TH 3147 | *Trichoderma harzianum* 3147 |

TABLE 1A-continued

Sumagro-1 (F1) Cultures Used in Growth-Enhancing Microbial Formulations.

| | | | |
|---|---|---|---|
| 38. | Trichoderma harzianum G | TH LK | Trichoderma harzianum LK |
| 39. | Trichoderma harzianum LK | TH G | Trichoderma harzianum G |
| 40. | Trichoderma longibrachiatum 3108 | TLB 3108 | Trichoderma longibrachiatum 3108 |
| 40 | Total cultures | | |

2. Preparation of Sumagro 2 (F-2) in Humagro.

A formulation consisting of 14 bacterial strains and 7 *Trichoderma* strains, where the *Trichoderma* strains were added at twice the concentration in Sumagro 1, was prepared and designated Sumagro 2 (F2). See, Table 2.

Sumagro 2 was prepared as described for Sumagro 1, with the exception of reducing the number of bacterial cultures to 14 (rather than 33 as used in Sumagro 1). Further, the seven *Trichoderma* cultures were added at twice the concentration used in Sumagro 1 (see Table 2 listing Sumagro 2 cultures). Briefly, bacterial and fungal cultures were grown, centrifuged, resuspended, and pooled together as described above for preparing Sumagro 1. The pooled suspension was then made up to 5 liters using the humic acid carrier and stored at 4° Celsius.

TABLE 2A

Sumagro-2 (F2) Cultures Used in Growth-Enhancing Microbial Formulations.

| Sumagro 2 (F2) Cultures | Genus species designation |
|---|---|
| 1. | *Ensifer meliloti* FD |
| 2. | *Rhizobium trifolii* FD |
| 3. | *Azorhizobium caulinodans* KN |
| 4. | *Rhizobium* sp. RLG1 |
| 5. | *Azorhizobium* sp. RLG2 |
| 6. | *Azorhizobium* sp. RLG3 |
| 7. | *Rhizobium* sp. RLG4 |
| 8. | *Rhizobium* sp. RLG5 |
| 9. | *Rhizobium* sp. RLG6 |
| 10. | *Azorhizobium* sp. RLG7 |
| 11. | *Rhizobium* sp. RLG8 |
| 12. | *Azorhizobium* sp. RLG9 |
| 13. | *Rhizobium* sp. RLG10 |
| 14. | *Rhizobium* sp. RLG11 |
| 15. | *Trichoderma virens* 3107 |
| 16. | *Trichoderma viride* LK |
| 17. | *Trichoderma viride* 3116 |
| 18. | *Trichoderma harzianum* 3147 |
| 19. | *Trichoderma harzianum* G |
| 20. | *Trichoderma harzianum* LK |
| 21. | *Trichoderma longibrachiatum* 3108 |
| 21 | Total Cultures |

Note:
Concentration of each of the *Trichoderma* strains were doubled in Sumagro 2 based on the rationale that *Trichoderma* strains are potent inhibitors of fungal pathogens, induce host resistance to bacterial and fungal plant pathogens, induce production of growth-stimulating hormonal substances such as auxins and cytokinins, and the inventors observed in preliminary experiments that they stimulate nodulation by soil diazotrophs (Benitez, et al. 2004. Biocontrol mechanisms of *Trichoderma* strains. International Microbiology 7: 249-260; herein incorporated by reference).
Theses product formulations appear stable over a 6-month period at ambient temperature.

16S rDNA Sequencing for Molecular Identification of Bacterial Isolates of the Present Inventions.

This Example describes an exemplary method for determining the Genus species of the bacterial isolates of the present inventions.

Polymerase chain reaction (PCR) amplification of DNA from each given isolate for 16S rDNA sequencing was done using established procedures (Mignard and Flandrois, 2006; Pandey et al., 2004; Petti, 2007; each of which are herein incorporated by reference in their entirety). The 16S rRNA gene from the total DNA of a bacterial strain was amplified with bacterial universal forward primer 8F (number of bases 20) with the sequence: AGAGTTTGATCCTGGCTCAG (SEQ ID NO: 1). The reverse primer (1492R with 19 bases) had the sequence: GGTTACCTTGTTACGATT (SEQ ID NO: 2). These primers were obtained from Macromolecular Structure Facility, Michigan state University. Polymerase chain reaction amplification cycles commenced with an initial denaturation at 95° C. for 3 min followed by 30 cycles of 30 sec each at 95° C., 30 sec at 55° C., and 45 sec at 72° C., with a final extension of 10 min at 72° Celsius. PCR products were checked by electrophoresis on 0.8% agarose gel, purified using QIA quick spin PCR purification kit (following the protocol in Quiagen quick spin handbook). Purified PCR products were checked by electrophoresis on 0.8% agarose gel. The PCR purified products were then sequenced using 531R primer (number of bases 18) with the sequence: TAC-CGCGGCTGCTGGCAC (SEQ ID NO: 3). Sequence data were aligned and compared with available standard sequences of bacterial lineage in the National Center for Biotechnology Information Gene Bank (ncbi.nlm.nih.gov/blast/Blast.cgi) using BLAST search program (See, for review, McGinnis S., & Madden T. L., (2004) Nucleic Acids Res. 32:W20-W25; Ye, et al., (2008) Nucleic Acids Res. 34:W6-W9; Johnson et al., (2008) Nucleic Acids Res. 36:W5-W9, each of which are herein incorporated by reference in their entirety.

The validity of the procedure was established by using DNA from known *Rhizobium* and *Azorhizobium* cultures. The procedure described was used for the identification of all the bacterial strains in F1 and F2 formulations (Mignard and Flandrois. 2006. J. Microbiol. Methods 67:574-581; Pandey, et al., 2004. Current Sci. 86: 202-207; Petti, 2007. Clin. Infect. Dis. 44:1108-1114, and Macrae, (2000) Brazilian Journal of Microbiology 31:77-82, each of which are herein incorporated by reference in their entirety).

TABLE 2B

Sumagro-2 (F2) Genus identification of Cultures Used in Growth-Enhancing Microbial Formulations.*

| F2 Cultures: Revised designation | Revised Genus species designation** | Sumagro 2 (F2) Cultures | Initial Genus species designation from Table 2A |
|---|---|---|---|
| RLNG1 | *Pseudomonas* sp. RL1 | 4. | *Rhizobium* sp. RLG1 |
| RLNG2 | *Pantoea* (*Enterobacter*) *agglomerans* RL2 | 5. | *Azorhizobium* sp. RLG2 |
| RLNG3 | *Stenotrophomonas maltophila* RL3 | 6. | *Azorhizobium* sp. RLG3 |
| RLNG4 | *Stenotrophomonas maltophila* RL4 | 7. | *Rhizobium* sp. RLG4 |
| RLNG5 | *Stenotrophomonas maltophila* RL5 | 8. | *Rhizobium* sp. RLG5 |
| RLNG6 | *Bacillus subtilis* RL6 | 9. | *Rhizobium* sp. RLG6 |
| RLNG7 | *Bacillus subtilis* RL7 | 10. | *Azorhizobium* sp. RLG7 |
| RLNG8 | *Pseudomonas* sp. RL8 | 11. | *Rhizobium* sp. RLG8 |
| RLNG9 | *Bacillus subtilis* RL9 | 12. | *Azorhizobium* sp. RLG9 |
| RLNG10 | *Stenotrophomonas maltophila* RL10 | 13. | *Rhizobium* sp. RLG10 |
| RLNG11 | *Pseudomonas* sp. RL11 | 14. | *Rhizobium* sp. RLG11 |

TABLE 2B-continued

Sumagro-2 (F2) Genus identification of Cultures Used in Growth-Enhancing Microbial Formulations.*

| F2 Cultures: Revised designation | Revised Genus species designation** | Sumagro 2 (F2) Cultures | Initial Genus species designation from Table 2A |
|---|---|---|---|
| RTRF1 | Rhizobium leguminosarum bv. trifolii RT1 | 2. | Rhizobium trifolii FD |
| RMEL1 | Ensifer (Sinorhizobium meliloti) RM1 | 1. | Ensifer meliloti FD |
| AZOR1 | Azorhizobium caulinodans AZ1 | 3. | Azorhizobium caulinodans KN |
| TV LK | Trichoderma viride LK | 16. | Trichoderma viride LK |
| TV 3116 | Trichoderma viride 3116 | 17. | Trichoderma viride 3116 |
| TVs 3107 | Trichoderma virens 3107 | 15. | Trichoderma virens 3107 |
| TH 3147 | Trichoderma harzianum 3147 | 18. | Trichoderma harzianum 3147 |
| TH LK | Trichoderma harzianum LK | 20. | Trichoderma harzianum LK |
| TH G | Trichoderma harzianum G | 19. | Trichoderma harzianum G |
| TLB 3108 | Trichoderma longibrachiatum 3108 | 21. | Trichoderma longibrachiatum 3108 |

*This group of organisms are the same as shown in Table 2A however for some isolates the Genus was re-assigned based upon DNA identification.
**Identification of bacterial species was confirmed by 16S rDNA sequencing

TABLE 2C

Sumagro-5 (F5; F2A) Genus identification of Cultures Used in Growth-Enhancing Microbial Formulations.*

| F2A (F5) Cultures: Abbreviation | Genus species designation** | As listed for F2 | Initial Genus species designation from Table 2A |
|---|---|---|---|
| RLNG1 | Pseudomonas sp. RL1 | 4. | Rhizobium sp. RLG1 |
| RLNG2 | Pantoea (Enterobacter) agglomerans RL2 | 5. | Azorhizobium sp. RLG2 |
| RLNG3 | Stenotrophomonas maltophila RL3 | 6. | Azorhizobium sp. RLG3 |
| RLNG4 | Stenotrophomonas maltophila RL4 | 7. | Rhizobium sp. RLG4 |
| RLNG5 | Stenotrophomonas maltophila RL5 | 8. | Rhizobium sp. RLG5 |
| RLNG6 | Bacillus subtilis RL6 | 9. | Rhizobium sp. RLG6 |
| RLNG7 | Bacillus subtilis RL7 | 10. | Azorhizobium sp. RLG7 |
| RLNG8 | Pseudomonas sp. RL8 | 11. | Rhizobium sp. RLG8 |
| RLNG9 | Bacillus subtilis RL9 | 12. | Azorhizobium sp. RLG9 |
| RLNG10 | Stenotrophomonas maltophila RL10 | 13. | Rhizobium sp. RLG10 |
| RLNG11 | Pseudomonas sp. RL11 | 14. | Rhizobium sp. RLG11 |
| RTRF1 | Rhizobium leguminosarum bv. trifolii RT1 | 2. | Rhizobium trifolii FD |
| RMEL1 | Ensifer (Sinorhizobium meliloti) RM1 | 1. | Ensifer meliloti FD |
| AZOR1 | Azorhizobium caulinodans AZ1 | 3. | Azorhizobium caulinodans KN |

Exemplary Formulations for Greenhouse Experiments.

The dose per pot in the Greenhouse was proportionally the same as that used in the recommended dose for field applications.

In the Greenhouse, F1 and F2 containing $10^{14}$ microbes/ml were used. One part of F1 or F2 was added to 4 parts of a humate carrier, in particular, Humagro. Pots sizes were 4×5" with a 500 gram soil volume.

Exemplary Formulations for Field Trials.

Five liters of Sumagro microbial formulation containing a total of $10^{11}$ microbial cells [100 billion cells, approximately $2\times10^7$ cells/ml] were used per acre. One liter of Sumagro 1 or Sumagro 2 were mixed with four liters of Humagro and applied per (one) acre.

Control solutions for field trials were the commercial formulation, Nutragro, comprising a microbial mixture. One liter of Nutragro was mixed with 4 liters of Humagro and applied per one acre of soil.

A total of three applications (at least Two) are recommended for one crop season. One at the time of sowing and second application one month after the first application. The foliar application was recommended as a spray at the base of the stem or nearer to the root zone.

3. Preparation of Sumagro-3 and Sumagro-4 in Humagro.

A formulation consisting of 10 bacterial strains and 4 Trichoderma strains was prepared as described for Sumagro 1, and designated Sumagro 3 (F-3). See, Table 3 for microbial strains in Sumagro 3. An additional formulation consisted of seven Trichoderma strains was prepared as described for Sumagro 1 but without adding bacterial strains, see Table 4 for Trichoderma strains in Sumagro 4 (F-4).

TABLE 3A

Sumagro-3 Cultures Used in Growth-Enhancing Microbial Formulations.

| Sumagro 3 | Genus species |
|---|---|
| 1. | Bacillus sp. LK (phosphate-solubilizing bacterium) |
| 2. | Bacillus subtilis LK (phosphate-solubilizing bacterium) |
| 3. | Pseudomonas fluorescens - (stimulates growth by increasing nutrient availability) |
| 4. | Azospirillum - free living diazotroph |
| 5. | Acetobacter sp. LK- free living diazotroph |
| 6. | Rhizobium phaseoli - symbiotic diazotroph |
| 7. | Bradyrhizobium japonicum - symbiotic diazotroph |
| 8. | Rhizobium meliloti FD - symbiotic diazotroph |
| 9. | Rhizobium trifolii FD - symbiotic diazotroph |
| 10. | Azorhizobium caulinodans KN - symbiotic diazotroph |
| 11. | Trichoderma harzianum 3147 |
| 12. | Trichoderma viride 3116 |
| 13. | Trichoderma virens 3107 |
| 14. | Trichoderma longibrachiatum 3108 |

TABLE 4

Sumagro-4 (F2B) Fungal Cultures Used as Mixtures and in Growth-Enhancing Microbial Formulations.

| Sumagro 4 | Abbreviation | Genus Species Name* |
|---|---|---|
| 1. | TH 3147 | Trichoderma harzianum 3147 |
| 2. | TH G | Trichoderma harzianum G |
| 3. | TH LK | Trichoderma harzianum LK |
| 4. | TV 3116 | Trichoderma viride 3116 |
| 5 | TV LK | Trichoderma viride LK |
| 6. | TVs 3107 | Trichoderma virens 3107 |
| 7. | TLB 3108 | Trichoderma longibrachiatum 3108 |

*identified as described herein.

Exemplary characterizations of microbial isolates for use in providing basic nutrients in formulations of the present inventions.

Nitrogen Fixation Tests: The inventors evaluated bacterial isolates of the present inventions for their capability to fix free Nitrogen (atmospheric nitrogen). For this example, bacterial isolates were plated onto nitrogen-free glucose medium. Capability for growth on this medium indicated that the organism was able to fix nitrogen. Exemplary results are shown in Table 5.

Phosphate Solubilization tests: Phosphate solublizing Bacteria (PSB) were identified by visual observation of bromophenol blue production using NBRI-BPB growth medium (for example, methods in Curr Microbiol. 2001 July; 43(1): 51-6, herein incorporated by reference).

TABLE 5

Identification of free Nitrogen fixing and Phosphate Soluabilizing Bacteria Isolates of the present inventions.

| F2 CULTURES (Strain) | Growth on minus Nitrogen broth medium* | Blue color produced on NBRI-BPB growth medium for indicating Phosphate Solubilization** |
|---|---|---|
| RLNG1 | ++/+ | − |
| RLNG2 | −/− | − |
| RLNG3 | −/− | − |
| RLNG4 | −/− | − |
| RLNG5 | +/+ | + |
| RLNG6 | +/+ | − |
| RLNG7 | +/+ | − |
| RLNG8 | +/+ | − |
| RLNG9 | ++/+ | + |
| RLNG10 | +/++ | + |
| RLNG11 | +/+ | − |
| R. TRIFOL | +/++ | − |
| R. MELI | ++/++ | − |
| AZORHIZO | ++/++ | − |

*−/− = no growth, +/+ indicates a very low level growth thus of nitrogen fixation, any combination of +/++ and ++/+ indicates a moderate level of nitrogen fixation, while ++/++ indicates a high level of nitrogen fixation.
**− indicates no blue production while + indicates blue color production.

4. Preparation of Microbial Formulations in Mineral Solution Carriers.

a. Microbial Formulations with Mineral Solutions.

The inventors further tested their microbial formulations using an exemplary mineral based carrier solution.

Preparation of 1 Liter of a working mineral solution (MM) was made by the addition of 50 ml of Macro-A, 50 ml of Macro-B stock solutions and 1 ml of the trace element stock solution with the volume brought up to 1 Liter. The following stock solutions used for these formulations were prepared individually as a 10× concentration stock solution in double distilled water and sterilized by autoclaving. Macro-A: $NH_4NO_3$ 1.0 g/L, $KH_2PO_4$ 0.3 g/L, $K_2HPO_4$ 0.3 g/L, $MgSO_4.H_2O$ 0.1 g/L, $Ca(NO_3)_2.4H_2O$ 0.05 g/L. Macro-B: KCl 0.5 g/L, $KH_2PO_4$ 0.2 g/L, $MgSO_4.H_2O$ 0.2 g/L, and $CaSO_4.2H_2O$ 0.2 g/L. Trace Element Stock Solution: $H_2BO_3$ 1.0 mg/L, $ZnSO_4.7H_2O$ 1.0 mg/L, $CuSO_4.5H_2O$ 0.5 mg/L, $MnCl_2.4H_2O$ 0.5 mg/L, $Na_2MoO_4.2H_2O$ 0.1 mg/L, and Fe-EDTA 1.0 mg/Liter.

Microbial solutions of the present inventions, Sumagro 1-4, were then prepared using Mineral solution (MM) as a carrier. In some formulations, MM was added at the same volume as HG, described herein for direct comparative experiments. As such, comparative experiments were done where duplicate formulations were prepared and used at equal volumes where HG was the carrier in one case and MM is the carrier in the parallel treatment. The results obtained with F2 using MM as the carrier were comparable to those of F2 with HG as the carrier. Therefore, the inventors concluded that these preliminary results showed that HG was not an essential ingredient (carrier) and that it can be replaced with suitable alternative carriers, such as a mineral solution.

b. Microbial Formulations with Nitrogen-Free Mineral Salt Solutions (Sterilized):

$CoCL_2.6H_2O$ 0.004 mg, $H_3BO_3$ 2.86 mg, $MnCL_2.4H_2O$ 1.81 mg, $ZnSO_4.7H_2O$ 0.22 mg, $CuSO_4.5H_2O$ 0.08 mg, $H_2MoO_4.H_2O$ 0.09 mg, $MgSO_4.7H_2O$ 492.96 mg, $K_2HPO_4$ 174.18 mg, $KH_2PO_4$ 136.09 mg, $CaCL_2$ 110.99 mg, $FeC_6H_5O_7.H_2O$ 5.00 mg, and distilled water up to 1000.00 ml. pH was adjusted to 6.8 as needed with sterile NaOH and HCl. (Reference: Canadian Food Inspection Agency-Fertilizers-Methods for testing legume inoculants, in Methods for Testing Legume Inoculant and Pre-Inoculated Seed Products Fertilizers Act, Section 23, Regulations, PLANT PRODUCTION DIVISION, Canadian Food Inspection Agency, Ottawa, Ontario, K1A 0Y9, Canada, Latest Revision: May, 2005, www.inspection.gc.ca/english/plaveg/fereng/legumee.shtml, herein incorporated by reference).

A broad range of test plants were used in the following greenhouse growth experiments and field trials. These plants included but were not limited to a broad spectrum of plants including legumes, cereals, noncereals, vegetables, and forage crops *Zea mays* (corn), *Sorghum bicolor* (sorghum), *Glycine max* (soybean), *Phaseolus vulgaris* (garden bean), *Pisum sativum* (pea), *Phaseolus* sp. (wonder bush bean), *Arachis hypogea* (peanut), *Oryza sativa* (rice), *Lycopersicon esculentum* (tomato), *Solanum melongena* (eggplant), *Hibiscus esculentus* (okra), and *Cucurbita maxima* (squash), cow pea (*Vigna sinensis*), green gram (*Vigna radiata*), black gram (*Vigna mungo*) zucchini (*Cucurbita pepo*) and a variety of grasses as shown herein.

EXAMPLE II

Greenhouse Experiments Using Sumagro 1 and 2

The relative efficacy of Sumagro 1 and Sumagro 2 were tested in lab scale experiments done in a greenhouse with standard controlled temperature and humidity. NutraGro, a commercially available microbial product with claimed plant growth enhancing properties was used in parallel on duplicate pots of plants for comparison. No exogenous nitrogen fertilizer or pesticides were added in these experiments.

Procedures:

Sumagro 1 (F1) and Sumagro 2 (F2) described in the preceding sections were used. F1 and F2 contained 1014 microbes per ml. For Sumagro 1, one part of F1 was added to 4 parts of Humate carrier (12% humic acid in water as mentioned above). For Sumagro 2, one part of F1 was added to 4 parts of Humate carrier (12% humic acid in water as mentioned above). Pots (size 4"×5" and 500 g soil volume) were used for the initial Greenhouse experiments. If the experiment is continued beyond two months, then the plants were transferred to pots with 9" diameter and 12" depth. Enough water was added to just keep the soil moist (approximately 150 ml for the small pots).

Pots prepared as above were used to plant the seeds [or seedlings] depending on the crop. Tomato, eggplant, and okra seeds were germinated in pot mix soil using 4"×5" inch pots and 15-day-old seedlings from these pots were used for transplantation. For each pot, 4 seeds/seedlings were planted and for each treatment two randomized replications were made.

Initial Greenhouse treatments included the following: 1. F1 plus Humagro; 2. F2 plus Humagro; 3. Nutragro plus Humagro; and 4. Humagro.

Seeds of all legumes and cereals were imbibed in double distilled water for 12 hr before soaking them in various formulations for 30 min. just before sowing.

Concentration of Formulations to add per pot was calculated for 500 gram of soil in each pot. Each pot received 4 ml of a formulation and this gave approximately $10^{14}$ organisms per each treatment. [Note: The inventors diluted and tested this formulation at a $10^{10}$ organism per treatment that demonstrated similar growth enhancement results on treated plants]. One week after planting, all purpose fertilizer with an N:P:K of 15:30:15 (300 mg/pot) was added to each pot as calculated based on blanket recommendation for fertilizers. Pots were watered to maintain adequate moisture levels.

Two applications of the treatments were given: one at the time of planting and the second one 30 days after sowing/planting. A pipette was used to introduce the formulations at the base of the stems. The duration of the experiment extended up to three months in some cases. Water was added as needed to maintain 80% field moisture capacity. Parameters used for evaluating the efficacy of the formulations included any changes in: seed germination, seed emergence, height of the plant, leaf area, shoot length, root length, nodulation (legumes only), shoot weight, root weight, time for flowering, and fruiting and disease incidence. Parameters were measured at approximately four-week intervals.

Plants used in Experiment 1 was started in the growth chamber under controlled conditions of temperature and humidity. The pots were small and contained 40 g of soil. These plants were then transferred to larger pots for placement in the greenhouse. At the time of transfer, plants were transferred to larger pots containing 500 g of soil. The formulations tested were 1. A=HG+F1; 2. B=HG+F2; 3. C=HG+NG; and 4. D=CONTROL (NO TREATMENT). Abbreviations: HG—Humagro; F1—Sumagro 1: F2—Sumagro 2; NG—Commercial microbial formulation. For each treatment there were two replications. The crop plants tested were 1. Corn; 2. Purple hull-pea; Tomato; Brinjal (eggplant); Soybeans; Wonder bush beans; Garden pea; Zucchini; and Squash plants.

Experiment 1 results demonstrated plant growth enhancer capability of both F1 and F2 formulations of the present inventions. In particular, the greatest growth enhancement was seen of purple hull-pea, tomato, brinjal (eggplant), soybean, wonder bush bean, and garden pea plants treated with F2 (Formulation 2) F1, such that these plants were taller and/or bushier than similar plants treated with F1 (formulation 1), which showed more plant enhancement than Nutragro, which was in turn slightly better than plants treated with Humagro or control plants treated with water, see, FIGS. 2-10, especially after 2 months of growth, see FIG. 4. Specifically, plant growth was assessed by plant height and total leaf area of the plants. FIGS. 2-10 clearly demonstrate the greater performance of Formulation 2 and 1 over Nutragro on similar plants. Early flowering and more number of flowers were also observed with wonder bush beans.

Plants used in Experiment 2 were seeded and grown under greenhouse conditions from the time of sowing. In Experiment 2, a 'Humagro only' control was also included in addition to the four treatments shown in Experiment 1. Further, rice, sorghum, okra and peanuts plants were included in addition to the plants tested in Experiment 1.

Experiment 2 results further demonstrated plant growth enhancing capabilities of F1 and F2, as in Experiment 1, such that growth of plants treated with either F1 or F2 outgrew, either in height, width or both, those plants treated the Nutragro and or Humagro (no additives), see, exemplary FIGS. 11-14.

Greenhouse Evaluation Experiments.

Baccto premium potting soil (Michigan peat Company, Houston, Tex.) was used for growing the selected test plants in the greenhouse experiments. A randomized replicated design was used to set up growth experiments for testing the efficacy of F1 and F2 formulations. For each 12"×12"×12" pot, two split applications of the liquid formulations ($10^{10}$ cfu per pot) were given during the crop period. The first application was given as soil treatment at the time of sowing and the second application was given at the base of the plant one month after the first application. The experiments were set up in such a way to compare the efficacy of F1 and F2 formulations in comparison to a control (HG) containing 12% humic acid alone without any added microbes. Hence, 3 treatments, i.e. F1, F2, and control (HG), each with 4 replications were tested. Exogenous fertilizers or pesticides were not added to any of the three treatments during the crop period. The majority of inoculant standards contain a minimum number of viable microbial cells of at least $10^9$ rhizobia/gram soil (Brockwell and Bottomley, 1995; Xavier et al. 2004; herein incorporated by reference). Plant minerals (minus N) were added to each treatment 15 days after germination. A broad spectrum of crops which includes cereals, vegetable crops, legumes, forage grasses and also biofuel grasses were tested. Plants including garden beans, wonder bush beans, purple hull beans, pea, cowpea, green gram, black gram, soybean, tomato, eggplant, okra, squash, zucchini (*Cucurbita pepo*), corn, sorghum, rice, and peanut were tested to compare the efficacy of F1 and F2 in enhancing productivity. Observations were made at monthly intervals during the entire crop period. In a separate experiment, the efficacy of F1 and F2 on germination and growth of commercially available forage legumes seed mixture (Tecomate Monster Seed Mix, Todd Valley Farms, Nebraska) was tested. Plant height, total number of leaves, leaf area, leaf color, flowering time, fruiting time, shoot and root biomass, and the incidence of pests and diseases were monitored.

The results (Table 6, FIG. 21 to 24) showed a significant increase in plant height with F2 treatment followed by F1 and control. For example, when compared to controls, corn height increased by 65%; egg plant 41%; wonder bush beans 40%; tomato 91%, soybeans 96%, pea purple hull 50%, and okra by 16%. Yield also significantly increased in F2 treatment. For example, mean yield of tomato increased by 88% as compared to the control. Okra yield increased 50% and rice increased by 40%. With rice, both F1 and F2 showed an increase in seedling vigor, plant height, number of tillers and their carry over effect on grain yield. Legumes tested showed early flowering and fruiting, good root nodulation, and no disease was observed in both the experimental and control plants during the crop period.

Figure 25A:
FIG. 25 shows an exemplary comparison of growth observed in a mixture of potted grass plants (commercial forage seed mixture Tecomate Monster Mix) treated with Mineral solution (MM), HG (F2 prepared in a carrier of HG; F2+HG), NF2 (F2 prepared in a carrier of mineral solution (MM) in place of HG). HG=Humagro; F2=Sumagro 2.
Figure 25B:
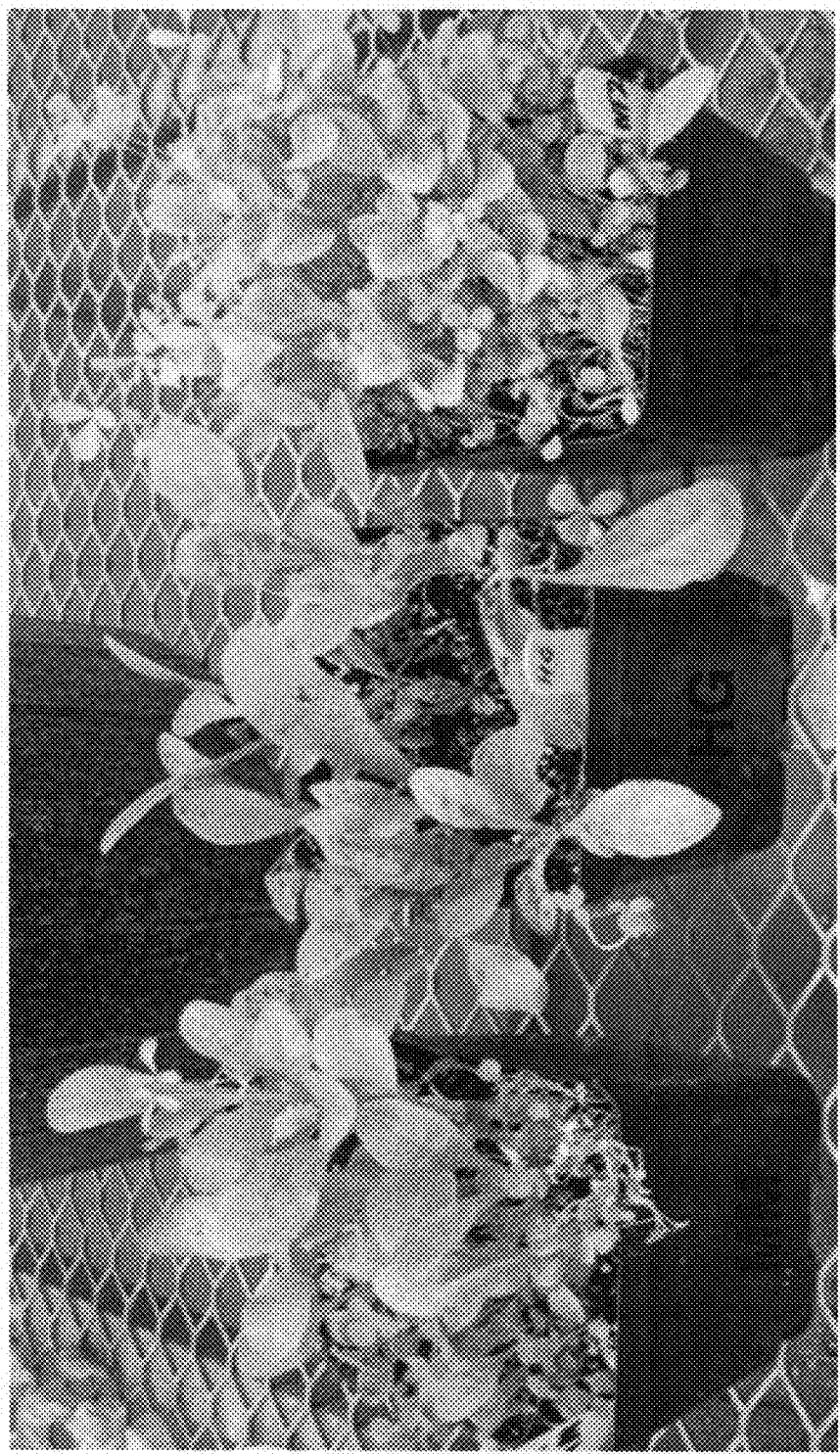
Figure 26:
FIG. 26 shows an exemplary dramatic increase in growth of clover plants A) grown with F2 treatments as compared to B) control plants without treatments.
Figure 27A:
FIG. 27 shows an exemplary growth enhancing effect of formulations of the present inventions on several types of switch grass plant varieties A) Carthage, B) Cave-in-Rock C) Forestburg and D) Dacotah (Dakota).
Figure 27B:
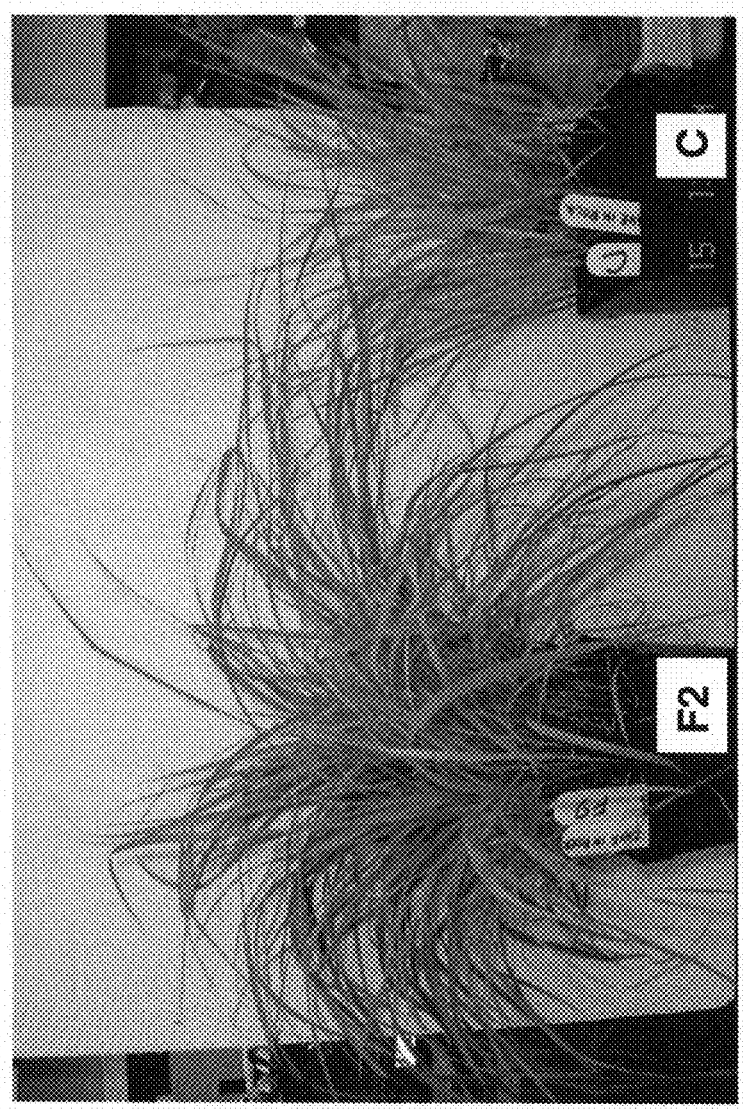
Figure 27D:
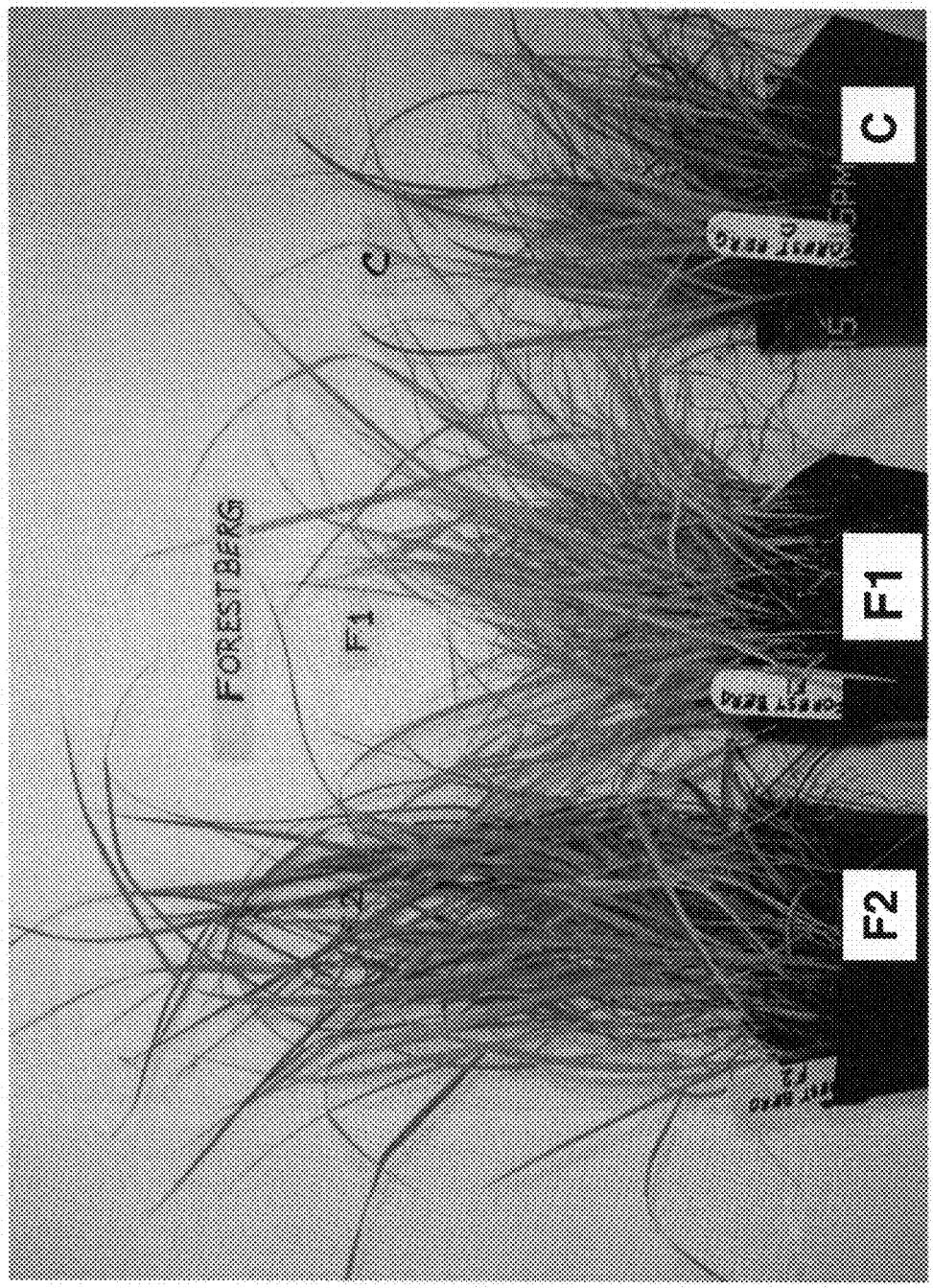

There is a significant commercial interest in products that substantially increase productivity of forage crops. The present results further confirm that F2 formulation enhances the growth of a commercial seed mixture of forage crops, i.e. Tecomate Monster Mix, clover and switch grass, as compared to humate alone as control (FIGS. 25-27).

TABLE 6

Greenhouse evaluation of polymicrobial formulations F1, F2, and control (C).

|  | Plant Height [cm] | | | Yield [g] | | |
|---|---|---|---|---|---|---|
| Crop | F2 | F1 | C | F2 | F1 | C |
| Corn | 142 | 125 | 101.2 | — | — | — |
| Sorghum | 74 | 68.5 | 49 | — | — | — |
| Rice | 65 | 60 | 55 | 20.85 | 15.76 | 5.2 |
| Tomato | 77 | 72 | 66 | 1900* | 755* | 380 |
| Soybeans | 167.7 | 160.5 | 98 | 11.58* | 7.9 | 5.1 |
| Pea | 45 | 38 | 33 | 13.99* | 10.48* | 7.52 |
| Okra | 130 | 93.7 | 98 | 138.7* | 100* | 38.7 |
| Peanut | 42 | 42 | 35 | 21.62* | 14.67* | 6.48 |
| Pea purple hull | 60.96 | 46.48 | 40.64 | 14.75* | 12.23* | 10.75 |
| Garden beans | 135 | 128 | 102 | 48.6* | 42.6* | 23.5 |
| Wonder bush beans | 88.9 | 76.2 | 63.5 | 72.9* | 63.6 | 35.6 |
| Squash | 57 | 41 | 36 | 650* | 230* | 0 |

Significant, P = 0.022

EXAMPLE III

Field Trials Demonstrating Plant Growth Enhancement of Sumagro 1 and Sumagro 2

The primary objective was to compare the efficacy of the microbial growth enhancement formulations of the present inventions with one of the microbial products, claimed to be a plant growth enhancer, such as a product claimed to be a plant growth enhancer that is already in commercial use. The commercial product selected for comparison was Nutragro, see above.

Field Trial Applications (Procedure):

Step 1. Concentrated Sumagro 1 (F1) and Sumagro 2 (F2) as described in the preceding sections were prepared and used for these trials, such that F1 and F2, respectively, contained $10^{17}$ and $10^{15}$ microbes per ml.

Step 2. One liter of concentrated F1 or F2 was added to 4 liters of Humagro (a commercial humic acid carrier) and this 5 liter F1 Mix or F2 Mix was further mixed with irrigation water and applied to one acre of land.

At least 2 applications were applied by irrigation water for one crop season.

Step 3. A first application was applied to soil at the time of sowing the seeds. Second application was given before flowering (approximately 30 days after sowing, depending on the crop). The inventors recommended application of the formulation at the base of the plants so that the formulation can infiltrate into the soil more effectively in proximity to the plant's root system. A third application (when given) was applied as a foliar spray approximately 30 days after flowering.

Standard agronomical practices such as appropriate soil tilth, pH, irrigation, and a low level of fertilizer (such as N:P:K of 10:10:10), etc. were adhered to during the field experiments.

Step 4. The field experiments were designed according to a standard randomized block design with buffer zones of 2 feet on either side of each block, in part to prevent edge effects of spray drift. Each treatment block of a 10 feet square block was duplicated, such that 2 replicates per treatment were provided. The treatments included the following four: 1. F1; 2. F2; 3. Nutragro; and 4. Humagro.

Test crops treated with formulations of the present inventions included vegetable plants, such as tomato, brinjal, okra, squash, and zucchini; legume plants, such as beans, pea; cereal plants, such as rice, corn, and sorghum; fodder crop plants, such as alfalfa, Bermuda grass, and clover; fiber crop plants, such as cotton, and oil seed plants, such as peanut plants.

Step 5. Main test parameters were evaluated to compare the efficacy of F1, F2 and controls, including seed germination (percent), height of the plant, equivalent leaves for leaf area measurements, shoot length, root length, nodulation (legumes only), shoot weight, root weight, time for flowering, and fruiting and disease incidence (if any). Parameters as described herein, were evaluated at day 30 and at day 60 after sowing.

Field Evaluation Experiments.

Field trials were conducted with the cooperation of BioSoil Enhancers (Hattiesburg, Miss.) to test the efficacy of the polymicrobial formulations on soybean, corn, cotton, yellow squash, tomato, green beans, bell pepper (*Capsicum annuum*) and banana pepper (*Capsicum* spp.). The yield data obtained in field trials were consistent with results of greenhouse experiments in showing a distinct increase in yield of all the crops tested. For example, crops treated with polymicrobial formulation F2 showed 75% increase in yield for tomatoes; 27% for bell peppers; 40% for banana peppers; and 61% for yellow squash (Table 7). Increase in corn yield was 30.0% and cotton plants treated with the polymicrobial formulation also showed increased plant height, good branching, and large sized healthy bolls when compared to control (results not shown). Both greenhouse and field trials indicate that appropriately formulated polymicrobial formulations have excellent potential to enhance productivity of a broad spectrum of crops. Moreover, the need for nitrogen fertilizers and pesticides greatly decreased, which substantially contribute to the conservation of soil health, and conservation of fossil fuel energy sources. Further research progress in this area would be a substantial contribution to boosting crop production compatible with sustainable agriculture practices.

TABLE 7

Field Evaluation of Polymicrobial Formulations.

| Crops | F2 formulation (oz per acrea) | F1 formulation (oz) | Control (oz) | F2 - % increase in yield over control |
|---|---|---|---|---|
| Squash | 1559 | 1414 | 963 | 61 |
| Tomato | 836 | 514 | 477 | 75 |
| Banana Pepper | 35 | 15 | 25 | 40 |
| Bell Pepper | 102 | 87 | 80 | 27 |

The estimated cost per acre for use of these products is less than $1.00 per acre. No exogenous nitrogen fertilizer or pesticides were added in these experiments.

EXAMPLE IV

This example demonstrates the effects of F2, F3 and F4 on root nodule formation. Unless specified, the soil was not sterilized. However for certain experiments the inventors grew plants in sterilized soil in order to demonstrate the endogenous characteristics of the microbes of the formulations of the present inventions, such as nodule formation capabilities of the microbial formulation. Soil was sterilized by autoclave until test samples showed that no endogenous growth was observed after watering and observation.

The inventors provided solutions of F2, F3 (a Rhizobial bacterial Mixture) and F4 (consisting of *Trichoderma* strains) nodulation experiment. The results demonstrated numerous root nodules in bean plant roots during F2 treatment, FIG. 15D, as compared to the few nodules observed on untreated bean plant roots, FIG. 15E. These nodules were shown to be the direct result of microbes in the F2 formulation when compared to the greatly reduced number and variety of nodules in bean plants grown in sterilized soil (FIG. 15C).

The inventors provided solutions of F2, F3 (a *Rhizobial* bacterial Mixture) and F4 (consisting of *Trichoderma* strains) nodulation experiment. The results demonstrated numerous root nodules in bean plant roots during F2 treatment, FIG. 15D, as compared to the few nodules observed on untreated bean plant roots, FIG. 15E. These nodules were shown to be the direct result of microbes in the F2 formulation when compared to the greatly reduced number and variety of nodules in bean plants grown in sterilized soil (FIG. 15C).

Because the inventors observed increased root nodule formation in leguminous plants treated with an F2 formulation of the present invention, see, above, the inventors further treated legume pea plants with formulations where the microbes were either bacterial or fungal microbes in order to separate the bacterial and fungal contributions.

Therefore, the inventors provided a formulation consisting of the Symbiotic Diazotroph bacteria described herein, and a formulation consisting of five *Trichoderma* species of the present inventions (F4) *Ensifer meliloti* FD, *Rhizobium trifolii* FD, *Azorhizobium caulinodans* KN, *Rhizobium phaseoli* CA, and *Bradyrhizobium japonicum*.

Figure 15A:
FIG. 15 shows exemplary root nodules from Garden Bean plants (*Rhizobial noculum* comparisons) A) Plants treated with F3 formulation (*Rhizobial inoculum*); B) Plants treated with F4 formulation, Note that F4 formulation consisting of *Trichoderma* fungi only (which are non-nitrogen fixers) induced diverse type of nodule formation as shown in A by indigenous nitrogen-fixing bacteria on the roots of Garden Beans; C) bean plants grown in sterile soil treated with F2 showing modest levels of nodulation as compared; D) Plants grown in unsterile soil treated with F2; to E) bean plant roots from bean plants grown in sterile soil without F2 treatments. Plants were treated with a formulation (or untreated for controls) of the present invention according to methods described in Example 1.
Figure 15B:
Figure 15C:
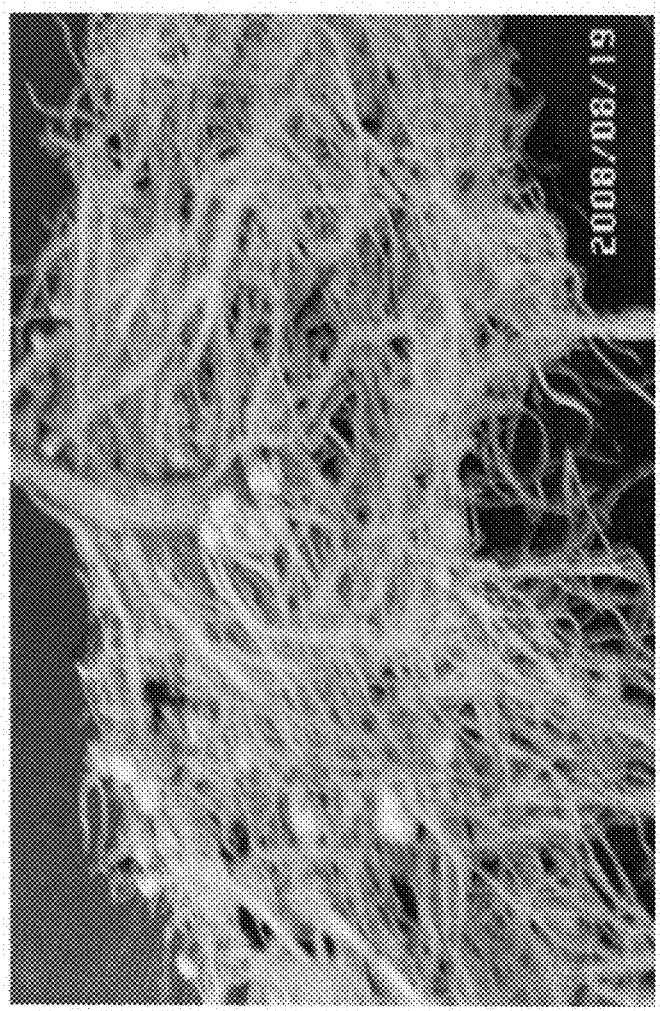
Figure 15D:
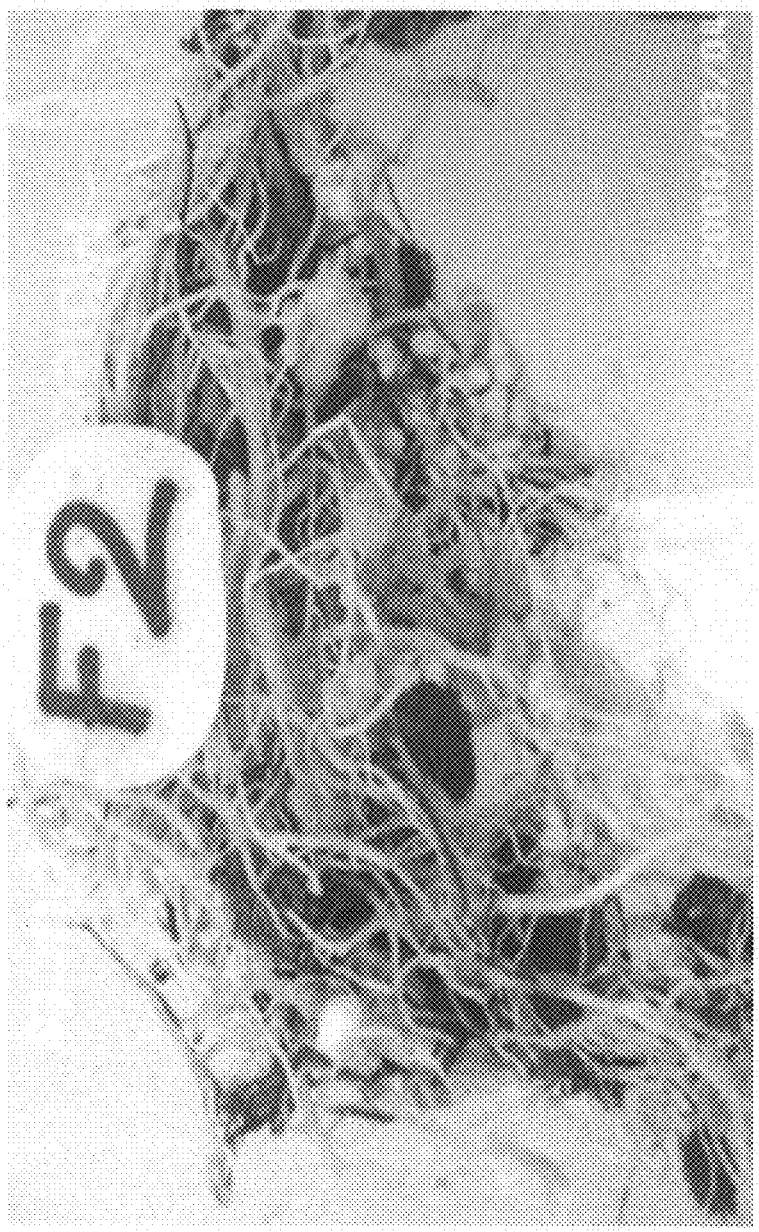
Figure 15E:
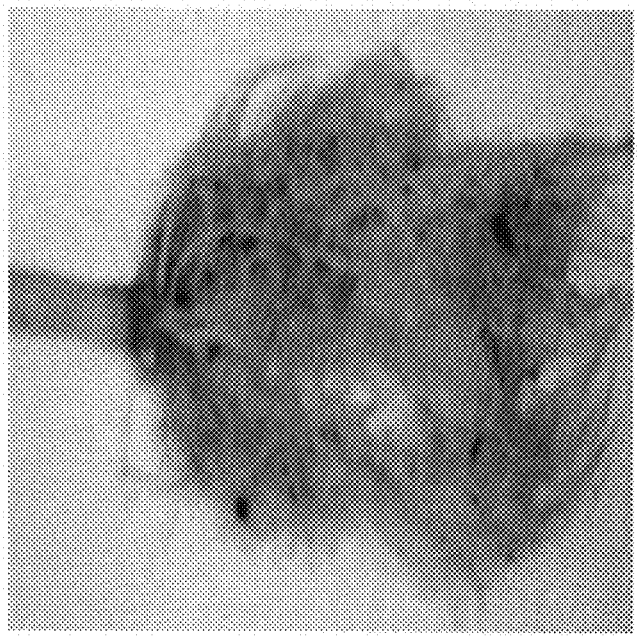
Figure 17:
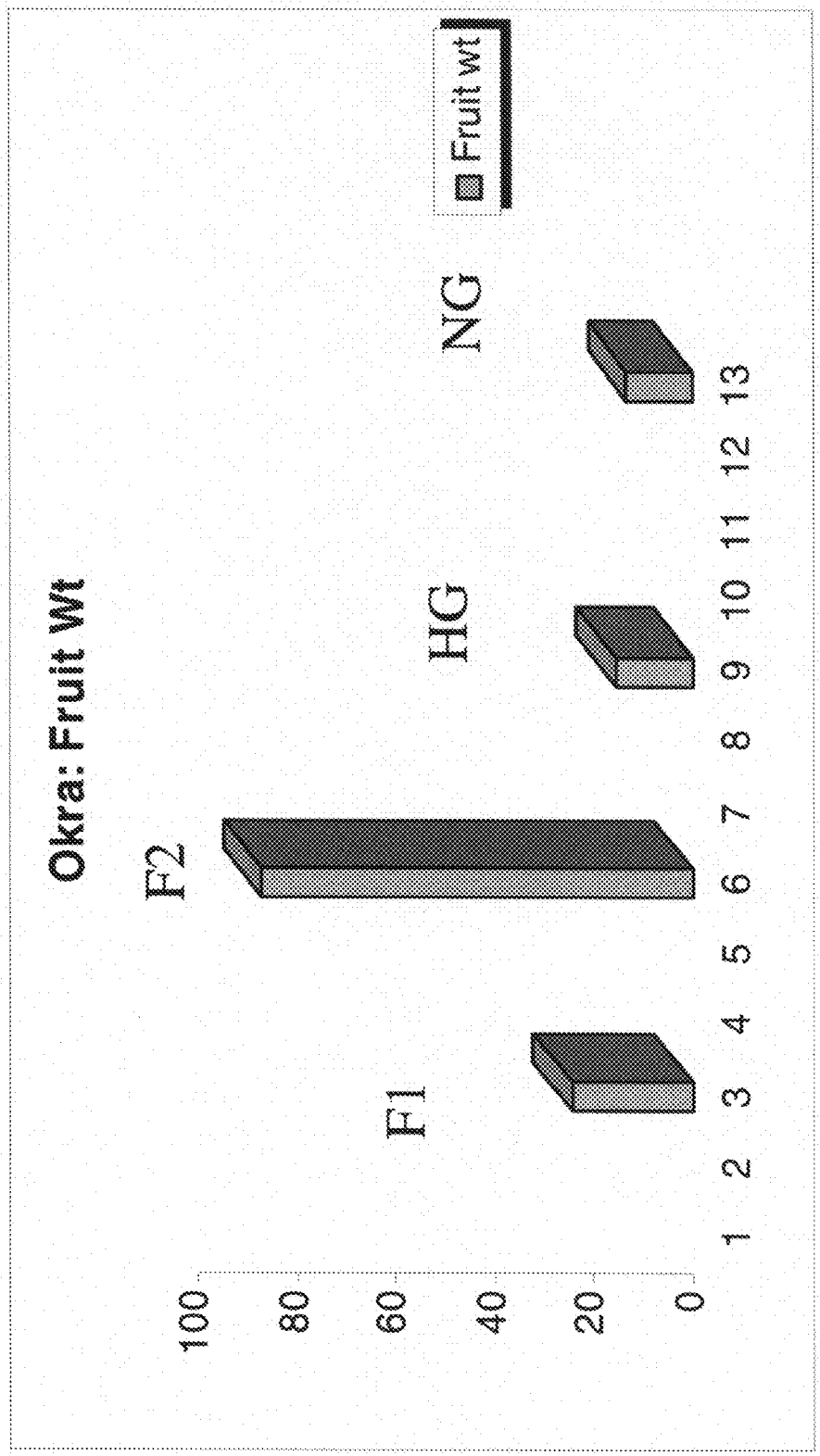
FIG. 17 shows an exemplary okra fruit weight from a field trial. F1=Sumagro 1; F2=Sumagro 2; HG & NG=Humagro & Nutragro; and C=control treatments.
Figure 18:
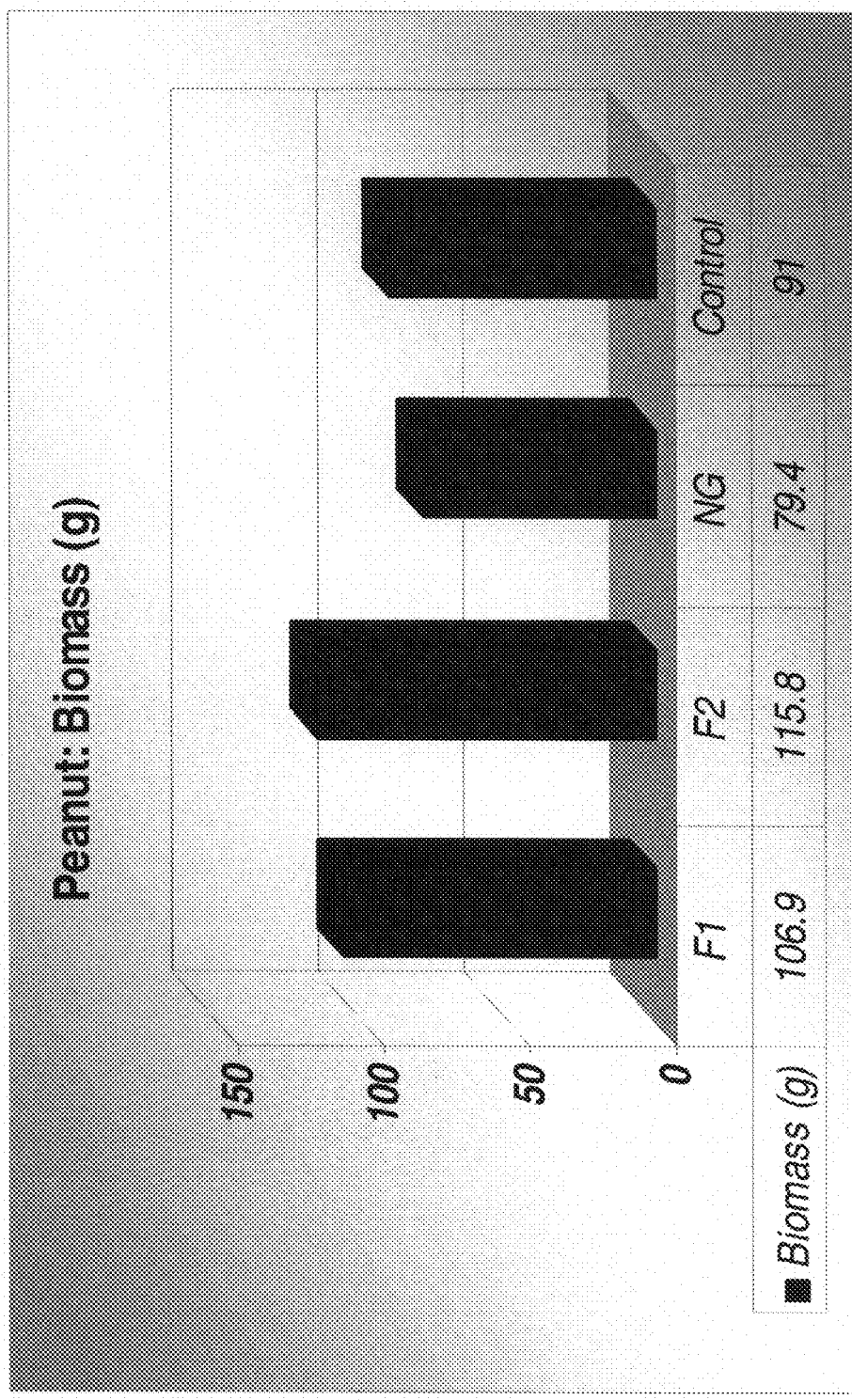
FIG. 18 shows an exemplary peanut biomass from a field trial. F1=Sumagro 1; F2=Sumagro 2; HG & NG=Humagro & Nutragro; and C=control treatments.
Figure 19:
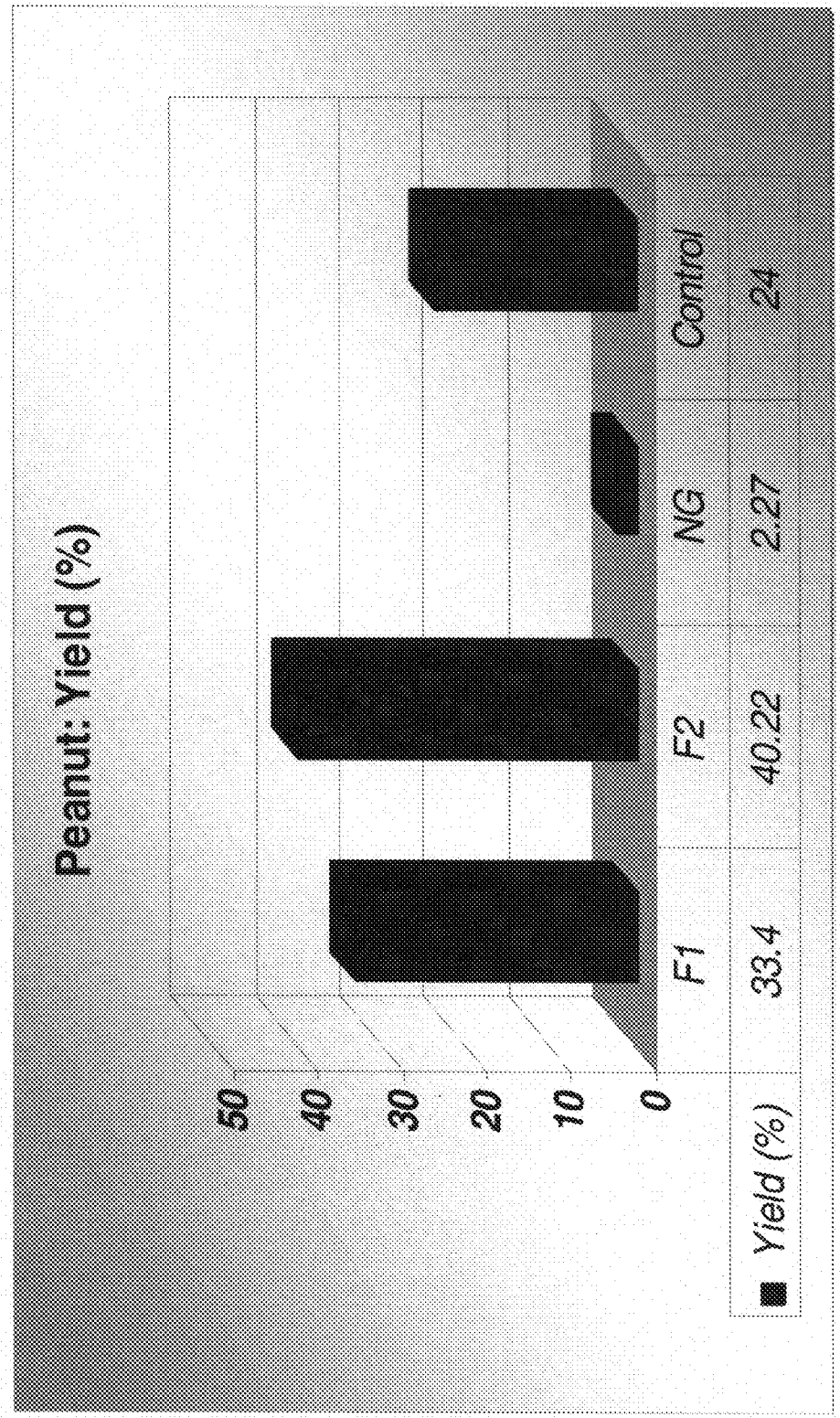
FIG. 19 shows an exemplary peanut plant yield from a field trial. F1=Sumagro 1; F2=Sumagro 2; HG & NG=Humagro & Nutragro; and C=control treatments.
Figure 20:
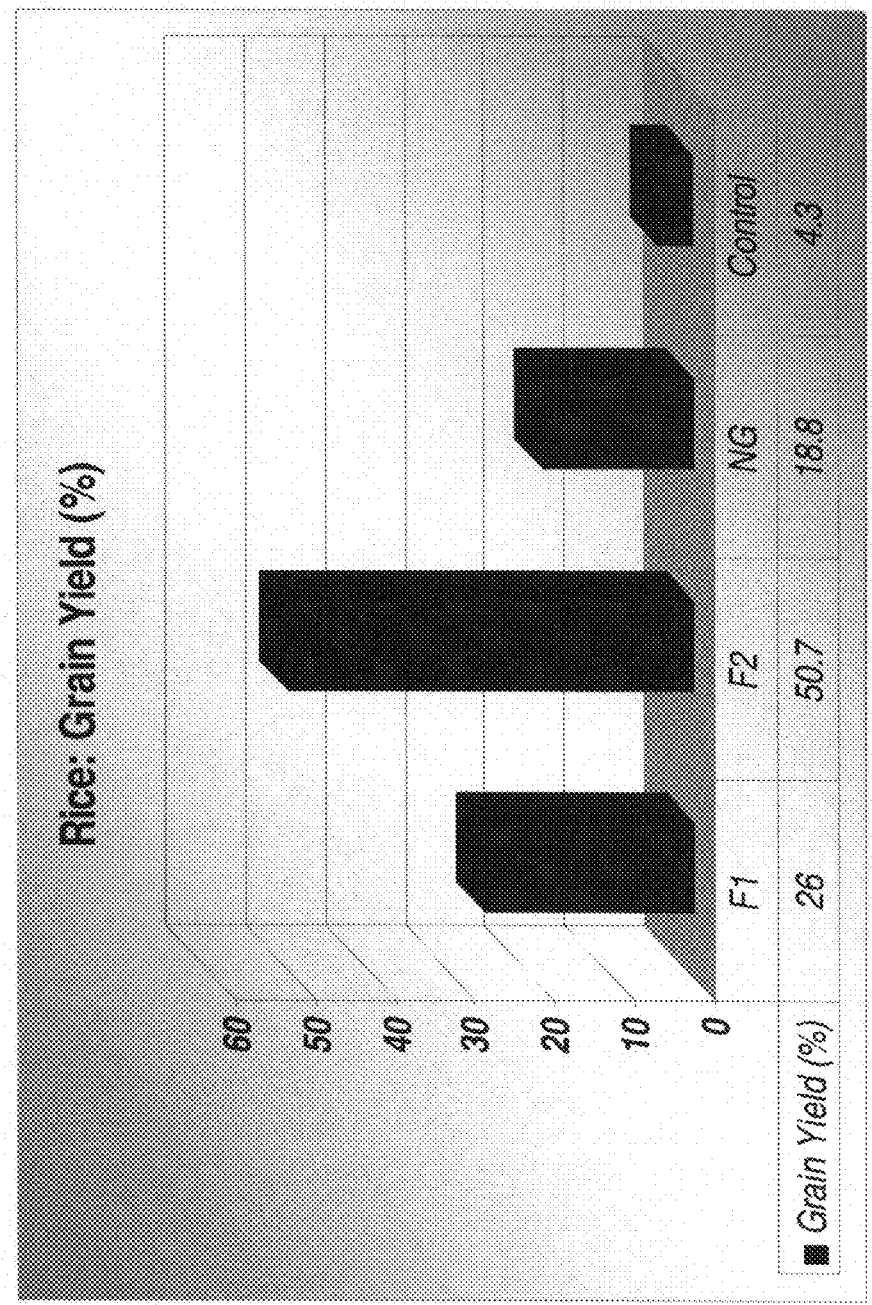
FIG. 20 shows an exemplary rice plant yield from a field trial F1=Sumagro 1; F2=Sumagro 2; HG & NG=Humagro & Nutragro; and C=control treatments.
Figure 21A:
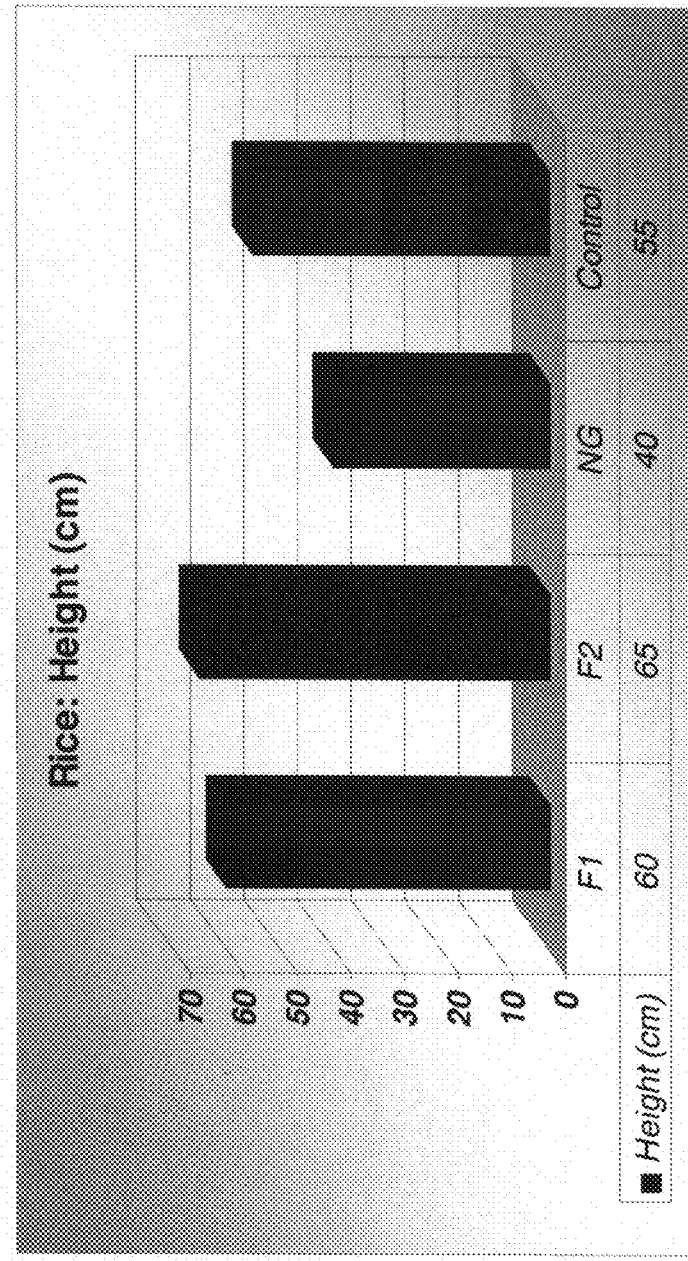
FIG. 21 shows an exemplary comparison of rice plant height A) from a field trial, and grown under Greenhouse Evaluation conditions B) plant height and C) yield of rice grown in the presence of polymicrobial formulations F1 and F2 as compared to a control with no formulation added. F1=Sumagro 1; F2=Sumagro 2; HG & NG=Humagro & Nutragro; and C=control treatments.
Figure 21C:
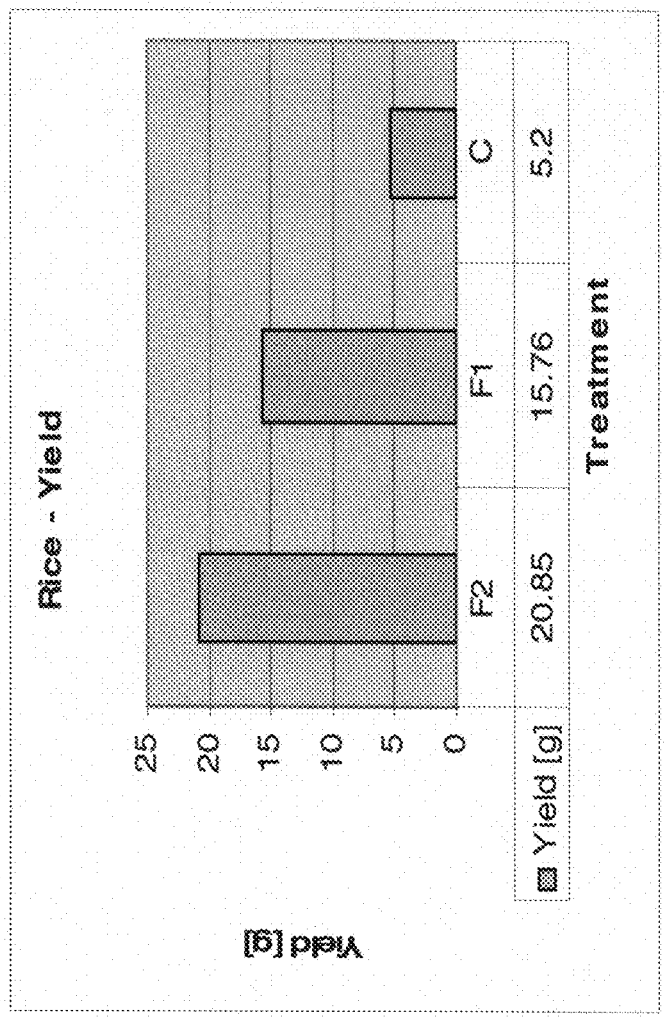
Figure 22C:
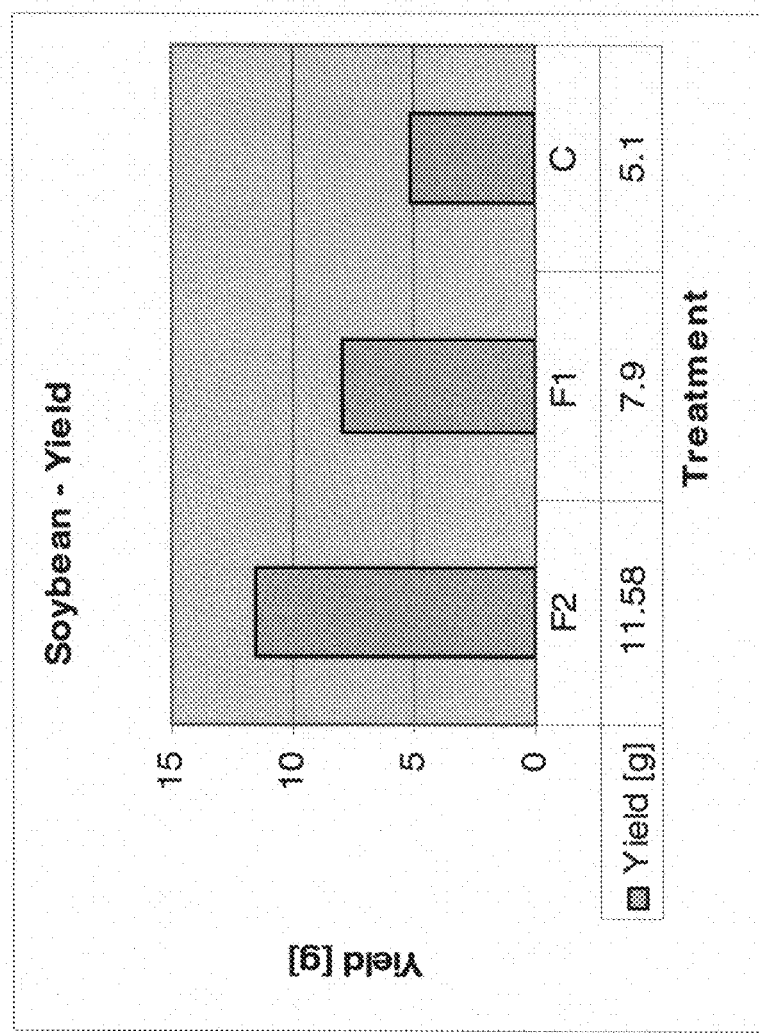
FIG. 22 shows an exemplary comparison of soybean plant A) biomass from a field trial and grown under Greenhouse Evaluation conditions plant height B) and yield C) of soybean plants grown in the presence of polymicrobial formulations F1 and F2 as compared to a control with no formulation added. F1=Sumagro 1; F2=Sumagro 2; HG & NG=Humagro & Nutragro; and C=control treatments.
Figure 23A:
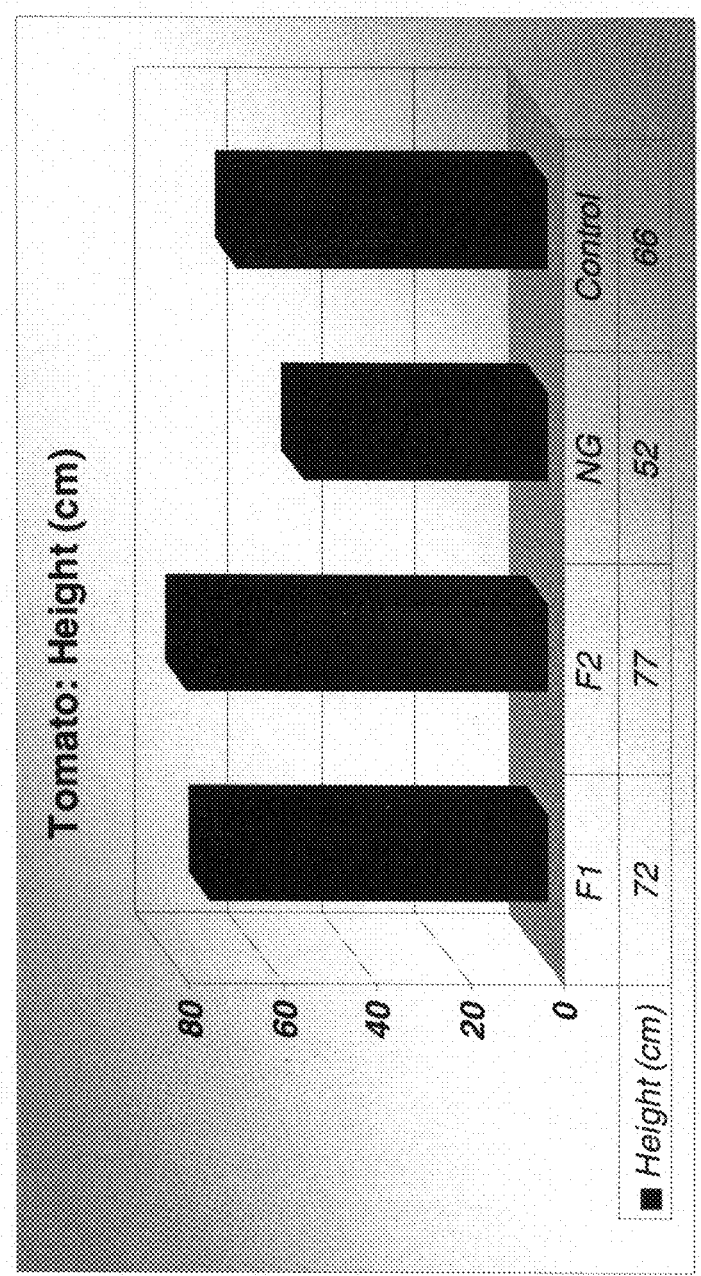
FIG. 23 shows an exemplary comparison of A) tomato plant height from a field trial and grown under Greenhouse Evaluation conditions plant height B) and yield C) of tomato grown in the presence of polymicrobial formulations F1 and F2 as compared to a control with no formulation added under Greenhouse Evaluation conditions. F1=Sumagro 1; F2=Sumagro 2; NG=Nutragro; and C=control treatments.
Figure 23B:
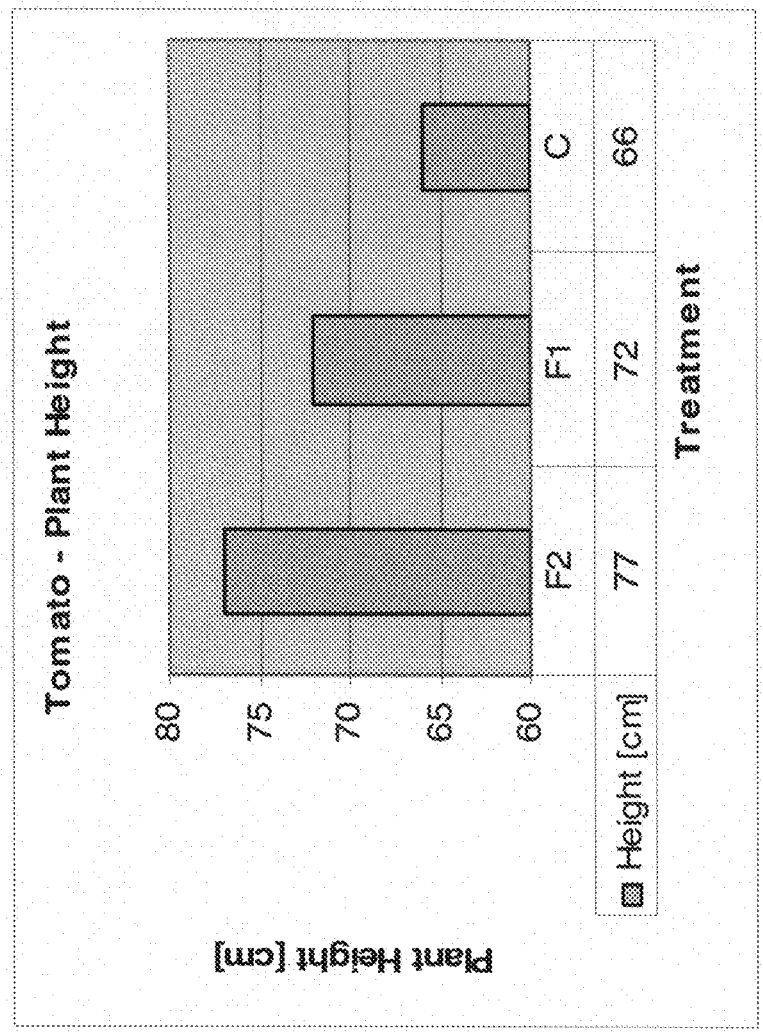
Figure 23C:
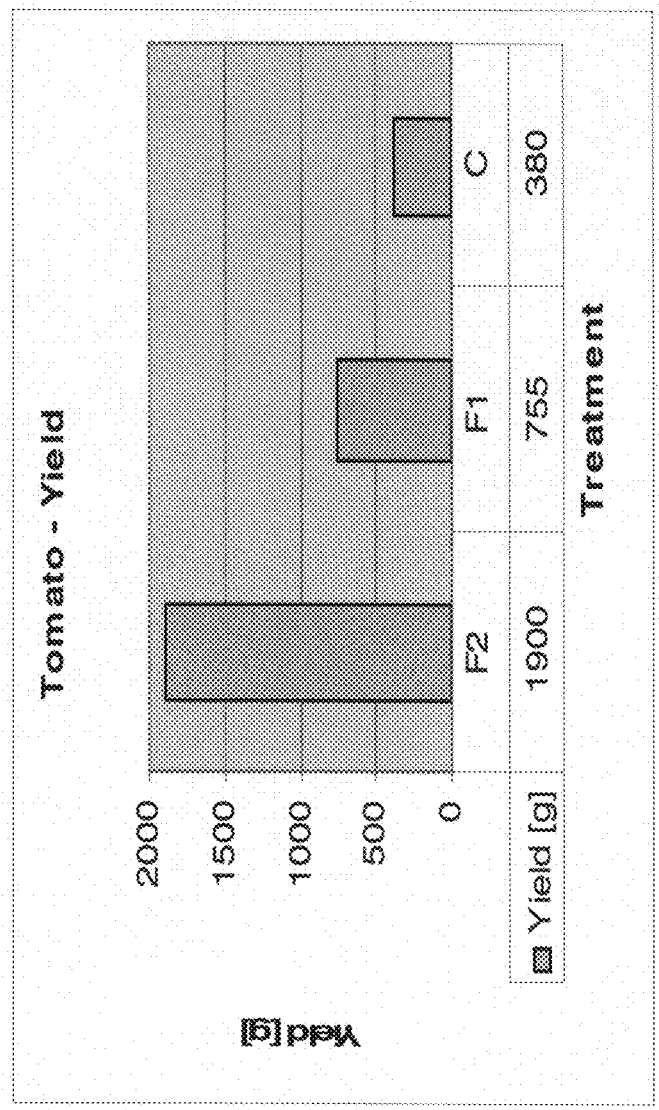
Figure 24:
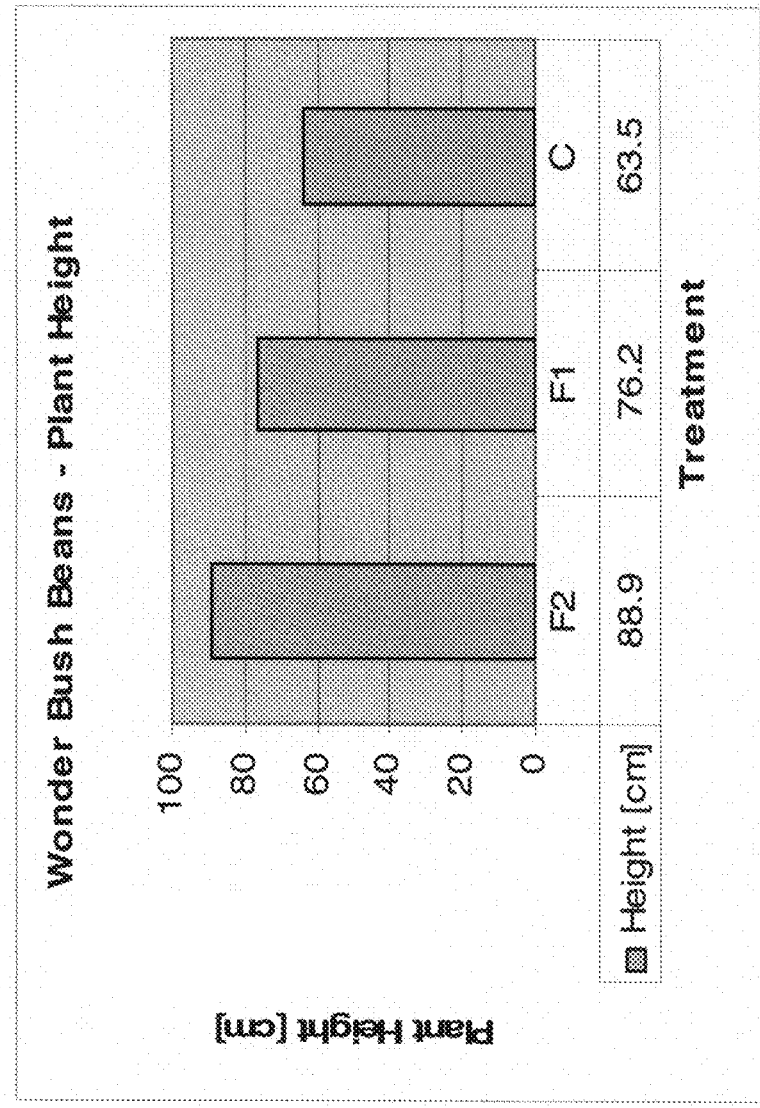
FIG. 24 shows an exemplary comparison of Wonder bush beans grown under Greenhouse Evaluation conditions plant height A) and yield B) grown in the presence of polymicrobial formulations F1 and F2 as compared to a control with no formulation added
Figure 24B:
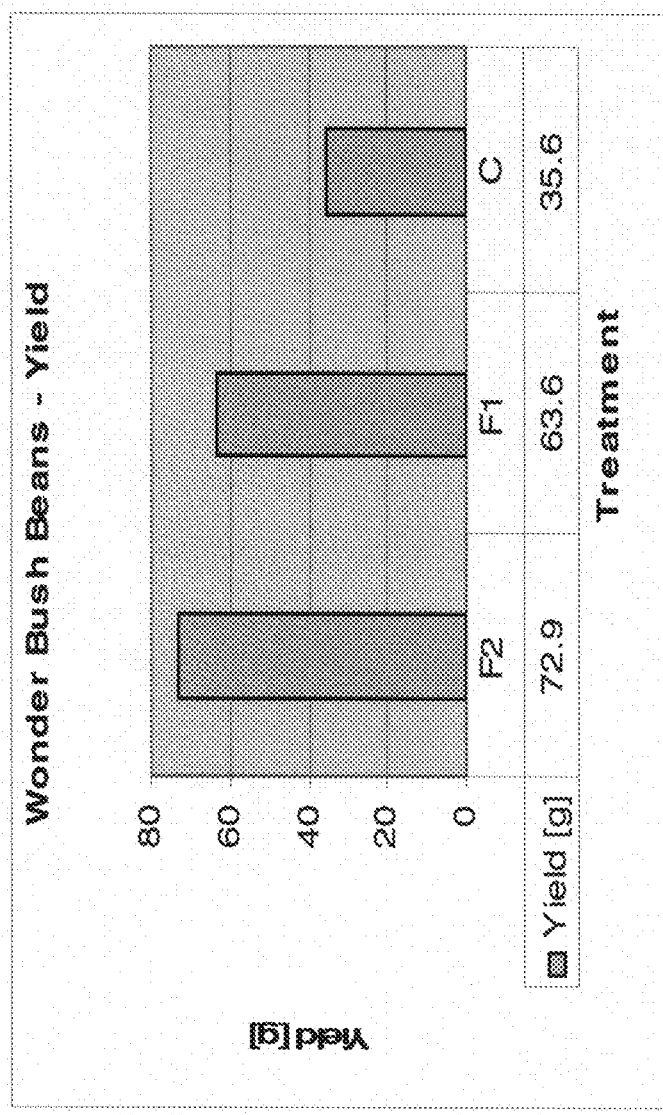
Figure 28B:
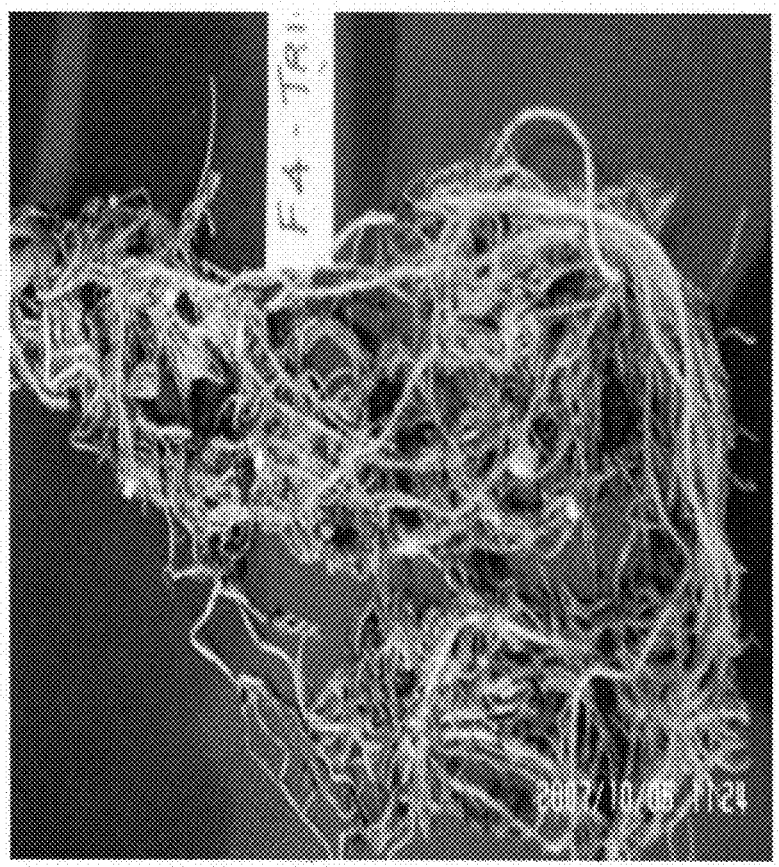
FIG. 28 shows an exemplary root nodule formation in pea plants treated with formulations consisting of either, A) bacterial strains (F3) and B) *Trichoderma* strains (F4).

The results further demonstrated *Trichoderma* specific induction of nodulation on the roots of garden beans (see, F3 induced nodulation in FIG. 15A compared to F4 induced nodulation in 15B) and pea plants F3 induced nodulation as demonstrated in FIGS. 28A and F4 in FIG. 28B. See, Table 8 below.

TABLE 8

Results of root nodulation in garden beans treated with either bacterial microbes or fungal microbes.

| Treatment | Nodulation |
|---|---|
| Symbiotic Diazotrophs** + HG | Yes* |
| Trichoderma + HG | Yes* |
| HG only | None |

*Nodulation observed with diazotrophs (nitrogen-fixating) are larger and more numerous, and different from those seen with Trichoderma treatment.
**Formulated as described herein.

Sumagro 3 and Sumagro 4 were prepared in a sterilized nitrogen-free mineral salts solution (N-free Mineral solution) as described herein. Plants were seeded and treated in pots containing 500 g of sterile vermiculite plus potting soil, in a ratio of 75:25. There were 4 plants per each pot. Treatments included 1. control (water); 2. N-free Mineral solution (120 ml of N free solution), 3. F3 plus N-free Mineral solution (4 ml F3 plus 120 ml of N free solution), 3. F4 plus N-free Mineral solution (4 ml F4 plus 120 ml N-free Mineral solution), and 4. HG (Humagro).

Seeds were soaked in respective treatments for 1 hour prior to sowing. The duration of the experiment was 4 weeks. Nodules on the roots of plants in a given treatment were recorded. The Figures show roots of garden beans treated for 30 days, both, 2×, soaking in 4 ml 30 minutes followed by planting, remaining formulation was added to soil at site of seeding.

Nodulation seen with F3 (Rhizobial Mixture) and F4 (*Trichoderma* mixture) formulations. Note the clear nodulation seen with F4 (*Trichoderma* mixture) alone. This *Trichoderma*-dependent nodulation was determined in the absence of nodulation without *Trichoderma* under otherwise identical conditions in similar plants.

Enhanced roof nodulation was observed in all the legumes treated with the formulations as compared to the controls. The inventors concluded that *Trichoderma*-induced root nodule formation by native soil bacteria.

EXAMPLE V

This example demonstrated the plant growth enhancing effects of formulations of the present inventions, specifically two types of Sumagro 2 (F2) formulation each prepared with a different type of carrier solution, on a mixture of grass plants grown under greenhouse conditions. As shown, the inventors further demonstrated enhanced growth of plants with Sumagro 2 comprising a mineral solution as a carrier in place of the Humagro carrier solution used in prior Examples.

Specifically, grass plant seed mixtures were soaked for 30 minutes in their treatment solution, seeded in greenhouse pots and further treated with F2 formulated in Humagro (HG), F2 formulated in the mineral solution (NF2), as compared to similar grass plants treated with HG and grass plants treated with mineral solution (MM), as described herein. FIGS. 24A and B shows an exemplary effect of HG vs. F2 (in HG) vs. MM vs. NF2 (F2 in Mineral solution and no HG). Note the increase in growth of grass plants in NF2 that is identical to F2.

These results show that F2 and NF2 stimulate an increase in the growth and thus productivity of a mixture of grasses. Further, these results demonstrate that a mineral solution is an effective carrier solution for formulations of the present inventions.

EXAMPLE VI

This example demonstrated the plant growth enhancing effects of formulations of the present inventions on a variety of switchgrass plants in Greenhouse evaluations.

The inventors planted grass seeds of the following varieties for testing with the F2 formulation as described in Example 1. Control pots were merely treated with water. While the varieties showed some enhanced growth, 27A) Carthage and 27C Dacotah (Dakota), while 27B) Cave-in-Rock and more significantly 27D) Forestburg showed significantly enhanced growth when fed F2 formulation of the present inventions.

Further contemplated are additional varieties for use, singly or as mixtures, with biomass increasing formulations and/or biocontrol formulations of the present inventions including but not limited to "Trailblazer, Sunburst, Summer, Shelter=NY4006, REAP 921, Pathfinder, Pangburn, Nebraska 28, Kanlow, Forestburg, Carthage=NJ-50, Caddo, Blackwell, Alamo, et cetera.

EXAMPLE VII

This example demonstrated the biological control effects of isolates of the present inventions for inhibiting the growth of phytopathogenic microbes.

The inventors discovered that F2, which contains fungal isolates of the present inventions shown to be active against pathogenic fungal isolates, provided protection against powdery mildew. Further, F4 (a fungal strain mixture) provided plant protection to a variety of pathogens, including but no limited to *Curvularia lunata* (leaf spot of tomato; *Fusarium solani* (tomato wilt); *Bipolaris oryzae*, (brown leaf spot of rice); *Magnoporthe grisea*, (blast disease of rice); *Alternaria alternata* (early blight of tomato and potato), and *Rhizoctonia solani* (Sheath blight of rice) as well as the plant-pathogenic bacterium, *Xanthomonas oryzae* (bacterial blight of rice). In particular, all the *Trichoderma* species isolated herein were screened for their biocontrol potential against known plant pathogenic fungi using the dual plate technique.

Isolates of the present inventions were tested for biocontrol effects, including but not limited to inhibiting the growth of phytopathogenic fungal species. In particular, isolates of *Trichoderma harzianum, T. viridi, T. longibrachiatum, T. virens*, and the bacteria *Pseudomonas fluorescens*, were tested as possible biocontrol agents of *Alternaria alternata* and *Curvularia* Sp. causing leaf spot of tomato under in vitro conditions. *T. harzianum* showed dominance and hyper parasitism on contact over *A. alternata* and *Curvularia* sp. *T. virens, T. longibrachiatum* and *T. viridi* also inhibited and hyper parasitized *A. alternata*. Biocontrol was governed by different mechanisms such as competition for space and nutrients, mycoparasitism, and possible antibiosis.

Figure 29A:
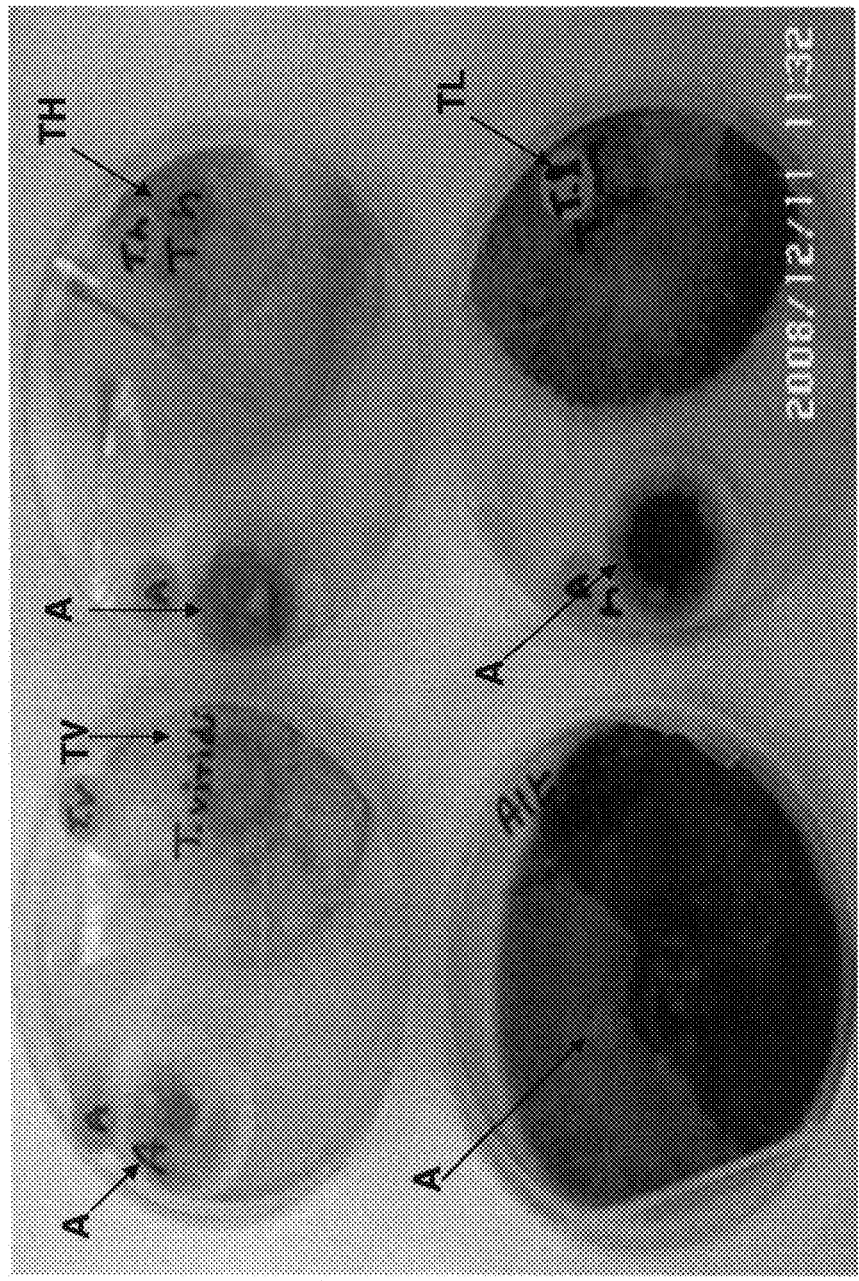
FIG. 29 shows an exemplary biological control effect of fungal isolates of the present inventions on a pathogenic fungus A) A—*Alternaria alternata* (plant pathogen sometimes called a Tomato leaf spot pathogen) grown in the presence of fungal isolates of the present inventions: TH—*Trichoderma harzianum* (showing Bio-control of fungus); TV—*T. viride* (showing Bio-control of fungus); TL—*T. longibrachiatum* (showing Bio-control of fungus) and B) A—*Alternaria alternata* (plant pathogen sometimes called a Tomato leaf spot pathogen); C—*Curvularia* sp. (Tomato leaf spot pathogen); and F—*Fusarium solani* (Tomato pathogen) grown next to B5—Antagonistic Bacterial strain *Pseudomonas fluorescens* isolate of the present inventions.
Figure 29B:
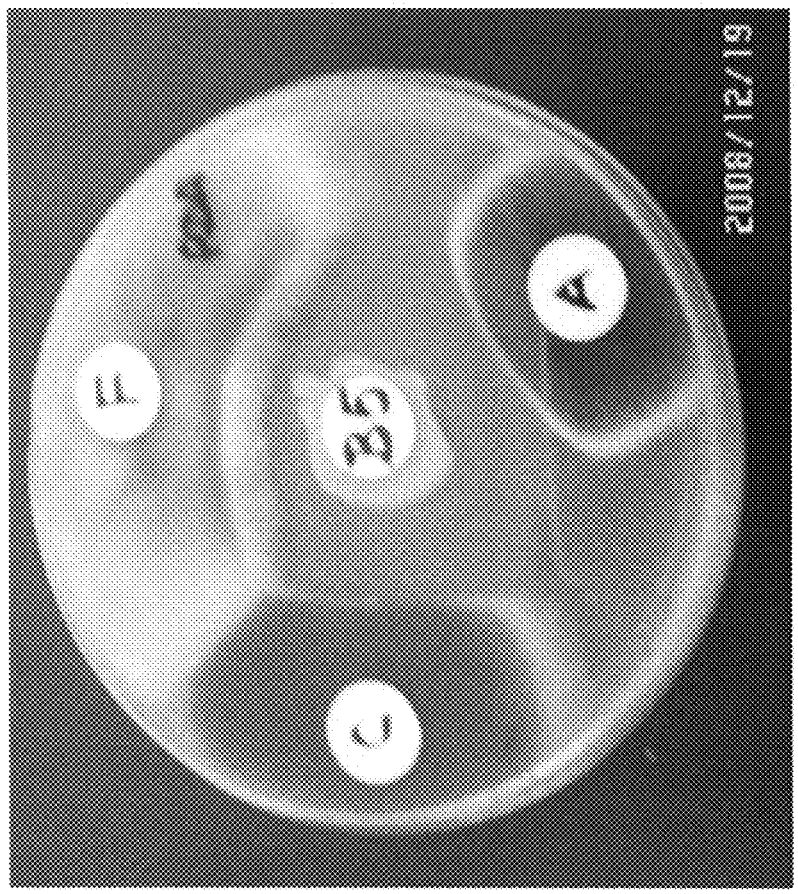

Inhibition of plant pathogens—Dual culture plate method. In this Example, four different species of *Trichoderma* that are present in. F2 were tested against *Alternaria alternata*, an important pathogen of tomato plants. As shown in exemplary FIG. 29A, where *Alternaria alternata* would typically grow over an entire plate of agar (plate in lower left of A), each of the three fungal isolates tested caused inhibition of growth of the pathogenic fungus. Such that TH *Trichoderma harzianum*; TV *T. virile*; and TL *T. longibrachiatum* were designated by the inventors as Bio-control fungus. *T. virens*, was also tested against *Alternaria alternata* and found to have anti-fungal properties. Further, a B5 bacteria strain, *Pseudomonas fluorescens* of the present inventions was shown to have anti-growth effects on several types of pathogens, including A *Alternaria alternata* (Tomato leaf spot pathogen); C *Curvularia* sp. (Tomato leaf spot pathogen); F *Fusarium solani* (Tomato pathogen) as shown in FIG. 29B.

Figure 30A:
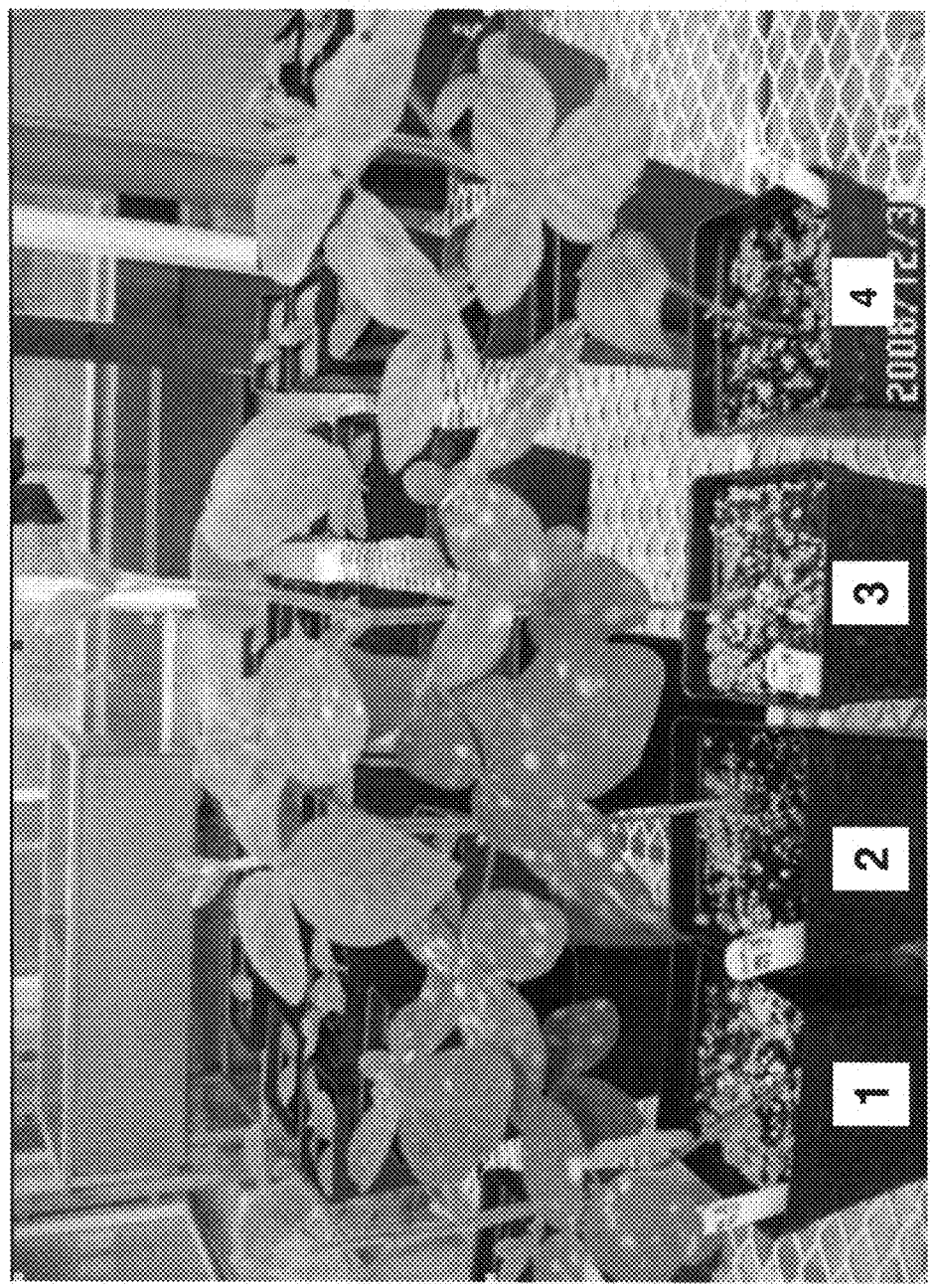
FIG. 30 shows an exemplary comparison of formulations demonstrating biocontrol against Powdery mildew: A) soybean plants infected by Powdery mildew showing that an F2 treated Soybean plant (4) is free from Powdery mildew infection unlike the plants treated merely with conventional fertilizer (NPK) (plants 1, 2 and 3) and squash plants exposed to powdery mildew in a greenhouse B) with F2 treatments and C) without F2 treatments.
Figure 30B:
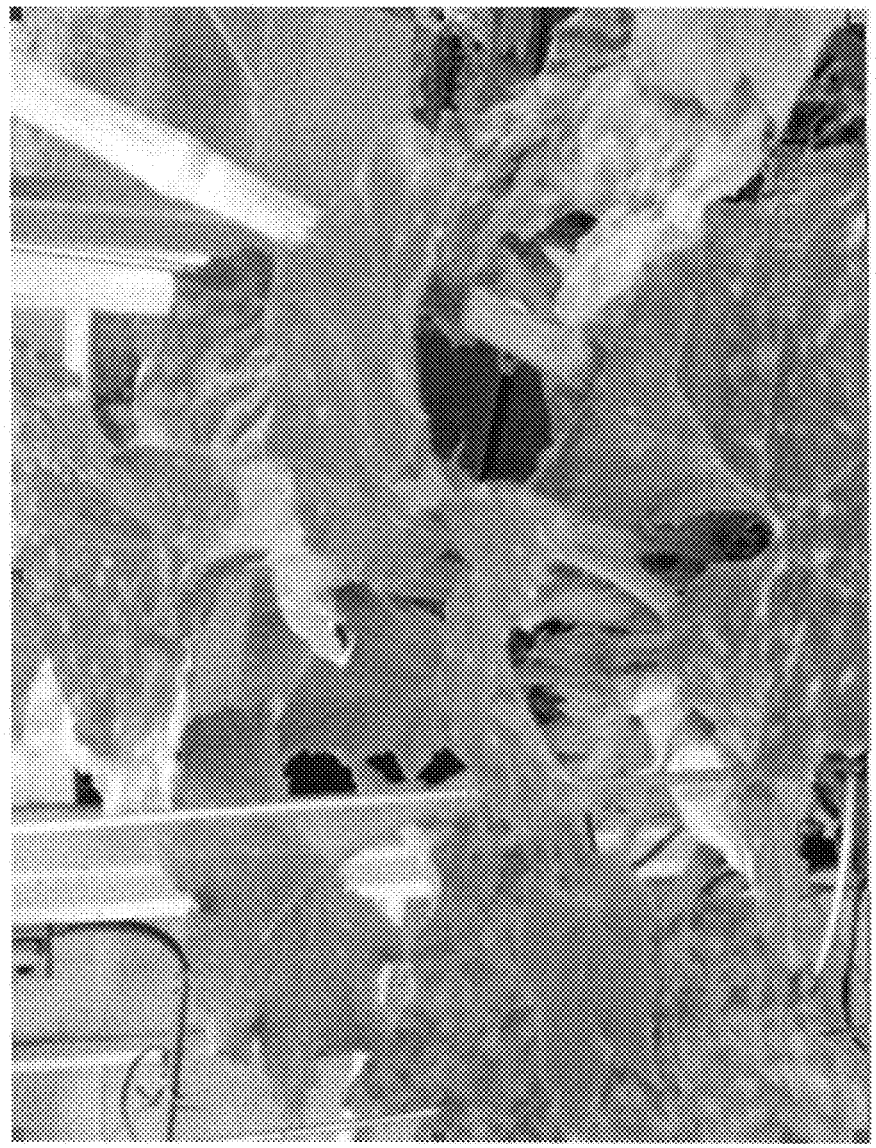
Figure 30C:

Greenhouse observations. During the course of formulation testing under Greenhouse conditions, the inventors observed plants infected with powdery mildew caused by *Microsphaera diffusa*. Surprisingly, infected plants in adjacent pots showed significant resistance to infection when grown in the presence of F2. Specifically, exemplary comparisons are demonstrated in FIG. 30A where soybean plants 1-3 were treated with conventional fertilizer while plant 4 was undergoing F2 treatment. Plants 1-3 show large white spots indicative of infection while plant 4 is essentially free of fungal spots. Even more striking were squash plants with numerous blooms undergoing F2 treatment showing signs of fungal infection on larger (older) green leaves while a control squash plant is wilted and almost dead following symptoms of Powdery mildew infections.

Thus F2-treated plants are highly resistant to Powdery mildew infections.

EXAMPLE VIII

This example provides an exemplary method for growing mixtures of microbes for long-term storage. Modifications of this method are contemplated for providing deposits under the Budapest Treaty.

The inventors grew individual bacteria isolates listed for Sumagro 5, Table 2C (also the bacterial portion of the Sumagro-2 mixture) according to methods provided herein. These isolates were mixed together to form a bacterial mixture (labeled F2A) in Sumagro-2 which is combined with the mixture of fungal isolates (labeled F2B) described below. Further, a F2A mixture is contemplated for shipment to the NRRL for deposit under the Budapest Treaty as NRRL accession B-50215.

Similarly, the fungal isolates listed for Sumagro 4, Table 4, (also the fungal portion of the Sumagro-2 mixture) were grown in the inventor's laboratory, described supra. These isolates were mixed together to form a fungal isolate mixture (labeled F2B) for use in combination with F2A. Further, a F2B fungal isolate mixture is contemplated for shipment to the NRRL for deposit under the Budapest Treaty as NRRL accession 50216.

An exemplary reference for culture preservation and re-growth of the bacterial and fungal isolates is provided, Gherna, R. L. and C. A. Reddy. 2007. Culture Preservation, p 019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages; herein incorporated by reference.

We claim:

1. A microbial formulation, wherein said formulation comprises a microbial mixture of a bacterial mixture having N.R.R.L accession number B-50215 and a fungal mixture having N.R.R.L accession number 50216.

2. The microbial formulation of claim 1, further comprising, a liquid carrier.

3. The microbial formulation of claim 2, wherein said liquid carrier comprises water and humic acid.

4. The microbial formulation of claim 3, wherein said humic acid is at a concentration of 12% volume of humic acid (ml)/volume of solution (ml).

5. The microbial formulation of claim 2, wherein said liquid carrier has a pH of 7.0.

6. The microbial formulation of claim 2, wherein said microbial mixture has a microbe concentration in the liquid carrier that ranges from $10^{10}$-$10^{17}$ microbes per milliliter of liquid.

7. The microbial formulation of claim 1, wherein the formulation is selected from the group consisting of a liquid, a dried formulation, and a wettable powder.

8. The microbial formulation of claim 7, wherein the dried formulation is a freeze dried liquid formulation.

9. The microbial formulation of claim 1, wherein said formulation is a biocontrol formulation for a pathogen selected from the group consisting of leaf spot of tomato and powdery mildew.

10. The microbial formulation of claim 9, wherein said pathogen comprises a *Curvularia* species and an *Alternaria* species.

11. The microbial formulation of any of claim 10 and 2-7, further comprising an adjuvant selected from the group consisting of a wetting agent, spreading agent, dispersing agent, sticking agent, or adhesive.

* * * * *

UNITED STATES PATENT AND TRADEMARK OFFICE
CERTIFICATE OF CORRECTION

PATENT NO. : 8,822,190 B2　　　　　　　　　　　　　　　　　　　　　　　Page 1 of 1
APPLICATION NO. : 12/354241
DATED : September 2, 2014
INVENTOR(S) : Reddy et al.

It is certified that error appears in the above-identified patent and that said Letters Patent is hereby corrected as shown below:

In the Claims

In column 52, line 28, in Claim 11, delete "claim 10 and 2-7" and insert --claims 1-7--, therefor Signed and Sealed this
Twenty-eighth Day of July, 2015

Michelle K. Lee
*Director of the United States Patent and Trademark Office*